US007998959B2

(12) United States Patent
Yao et al.

(10) Patent No.: US 7,998,959 B2
(45) Date of Patent: Aug. 16, 2011

(54) MODULATORS OF 11-β HYDROXYL STEROID DEHYDROGENASE TYPE 1, PHARMACEUTICAL COMPOSITIONS THEREOF, AND METHODS OF USING THE SAME

(75) Inventors: Wenqing Yao, Kennett Square, PA (US); David M. Burns, Philadelphia, PA (US); Lihua Chen, Boothwyn, PA (US); Jincong Zhuo, Boothwyn, PA (US); Chunhong He, Boothwyn, PA (US)

(73) Assignee: Incyte Corporation, Wilmington, DE (US)

( * ) Notice: Subject to any disclaimer, the term of this patent is extended or adjusted under 35 U.S.C. 154(b) by 1148 days.

(21) Appl. No.: 11/652,191

(22) Filed: Jan. 11, 2007

(65) Prior Publication Data

US 2007/0197506 A1  Aug. 23, 2007

Related U.S. Application Data

(60) Provisional application No. 60/808,884, filed on May 26, 2006, provisional application No. 60/758,352, filed on Jan. 12, 2006.

(51) Int. Cl.

| C07D 207/16 | (2006.01) |
| C07D 403/04 | (2006.01) |
| A61K 31/40 | (2006.01) |
| A61P 3/04 | (2006.01) |
| A61P 3/06 | (2006.01) |
| A61P 3/10 | (2006.01) |
| A61P 9/00 | (2006.01) |
| A61P 27/00 | (2006.01) |

(52) U.S. Cl. ............... 514/235.5; 514/255.05; 514/269; 514/278; 514/361; 514/397; 514/409; 544/141; 544/315; 544/405; 546/15; 548/127; 548/314.7; 548/410

(58) Field of Classification Search .................... None
See application file for complete search history.

(56) References Cited

U.S. PATENT DOCUMENTS

| 4,076,819 | A | 2/1978 | Maffrand |
| 4,439,606 | A | 3/1984 | Du et al. |
| 5,442,064 | A | 8/1995 | Pieper et al. |
| 5,614,534 | A | 3/1997 | Binet et al. |
| 5,633,247 | A | 5/1997 | Baldwin et al. |
| 5,668,138 | A | 9/1997 | Baziard-Mouysset et al. |
| 5,852,029 | A | 12/1998 | Fisher et al. |
| 5,981,754 | A | 11/1999 | Badone et al. |
| 6,355,617 | B1 * | 3/2002 | Luke et al. ............ 514/16 |
| 6,547,958 | B1 | 4/2003 | Elomari et al. |
| 7,304,081 | B2 * | 12/2007 | Yao et al. ............ 514/370 |
| 2003/0229119 | A1 | 12/2003 | Kym et al. |
| 2005/0020645 | A1 | 1/2005 | Ohta et al. |
| 2005/0080078 | A1 | 4/2005 | Aquila et al. |
| 2005/0282858 | A1 | 12/2005 | Yao et al. |
| 2005/0288317 | A1 | 12/2005 | Yao et al. |
| 2005/0288329 | A1 | 12/2005 | Yao et al. |
| 2005/0288338 | A1 | 12/2005 | Yao et al. |
| 2006/0004049 | A1 | 1/2006 | Yao et al. |
| 2006/0009471 | A1 | 1/2006 | Yao et al. |
| 2006/0009491 | A1 | 1/2006 | Yao et al. |
| 2006/0019977 | A1 | 1/2006 | Habashita et al. |
| 2006/0106045 | A1 | 5/2006 | Hughes et al. |
| 2006/0116382 | A1 | 6/2006 | Yao et al. |
| 2006/0122197 | A1 | 6/2006 | Yao et al. |
| 2006/0122210 | A1 | 6/2006 | Yao et al. |
| 2006/0149070 | A1 | 7/2006 | Rohde et al. |
| 2006/0199816 | A1 | 9/2006 | Gillespie et al. |
| 2007/0066584 | A1 | 3/2007 | Yao et al. |
| 2007/0129345 | A1 | 6/2007 | Zhuo et al. |
| 2007/0197530 | A1 | 8/2007 | Li et al. |
| 2007/0208001 | A1 | 9/2007 | Zhuo et al. |
| 2007/0213311 | A1 | 9/2007 | Li et al. |
| 2007/0270424 | A1 | 11/2007 | Li et al. |
| 2007/0293529 | A1 | 12/2007 | Li et al. |

FOREIGN PATENT DOCUMENTS

| DE | 2623567 | 12/1976 |
| EP | 1683797 | 7/2006 |
| JP | 4334357 | 11/1992 |
| WO | WO 02/06868 | 1/2002 |
| WO | WO 03037847 | 5/2003 |
| WO | WO 03/045912 | 6/2003 |
| WO | WO 03/053915 A2 | 7/2003 |
| WO | WO 03/104207 | 12/2003 |
| WO | WO 2004056745 | 7/2004 |
| WO | WO 2004065351 | 8/2004 |
| WO | WO 2004/082687 | 9/2004 |
| WO | WO 2004089470 | 10/2004 |
| WO | WO 2004089896 | 10/2004 |
| WO | WO 2004/096139 | 11/2004 |
| WO | WO 2005047286 | 5/2005 |
| WO | WO 2005060963 | 7/2005 |
| WO | WO 2005063745 | 7/2005 |
| WO | WO 2005108359 | 11/2005 |
| WO | WO 2006/020598 | 2/2006 |
| WO | WO 2006012226 | 2/2006 |
| WO | WO 2006/040329 | * 4/2006 |
| WO | WO 2006/047196 | 5/2006 |

(Continued)

OTHER PUBLICATIONS

Hughes et al., "Total Synthesis of (−) Amathaspiramide F", Angew. Chem. Int. Ed., 41(23), 4556-4559, 2002.*

Hughes et al., "The total synthesis of (−)-Amathaspiramide F**'", *Angewandte Chemie, Int 'l. Ed.*, 41(23), 4556-4559; 2002.

(Continued)

*Primary Examiner* — Fiona T Powers
(74) *Attorney, Agent, or Firm* — Fish & Richardson P.C.

(57) ABSTRACT

The present invention relates to inhibitors of 11-β hydroxyl steroid dehydrogenase type 1 and pharmaceutical compositions thereof. The compounds of the invention can be useful in the treatment of various diseases associated with expression or activity of 11-β hydroxyl steroid dehydrogenase type 1 such as obesity and diabetes.

42 Claims, No Drawings

OTHER PUBLICATIONS

Morris et al., "Amathaspiramides A-F, Novel Brominated Alkaloids from the Marine Bryozoan *Amathia wilsoni*", Journal of Natural Products, 62(5), 688-693, 1999.

Xu et al., "Synthesis of Aza/Oxaspiro-γ-lactams by Radical Translocation Cyclization Reactions", *Synlett*, (12), 1865-1868, 2005.

International Search Report and Written Opinion for International Appln. No. PCT/US2007/000695 dated Jan. 31, 2008 (15 pgs.).

International Preliminary Report on Patentability for International Appln. No. PCT/US2007/000695 dated Jul. 15, 2008 (9 pgs.).

Alberts et al. Endocrinology (2003) 144: 4755-4762.

Albiston et al. (1994) Mol. Cell. Endocrin. 105: R11-R17.

Barf et al. (2002) J. Med. Chem. 45: 3813-3815.

Bellows et al. (1998) Bone 23: 119-125.

Bhargava et al., (2001), Endo 142: 1587-1594.

Billaudel and Sutter (1979) Horm. Metab. Res. 11: 555-560.

Bioreversible Carriers in Drug Design, ed. Edward B. Roche, American Pharmaceutical Association and Pergamon Press, 1987.

Blum, et al., (2003) Prog. Nucl. Acid Res. Mol. Biol. 75:173-216.

Bujalska et al. (1997) Lancet 349: 1210-1213.

Canalis (1996) J. Clin. Endocrinol. Metab. 81: 3441-3447.

Conn, (1955), J. Lab. Clin. Med. 45: 6-17.

Cooper et al. (2000) Bone 27: 375-381.

Database CAPLUS on STN (Columbus, OH, USA) No. 108:131815, Preparation and testing of f7-amino-1,3-dihydro-2H-imidazo[4,5-b]quinolin-2-ones as phosphodiesterase and bloodplatelet aggregation inhibitors, abstract, Meanwell, et al. (1988).

Database CAPLUS on STN (Columbus, OH, USA) No. 118:255342, {re[artopm pf M-heterpcuc;u;carbpmu;a,omp acids and analogs as prolylendopeptidase inhibotors' abstract, Hosoda et al. (1993).

Database CAPLUS on STN (Columbus, OH, USA) No. 126:317635, "Alpha-amino acids derived from ornithine as building blocks for peptide synthesis" abstract, Gescrinier et al. j. Pep. Res. 49(2):183-189 (1997).

Database CAPLUS on STN (Columbus, OH, USA) No. 143:78479, "Preparation of amino acid derivatives as novel M3 muscarinic acetylcholine receptor antagonists" abstract, Busch et al. (2005).

Davani et al. (2000) J. Biol. Chem. 275: 34841-34844.

Draper et al. (2003) Nat. Genet. 34: 434-439.

Edwards et al. (1988) Lancet 2: 986-989.

Engeli, et al., (2004) Obes. Res. 12: 9-17.

Funder et al. (1988), Science 242: 583-585.

Greene, et al., Protective Groups in Organic Synthesis, 2d. Ed., Wiley & Sons, 1991.

Gu et al., "Discovery of 4-heteroarylbicyclo[2.2.2]octyltriazoles as potent and selective inhibitors of 11β-HSD1: Novel therapeutic agents for the treatment of metabolic syndrome," *Bioorg. Med. Chem. Lett.*, 15:5266-5269 (2005).

Hermanowski-Vosatka et al. (2005) J. Exp. Med. 202: 517-527.

Jausons-Loffreda et al. J. Biolumin and Chemilumin, 9:217-221 (1994).

Journal of Pharmaceutical Science, 66, 2 (1977).

Kotelevstev et al. (1997) Proc. Natl. Acad. Sci. 94: 14924-14929.

Kurukulasuriya , et al., (2003) Curr. Med. Chem. 10: 123-53.

Leonardi et al., "Synthesis, Pharmacological Evaluation, and Structure—Activity Relationship and Quantitative Structure—Activity Relationship Studies on Novel Derivatives of 2,4-Diamino-6,7-dimethoxyquinazoline $\alpha_1$-Adrenoceptor Antagonists," *J. Med. Chem.*, 42:427-437 (1999).

Lindsay et al. (2003) J. Clin. Endocrinol. Metab. 88: 2738-2744.

Livingstone et al. (2000) Endocrinology 131: 560-563.

Low et al. (1994) J. Mol. Endocrin. 13: 167-174.

Lupien et al. (1998) Nat. Neurosci. 1: 69-73.

Mallams et al., "Inhibitors of Farnesyl Protein Transferase. 4-Amido, 4-Carbamoyl, and 4-Carboxamido Derivatives of 1-(8-Chloro-6,11-dihydro-5H-benzo[5,6]-cyclohepta[1,2-b]pyridin-11- yl)piperazine and 1-(3-Bromo-8-chloro-6,11-dihydro-5H-benzo[5,6]cyclohepta [1,2-b]pyridin-11- yl)piperazine," *J. Med. Chem.*, 41:877-893 (1998).

Masuzaki et al. (2001) Science 294: 2166-2170.

Masuzaki et al. (2003) J. Clinical Invest. 112: 83-90.

Masuzaki, et al., (2003) Curr. Drug Targets Immune Endocr. Metabol. Disord. 3: 255-62.

Matsuzawa et al. (1999) Ann. N.Y. Acad. Sci. 892: 146-154.

McEwen and Sapolsky (1995) Curr. Opin. Neurobiol. 5: 205-216.

Miller and Chrousos (2001) Endocrinology and Metabolism, eds. Felig and Frohman (McGraw-Hill, New York), 4th Ed.: 387-524.

Moeller et al., "Anodic Amide Oxidations in the Presence of Electron-Rich Phenyl Rings: Evidence for an Intramolecular Electron-Transfer Mechanism," *J. Org. Chem.*, 56:1058-1067 (1991).

Morton et al. (2001) J. Biol. Chem. 576: 41293-41300.

Morton et al. (2004) Diabetes 53: 931-938.

Ogawa et al. (1992) J. Clin. Invest. 90: 497-504.

Pitt et al., New England J. Med. (1999), 341: 709-719.

Pitt et al., New England J. Med. (2003), 348: 1309-1321.

Rajan et al. (1996) J. Neurosci. 16: 65-70.

Rask et al. (2001) J. Clin. Endocrinol. Metab. 86: 1418-1421.

Rauz et al. (2001) Invest. Ophthalmol. Vis. Sci. 42: 2037-2042.

Reaven (1993) Ann. Rev. Med. 44: 121-131.

Remington's Pharmaceutical Sciences, 17th ed., Mack Publishing Company, Easton, Pa., 1985, p. 1418.

Sandeep et al. (2004) Proc. Natl. Acad. Sci. 101: 6734-6739.

Stokes et al. (2000) Invest. Ophthalmol. Vis. Sci. 41: 1629-1683.

T. Higuchi and V. Stella, "Pro-drugs as Novel Delivery Systems," vol. 14 of the A.C.S. Symposium Series, and in Bioreversible Carriers in Drug Design, ed. Edward B. Roche, American Pharmaceutical Association and Pergamon Press, 1987.

Wajchenberg, B.L. (2000) Endocrine Reviews 21: 697-738.

Wake et al. (2003) J. Clin. Endocrinol. Metab. 88: 3983-3988.

Walker et al. (1979) Hypertension 1: 287-291.

Wilson et al. (1998) Proc. Natl. Acad. Sci. 95: 10200-10205.

Cho et al., "Synthesis and Palladium-Catalyzed Coupling Reactions of Enantiopure p-Bromophenyl Methyl Sulfoximine," *J. Org. Chem.*, 2005, 70, 2346-2349.

Nie et al., "Structure-Based Design, Synthesis, and Study of Potent Inhibitors of β-Keto-acyl Carrier Protein Synthase III as Potential Antimicrobial Agents," *J. Med. Chem.*, 2005, 48, 1596-1609.

Wang et al., "An Improved Ullmann-Ukita-Buchwald-Li Conditions for CuI-Catalyzed Coupling Reaction of 2-Pyridones with Aryl Halides," *Tetrahedron*, 2005, 61, 2931-2939.

Yau et al., "Lack of Tissue Glucocorticoid Reactivation in 11β-Hydroxysteroid Dehydrogenase Type 1 Knockout Mice Ameliorates Age-Related Learning Impairments," *Proc. Natl. Acad. Sci.*, 2001, 98:4716-4721.

Office Action (non-final) dated May 6, 2008 issued by Examiner Taofiq A. Solola for U.S. Appl. No. 11/159,862 (27 pgs.).

\* cited by examiner

MODULATORS OF 11-β HYDROXYL STEROID DEHYDROGENASE TYPE 1, PHARMACEUTICAL COMPOSITIONS THEREOF, AND METHODS OF USING THE SAME

CROSS-REFERENCE TO RELATED APPLICATIONS

This application claims the benefit of U.S. Ser. Nos. 60/758,352, filed Jan. 12, 2006 and 60/808,884, filed May 26, 2006, the disclosures of each of which is incorporated herein by reference in its entirety.

TECHNICAL FIELD

The present invention relates to modulators of 11-β hydroxyl steroid dehydrogenase type 1 (11βHSD1), compositions thereof, and methods of using the same.

BACKGROUND

Glucocorticoids are steroid hormones that have the ability to modulates a plethora of biological processes including development, neurobiology, inflammation, blood pressure, and metabolism. In humans, the primary endogenously produced glucocorticoid is cortisol. Two members of the nuclear hormone receptor superfamily, glucocorticoid receptor (GR) and mineralcorticoid receptor (MR), are the key mediators of cortisol function in vivo. These receptors possess the ability to directly modulate transcription via DNA-binding zinc finger domains and transcriptional activation domains. This functionality, however, is dependent on the receptor having first bound to ligand (cortisol); as such, these receptors are often referred to as 'ligand-dependent transcription factors'.

Cortisol is synthesized in the zona fasciculate of the adrenal cortex under the control of a short-term neuroendocrine feedback circuit called the hypothalamic-pituitary-adrenal (HPA) axis. Adrenal production of cortisol proceeds under the control of adrenocorticotrophic hormone (ACTH), a factor produced and secreted by the anterior pituitary. Production of ACTH in the anterior pituitary is itself highly regulated, being driven by corticotropin releasing hormone (CRH) produced by the paraventricular nucleus of the hypothalamus. The HPA axis functions to maintain circulating cortisol concentrations within restricted limits, with forward drive at the diurnal maximum or during periods of stress being rapidly attenuated by a negative feedback loop resulting from the ability of cortisol to suppress ACTH production in the anterior pituitary and CRH production in the hypothalamus.

The importance of the HPA axis in controlling glucocorticoid excursions is evident from the fact that disruption of this homeostasis by either excess or deficient secretion or action results in Cushing's syndrome or Addison's disease, respectively (Miller and Chrousos (2001) Endocrinology and Metabolism, eds. Felig and Frohman (McGraw-Hill, New York), 4$^{th}$ Ed.: 387-524). Interestingly, the phenotype of Cushing's syndrome patients closely resembles that of Reaven's metabolic syndrome (also known as Syndrome X or insulin resistance syndrome) including visceral obesity, glucose intolerance, insulin resistance, hypertension, and hyperlipidemia (Reaven (1993) Ann. Rev. Med. 44: 121-131). Paradoxically, however, circulating glucocorticoid levels are typically normal in metabolic syndrome patients.

For decades, the major determinants of glucocorticoid action were believed to be limited to three primary factors: 1) circulating levels of glucocorticoid (driven primarily by the HPA axis), 2) protein binding of glucocorticoids in circulation (upward of 95%), and 3) intracellular receptor density inside target tissues. Recently, a fourth determinant of glucocorticoid function has been identified: tissue-specific pre-receptor metabolism. The enzymes 11-beta hydroxysteroid dehydrogenase type 1 (11βHSD1) and 11-beta hydroxysteroid dehydrogenase type 2 (11βHSD2) catalyze the interconversion of active cortisol (corticosterone in rodents) and inactive cortisone (11-dehydrocorticosterone in rodents). 11βHSD1 has been shown to be an NADPH-dependent reductase, catalyzing the activation of cortisol from inert cortisone (Low et al. (1994) J. Mol. Endocrin. 13: 167-174); conversely, 11βHSD2 is an NAD-dependent dehydrogenase, catalyzing the inactivation of cortisol to cortisone (Albiston et al. (1994) Mol. Cell. Endocrin. 105: R11-R17). The activity of these enzymes has profound consequences on glucocorticoid biology as evident by the fact that mutations in either gene cause human pathology. For example, 11βHSD2 is expressed in aldosterone-sensitive tissues such as the distal nephron, salivary gland, and colonic mucosa where its cortisol dehydrogenase activity serves to protect the intrinsically non-selective mineralcorticoid receptor from illicit occupation by cortisol (Edwards et al. (1988) Lancet 2: 986-989). Individuals with mutations in 11βHSD2 are deficient in this cortisol-inactivation activity and, as a result, present with a syndrome of apparent mineralcorticoid excess (also referred to as 'SAME') characterized by hypertension, hypokalemia, and sodium retention (Wilson et al. (1998) Proc. Natl. Acad. Sci. 95: 10200-10205). Likewise, mutations in 11βHSD1 and a co-localized NADPH-generating enzyme, hexose 6-phosphate dehydrogenase (H6PD), can result in cortisone reductase deficiency (also known as CRD; Draper et al. (2003) Nat. Genet. 34: 434-439). CRD patients excrete virtually all glucocorticoids as cortisone metabolites (tetrahydrocortisone) with low or absent cortisol metabolites (tetrahydrocortisols). When challenged with oral cortisone, CRD patients exhibit abnormally low plasma cortisol concentrations. These individuals present with ACTH-mediated androgen excess (hirsutism, menstrual irregularity, hyperandrogenism), a phenotype resembling polycystic ovary syndrome (PCOS).

Given the ability of 11βHSD1 to regenerate cortisol from inert circulating cortisone, considerable attention has been given to its role in the amplification of glucocorticoid function. 11βHSD1 is expressed in many key GR-rich tissues, including tissues of considerable metabolic importance such as liver, adipose, and skeletal muscle, and, as such, has been postulated to aid in the tissue-specific potentiation of glucocorticoid-mediated antagonism of insulin function. Considering a) the phenotypic similarity between glucocorticoid excess (Cushing's syndrome) and the metabolic syndrome with normal circulating glucocorticoids in the later, as well as b) the ability of 11βHSD1 to generate active cortisol from inactive cortisone in a tissue-specific manner, it has been suggested that central obesity and the associated metabolic complications in syndrome X result from increased activity of 11βHSD1 within adipose tissue, resulting in 'Cushing's disease of the omentum' (Bujalska et al. (1997) Lancet 349: 1210-1213). Indeed, 11βHSD1 has been shown to be upregulated in adipose tissue of obese rodents and humans (Livingstone et al. (2000) Endocrinology 131: 560-563; Rask et al. (2001) J. Clin. Endocrinol. Metab. 86: 1418-1421; Lindsay et al. (2003) J. Clin. Endocrinol. Metab. 88: 2738-2744; Wake et al. (2003) J. Clin. Endocrinol. Metab. 88: 3983-3988).

Additional support for this notion has come from studies in mouse transgenic models. Adipose-specific overexpression of 11βHSD1 under the control of the aP2 promoter in mouse produces a phenotype remarkably reminiscent of human metabolic syndrome (Masuzaki et al. (2001) *Science* 294: 2166-2170; Masuzaki et al. (2003) *J. Clinical Invest.* 112: 83-90). Importantly, this phenotype occurs without an increase in total circulating corticosterone, but rather is driven by a local production of corticosterone within the adipose depots. The increased activity of 11βHSD1 in these mice (2-3 fold) is very similar to that observed in human obesity (Rask et al. (2001) *J. Clin. Endocrinol. Metab.* 86: 1418-1421). This suggests that local 11βHSD1-mediated conversion of inert glucocorticoid to active glucocorticoid can have profound influences whole body insulin sensitivity.

Based on this data, it would be predicted that the loss of 11βHSD1 would lead to an increase in insulin sensitivity and glucose tolerance due to a tissue-specific deficiency in active glucocorticoid levels. This is, in fact, the case as shown in studies with 11βHSD1-deficient mice produced by homologous recombination (Kotelevstev et al. (1997) *Proc. Natl. Acad. Sci.* 94: 14924-14929; Morton et al. (2001) *J. Biol. Chem.* 276: 41293-41300; Morton et al. (2004) *Diabetes* 53: 931-938). These mice are completely devoid of 11-keto reductase activity, confirming that 11βHSD1 encodes the only activity capable of generating active corticosterone from inert 11-dehydrocorticosterone. 11βHSD1-deficient mice are resistant to diet- and stress-induced hyperglycemia, exhibit attenuated induction of hepatic gluconeogenic enzymes (PEPCK, G6P), show increased insulin sensitivity within adipose, and have an improved lipid profile (decreased triglycerides and increased cardio-protective HDL). Additionally, these animals show resistance to high fat diet-induced obesity. Further, adipose-tissue overexpression of the 11-beta dehydrogenase enzyme, 11bHSD2, which inactivates intracellular corticosterone to 11-dehydrocorticosterone, similarly attenuates weight gain on high fat diet, improves glucose tolerance, and heightens insulin sensitivity. Taken together, these transgenic mouse studies confirm a role for local reactivation of glucocorticoids in controlling hepatic and peripheral insulin sensitivity, and suggest that inhibition of 11βHSD1 activity may prove beneficial in treating a number of glucocorticoid-related disorders, including obesity, insulin resistance, hyperglycemia, and hyperlipidemia.

Data in support of this hypothesis has been published. Recently, it was reported that 11βHSD1 plays a role in the pathogenesis of central obesity and the appearance of the metabolic syndrome in humans. Increased expression of the 11βHSD1 gene is associated with metabolic abnormalities in obese women and that increased expression of this gene is suspected to contribute to the increased local conversion of cortisone to cortisol in adipose tissue of obese individuals (Engeli, et al., (2004) *Obes. Res.* 12: 9-17).

A new class of 11βHSD1 inhibitors, the arylsulfonamidothiazoles, was shown to improve hepatic insulin sensitivity and reduce blood glucose levels in hyperglycemic strains of mice (Barf et al. (2002) *J. Med. Chem.* 45: 3813-3815; Alberts et al. *Endocrinology* (2003) 144: 4755-4762). Additionally, it was recently reported that these selective inhibitors of 11βHSD1 can ameliorate severe hyperglycemia in genetically diabetic obese mice. Data using a structurally distinct series of compounds, the adamantyl triazoles (Hermanowski-Vosatka et al. (2005) *J. Exp. Med.* 202: 517-527), also indicates efficacy in rodent models of insulin resistance and diabetes, and further illustrates efficacy in a mouse model of atherosclerosis, perhaps suggesting local effects of corticosterone in the rodent vessel wall. Thus, 11βHSD1 is a promising pharmaceutical target for the treatment of the Metabolic Syndrome (Masuzaki, et al., (2003) *Curr. Drug Targets Immune Endocr. Metabol. Disord.* 3: 255-62).

A. Obesity and Metabolic Syndrome

As described above, multiple lines of evidence suggest that inhibition of 11βHSD1 activity can be effective in combating obesity and/or aspects of the metabolic syndrome cluster, including glucose intolerance, insulin resistance, hyperglycemia, hypertension, hyperlipidemia, and/or atherosclerosis/coronary heart disease. Glucocorticoids are known antagonists of insulin action, and reductions in local glucocorticoid levels by inhibition of intracellular cortisone to cortisol conversion should increase hepatic and/or peripheral insulin sensitivity and potentially reduce visceral adiposity. As described above, 11βHSD1 knockout mice are resistant to hyperglycemia, exhibit attenuated induction of key hepatic gluconeogenic enzymes, show markedly increased insulin sensitivity within adipose, and have an improved lipid profile. Additionally, these animals show resistance to high fat diet-induced obesity (Kotelevstev et al. (1997) *Proc. Natl. Acad. Sci.* 94: 14924-14929; Morton et al. (2001) *J. Biol. Chem.* 276: 41293-41300; Morton et al. (2004) *Diabetes* 53: 931-938). In vivo pharmacology studies with multiple chemical scaffolds have confirmed the critical role for 11bHSD1 in regulating insulin resistance, glucose intolerance, dyslipidemia, hypertension, and atherosclerosis. Thus, inhibition of 11βHSD1 is predicted to have multiple beneficial effects in the liver, adipose, skeletal muscle, and heart, particularly related to alleviation of component(s) of the metabolic syndrome, obesity, and/or coronary heart disease.

B. Pancreatic Function

Glucocorticoids are known to inhibit the glucose-stimulated secretion of insulin from pancreatic beta-cells (Billaudel and Sutter (1979) *Horm. Metab. Res.* 11: 555-560). In both Cushing's syndrome and diabetic Zucker fa/fa rats, glucose-stimulated insulin secretion is markedly reduced (Ogawa et al. (1992) *J. Clin. Invest.* 90: 497-504). 11βHSD1 mRNA and activity has been reported in the pancreatic islet cells of ob/ob mice and inhibition of this activity with carbenoxolone, an 11βHSD1 inhibitor, improves glucose-stimulated insulin release (Davani et al. (2000) *J. Biol. Chem.* 275: 34841-34844). Thus, inhibition of 11βHSD1 is predicted to have beneficial effects on the pancreas, including the enhancement of glucose-stimulated insulin release and the potential for attenuating pancreatic beta-cell decompensation.

C. Cognition and Dementia

Mild cognitive impairment is a common feature of aging that may be ultimately related to the progression of dementia. In both aged animals and humans, inter-individual differences in general cognitive function have been linked to variability in the long-term exposure to glucocorticoids (Lupien et al. (1998) *Nat. Neurosci.* 1: 69-73). Further, dysregulation of the HPA axis resulting in chronic exposure to glucocorticoid excess in certain brain subregions has been proposed to contribute to the decline of cognitive function (McEwen and Sapolsky (1995) *Curr. Opin. Neurobiol.* 5: 205-216). 11βHSD1 is abundant in the brain, and is expressed in multiple subregions including the hippocampus, frontal cortex, and cerebellum (Sandeep et al. (2004) *Proc. Natl. Acad. Sci.* Early Edition: 1-6). Treatment of primary hippocampal cells with the 11βHSD1 inhibitor carbenoxolone protects the cells from glucocorticoid-mediated exacerbation of excitatory amino acid neurotoxicity (Rajan et al. (1996) *J. Neurosci.* 16: 65-70). Additionally, 11βHSD1-deficient mice are protected from glucocorticoid-associated hippocampal dysfunction that is associated with aging (Yau et al. (2001) *Proc. Natl. Acad. Sci.* 98: 4716-4721). In two randomized, double-blind, placebo-controlled crossover studies, administration of carbenoxolone improved verbal fluency and verbal memory (Sandeep et al. (2004) *Proc. Natl. Acad. Sci. Early Edition:* 1-6). Thus, inhibition of 11βHSD1 is predicted to reduce exposure to glucocorticoids in the brain and protect against deleterious glucocorticoid effects on neuronal function, including cognitive impairment, dementia, and/or depression.

D. Intra-Ocular Pressure

Glucocorticoids can be used topically and systemically for a wide range of conditions in clinical ophthalmology. One particular complication with these treatment regimens is corticosteroid-induced glaucoma. This pathology is characterized by a significant increase in intra-ocular pressure (IOP). In its most advanced and untreated form, IOP can lead to partial visual field loss and eventually blindness. IOP is produced by the relationship between aqueous humour production and drainage. Aqueous humour production occurs in the non-pigmented epithelial cells (NPE) and its drainage is through the cells of the trabecular meshwork. 11βHSD1 has been localized to NPE cells (Stokes et al. (2000) *Invest. Ophthalmol. Vis. Sci.* 41: 1629-1683; Rauz et al. (2001) *Invest. Ophthalmol. Vis. Sci.* 42: 2037-2042) and its function is likely relevant to the amplification of glucocorticoid activity within these cells. This notion has been confirmed by the observation that free cortisol concentration greatly exceeds that of cortisone in the aqueous humour (14:1 ratio). The functional significance of 11βHSD1 in the eye has been evaluated using the inhibitor carbenoxolone in healthy volunteers (Rauz et al. (2001) *Invest. Ophthalmol. Vis. Sci.* 42: 2037-2042). After seven days of carbenoxolone treatment, IOP was reduced by 18%. Thus, inhibition of 11βHSD1 in the eye is predicted to reduce local glucocorticoid concentrations and IOP, producing beneficial effects in the management of glaucoma and other visual disorders.

E. Hypertension

Adipocyte-derived hypertensive substances such as leptin and angiotensinogen have been proposed to be involved in the pathogenesis of obesity-related hypertension (Matsuzawa et al. (1999) *Ann. N.Y. Acad. Sci.* 892: 146-154; Wajchenberg (2000) *Endocr. Rev.* 21: 697-738). Leptin, which is secreted in excess in aP2-11βHSD1 transgenic mice (Masuzaki et al. (2003) *J. Clinical Invest.* 112: 83-90), can activate various sympathetic nervous system pathways, including those that regulate blood pressure (Matsuzawa et al. (1999) *Ann. N.Y. Acad. Sci.* 892: 146-154). Additionally, the renin-angiotensin system (RAS) has been shown to be a major determinant of blood pressure (Walker et al. (1979) *Hypertension* 1: 287-291). Angiotensinogen, which is produced in liver and adipose tissue, is the key substrate for renin and drives RAS activation. Plasma angiotensinogen levels are markedly elevated in aP2-11βHSD1 transgenic mice, as are angiotensin II and aldosterone (Masuzaki et al. (2003) *J. Clinical Invest.* 112: 83-90). These forces likely drive the elevated blood pressure observed in aP2-11βHSD1 transgenic mice. Treatment of these mice with low doses of an angiotensin II receptor antagonist abolishes this hypertension (Masuzaki et al. (2003) *J. Clinical Invest.* 112: 83-90). This data illustrates the importance of local glucocorticoid reactivation in adipose tissue and liver, and suggests that hypertension may be caused or exacerbated by 11βHSD1 activity. Thus, inhibition of 11βHSD1 and reduction in adipose and/or hepatic glucocorticoid levels is predicted to have beneficial effects on hypertension and hypertension-related cardiovascular disorders.

F. Bone Disease

Glucocorticoids can have adverse effects on skeletal tissues. Continued exposure to even moderate glucocorticoid doses can result in osteoporosis (Cannalis (1996) *J. Clin. Endocrinol. Metab.* 81: 3441-3447) and increased risk for fractures. Experiments in vitro confirm the deleterious effects of glucocorticoids on both bone-resorbing cells (also known as osteoclasts) and bone forming cells (osteoblasts). 11βHSD1 has been shown to be present in cultures of human primary osteoblasts as well as cells from adult bone, likely a mixture of osteoclasts and osteoblasts (Cooper et al. (2000) *Bone* 27: 375-381), and the 11βHSD1 inhibitor carbenoxolone has been shown to attenuate the negative effects of glucocorticoids on bone nodule formation (Bellows et al. (1998) *Bone* 23: 119-125). Thus, inhibition of 11βHSD1 is predicted to decrease the local glucocorticoid concentration within osteoblasts and osteoclasts, producing beneficial effects in various forms of bone disease, including osteoporosis.

Small molecule inhibitors of 11βHSD1 are currently being developed to treat or prevent 11βHSD1-related diseases such as those described above. For example, certain amide-based inhibitors are reported in WO 2004/089470, WO 2004/089896, WO 2004/056745, and WO 2004/065351. Other amide-based inhibitors are reported in US. Pub. Nos. 2005/0282858, 2005/0288317, 2005/0288329, 2005/0288338, and 2006/0004049. Antagonists of 11βHSD1 have also been evaluated in human clinical trials (Kurukulasuriya, et al., (2003) *Curr. Med. Chem.* 10: 123-53).

In light of the experimental data indicating a role for 11βHSD1 in glucocorticoid-related disorders, metabolic syndrome, hypertension, obesity, insulin resistance, hyperglycemia, hyperlipidemia, type 2 diabetes, atherosclerosis, androgen excess (hirsutism, menstrual irregularity, hyperandrogenism) and polycystic ovary syndrome (PCOS), therapeutic agents aimed at augmentation or suppression of these metabolic pathways, by modulating glucocorticoid signal transduction at the level of 11βHSD1 are desirable.

Furthermore, because the MR binds to aldosterone (its natural ligand) and cortisol with equal affinities, compounds that are designed to interact with the active site of 11βHSD1 (which binds to cortisone/cortisol) may also interact with the MR and act as antagonists. Because the MR is implicated in heart failure, hypertension, and related pathologies including atherosclerosis, arteriosclerosis, coronary artery disease, thrombosis, angina, peripheral vascular disease, vascular wall damage, and stroke, MR antagonists are desirable and may also be useful in treating complex cardiovascular, renal, and inflammatory pathologies including disorders of lipid metabolism including dyslipidemia or hyperlipoproteinaemia, diabetic dyslipidemia, mixed dyslipidemia, hypercholesterolemia, hypertriglyceridemia, as well as those associated with type 1 diabetes, type 2 diabetes, obesity, metabolic syndrome, and insulin resistance, and general aldosterone-related target-organ damage.

As evidenced herein, there is a continuing need for new and improved drugs that target 11βHSD1. The compounds, compositions and methods described herein help meet this and other needs.

SUMMARY

The present invention provides compounds of Formula I:

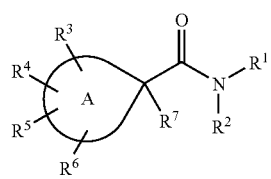

or pharmaceutically acceptable salts or prodrugs thereof, wherein constituent members are provided herein.

The present invention further provides compositions comprising a compound of the invention, or pharmaceutically acceptable salt thereof, and at least one pharmaceutically acceptable carrier.

The present invention further provides methods of modulating 11βHSD1 by contacting 11βHSD1 with a compound of the invention, or pharmaceutically acceptable salt thereof.

The present invention further provides methods of inhibiting 11βHSD1 by contacting 11βHSD1 with a compound of the invention, or pharmaceutically acceptable salt thereof.

The present invention further provides methods of inhibiting the conversion of cortisone to cortisol in a cell by contacting the cell with a compound of the invention, or pharmaceutically acceptable salt thereof.

The present invention further provides methods of inhibiting the production of cortisol in a cell by contacting the cell with a compound of the invention, or pharmaceutically acceptable salt thereof.

The present invention further provides methods of treating diseases associated with activity or expression of 11βHSD1.

The details of one or more embodiments of the invention are set forth in the accompanying drawings and the description below. Other features, objects, and advantages of the invention will be apparent from the description and drawings, and from the claims.

DETAILED DESCRIPTION

The present invention provides compounds which modulate activity of 11βHSD1 having Formula I:

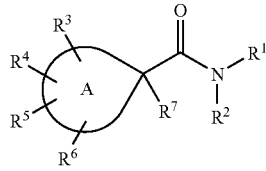

I or pharmaceutically acceptable salt or prodrug thereof, wherein:

ring A is a 4-10 membered heterocycloalkyl ring comprising at least one ring-forming N atom which is substituted by $R^N$;

$R^N$ is H, $C_{1-6}$ alkyl, $C_{2-6}$ alkenyl, $C_{2-6}$ alkynyl, —C(O)—$R^{8a}$, —C(O)O—$R^{8b}$, —SO$_q$—$R^{8a}$, —(CR$^{1a}$R$^{1b}$)$_a$-Cy$^1$, or —(CR$^{1a}$R$^{1b}$)$_a$—C(O)—(CR$^{1a}$R$^{1b}$)$_b$-Cy$^1$, wherein said $C_{1-6}$ alkyl, $C_{2-6}$ alkenyl, or $C_{2-6}$ alkynyl is optionally substituted by 1, 2, 3, 4, or 5 substituents independently selected from halo, $C_{1-4}$ alkyl, $C_{1-4}$ haloalkyl, aryl, cycloalkyl, heteroaryl, heterocycloalkyl, arylalkyl, cycloalkylalkyl, heteroarylalkyl, heterocycloalkylalkyl, halosulfanyl, CN, N$_3$, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{d1}$, NR$^{c1}$C(O)OR$^{a1}$, S(O)R$^{b1}$, S(O)NR$^{c1}$R$^{d1}$, S(O)$_2$R$^{b1}$, and S(O)$_2$NR$^{c1}$R$^{d1}$;

$R^1$ is $C_{1-6}$ alkyl, $C_{2-12}$ alkoxyalkyl, or —(CR$^{2a}$R$^{2b}$)$_c$-Cy$^2$;

$R^2$ is H or $C_{1-6}$ alkyl;

or $R^2$ together with $R^7$ form a linking moiety of formula —(CR$^{3a}$R$^{3b}$)$_{n1}$—, —(CR$^{3a}$R$^{3b}$)$_{n2}$CO—, —(CR$^{3a}$R$^{3b}$)$_{n2}$CO(CR$^{3a}$R$^{3b}$)$_{n2}$—, —(CR$^{3a}$R$^{3b}$)$_{n2}$OCO—, —(CR$^{3a}$R$^{3b}$)$_{n2}$SO—, —(CR$^{3a}$R$^{3b}$)$_{n2}$SO$_2$—, —(CR$^{3a}$R$^{3b}$)$_{n2}$NR$^{3c}$—, —(CR$^{3a}$R$^{3b}$)$_{n3}$CONR$^{3c}$—, —(CR$^{3a}$R$^{3b}$)$_{n2}$NR$^{3c}$CO—, or a group of formula:

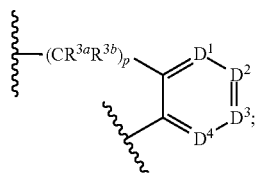

$R^3$, $R^4$, $R^5$, and $R^6$ are independently selected from H, halo, $C_{1-4}$ alkyl, $C_{1-4}$ haloalkyl, $C_{2-6}$ alkenyl, $C_{2-6}$ alkynyl, —(CR$^{1a}$R$^{1b}$)$_a$-Cy$^4$, halosulfanyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^d$, NR$^c$C(O)OR$^a$, S(O)R$^b$, S(O)NR$^c$R$^d$, S(O)$_2$R$^b$, and S(O)$_2$NR$^c$R$^d$, wherein said $C_{1-4}$ alkyl, $C_{2-6}$ alkenyl, or $C_{2-6}$ alkynyl are optionally substituted with 1, 2 or 3 substituents selected from halo, halosulfanyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^d$, NR$^c$C(O)OR$^a$, S(O)R$^b$, S(O)NR$^c$R$^d$, S(O)$_2$R$^b$, and S(O)$_2$NR$^c$R$^d$;

or two of $R^3$, $R^4$, $R^5$, and $R^6$ are attached to the same atom of ring A and together with the atom to which they are attached form a 3-20 membered cycloalkyl group or 3-20 membered heterocycloalkyl group, each optionally substituted by 1, 2, or 3 substituents independently selected from halo, $C_{1-4}$ alkyl, $C_{1-4}$ haloalkyl, aryl, cycloalkyl, heteroaryl, heterocycloalkyl, halosulfanyl, CN, NO$_2$, OR$^1$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^d$, NR$^c$C(O)OR$^a$, S(O)R$^b$, S(O)NR$^c$R$^d$, S(O)$_2$R$^b$, and S(O)$_2$NR$^c$R$^d$;

$R^7$ is H or $C_{1-6}$ alkyl;

$R^{8a}$ is H, $C_{1-6}$ alkyl, NR$^{c1}$R$^{d1}$, or Cy$^3$, wherein said $C_{1-6}$ alkyl is optionally substituted by 1, 2, 3, 4 or 5 substituents independently selected from halo, $C_{1-4}$ alkyl, $C_{1-4}$ haloalkyl, aryl, cycloalkyl, heteroaryl, heterocycloalkyl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{d1}$, NR$^{c1}$C(O)OR$^{a1}$, S(O)R$^{b1}$, S(O)NR$^{c1}$R$^{d1}$, S(O)$_2$R$^{b1}$, and S(O)$_2$NR$^{c1}$R$^{d1}$;

$R^{8b}$ is H, $C_{1-6}$ alkyl, or Cy$^3$, wherein said $C_{1-6}$ alkyl is optionally substituted by 1, 2, 3, 4 or 5 substituents independently selected from halo, $C_{1-4}$ alkyl, $C_{1-4}$ haloalkyl, aryl, cycloalkyl, heteroaryl, heterocycloalkyl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{d1}$, NR$^{c1}$C(O)OR$^{a1}$, S(O)R$^{b1}$, S(O)NR$^{c1}$R$^{d1}$, S(O)$_2$R$^{b1}$ and S(O)$_2$NR$^{c1}$R$^{d1}$;

$D^1$, $D^2$, $D^3$ and $D^4$ are independently selected from N and CR$^D$;

$R^D$ is H, halo, $C_{1-4}$ alkyl, $C_{1-4}$ haloalkyl, aryl, cycloalkyl, heteroaryl, heterocycloalkyl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{d2}$, NR$^{c2}$C(O)OR$^{a2}$, S(O)R$^{b2}$, S(O)NR$^{c2}$R$^{d2}$, S(O)$_2$R$^{b2}$, or S(O)$_2$NR$^{c2}$R$^{d2}$;

Cy$^1$, Cy$^2$, Cy$^3$, and Cy$^4$ are independently selected from aryl, heteroaryl, cycloalkyl, and heterocycloalkyl, each optionally substituted by 1, 2, 3, 4 or 5 substituents independently selected from Cy$^5$, halo, $C_{1-4}$ alkyl, $C_{2-4}$ alkenyl, $C_{2-4}$ alkynyl, $C_{1-4}$ haloalkyl, halosulfanyl, CN, NO$_2$, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)OR$^{a3}$, S(O)R$^{b3}$, S(O)NR$^{c3}$R$^{d3}$, S(O)$_2$R$^{b3}$, and S(O)$_2$NR$^{c3}$R$^{d3}$;

Cy$^5$ is aryl, heteroaryl, cycloalkyl, and heterocycloalkyl, each optionally substituted by 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, halosulfanyl, CN, NO$_2$, OR$^{a6}$, SR$^{a6}$, C(O)R$^{b6}$, C(O)NR$^{c6}$R$^{d6}$, C(O)OR$^{a6}$, OC(O)R$^{b6}$, OC(O)NR$^{c6}$R$^{d6}$, NR$^{c6}$R$^{d6}$, NR$^{c6}$C(O)R$^{b6}$, NR$^{c6}$C(O)OR$^{a6}$, S(O)R$^{b6}$, S(O)NR$^{c6}$R$^{d6}$, S(O)$_2$R$^{b6}$, and S(O)$_2$NR$^{c6}$R$^{d6}$;

$R^{1a}$ and $R^{1b}$ are independently selected from H, halo, $C_{1-4}$ alkyl, $C_{2-4}$ alkenyl, $C_{2-4}$ alkynyl, $C_{1-4}$ alkoxy, $C_{1-4}$ haloalkyl, $C_{1-4}$ haloalkoxy, OH, amino, $C_{1-4}$ alkylamino, and $C_{2-8}$ dialkylamino;

$R^{2a}$ and $R^{2b}$ are independently selected from halo, $C_{1-4}$ alkyl, $C_{2-4}$ alkenyl, $C_{2-4}$ alkynyl, $C_{1-4}$ alkoxy, $C_{1-4}$ haloalkyl, $C_{1-4}$ haloalkoxy, OH, amino, $C_{1-4}$ alkylamino, and $C_{2-8}$ dialkylamino;

$R^{3a}$ and $R^{3b}$ are independently selected from H, $OC(O)R^{a4}$, $OC(O)OR^{b4}$, $C(O)OR^{b4}$, $OC(O)NR^{c4}R^{d4}$, $NR^{c4}R^{d4}$, $NR^{c4}C(O)R^{a4}$, $NR^{c4}C(O)OR^{b4}$, $S(O)R^{a4}$, $S(O)NR^{c4}R^{d4}$, $S(O)_2R^{a4}$, $S(O)_2NR^{c4}R^{d4}$, $OR^{b4}$, $SR^{b4}$, halo, $C_{1-10}$ alkyl, $C_{1-10}$ haloalkyl, $C_{2-10}$ alkenyl, $C_{2-10}$ alkynyl, aryl, cycloalkyl, heteroaryl, heterocycloalkyl, arylalkyl, heteroarylalkyl, cycloalkylalkyl and heterocycloalkylalkyl, wherein said $C_{1-10}$ alkyl, $C_{1-10}$ haloalkyl, $C_{2-10}$ alkenyl, $C_{2-10}$ alkynyl, aryl, cycloalkyl, heteroaryl, heterocycloalkyl, arylalkyl, heteroarylalkyl, cycloalkylalkyl or heterocycloalkylalkyl is optionally substituted by 1, 2, or 3 $R^x$;

$R^{3c}$ is H, $C_{1-4}$ alkyl, $C_{1-4}$ haloalkyl, $C_{2-4}$ alkenyl, $C_{2-4}$ alkynyl, or $CO—(C_{1-4}$ alkyl);

$R^x$ is halo, $C_{1-4}$ alkyl, $C_{1-4}$ haloalkyl, aryl, cycloalkyl, heteroaryl, heterocycloalkyl, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{d5}$, $NR^{c5}C(O)OR^{a5}$, $S(O)R^{b5}$, $S(O)NR^{c5}R^{d5}$, $S(O)_2R^{b5}$, or $S(O)_2NR^{c5}R^{d5}$;

$R^a$, $R^{a1}$, $R^{a2}$, $R^{a3}$, $R^{a4}$ and $R^{a5}$ are independently selected from H, $C_{1-6}$ alkyl, $C_{1-6}$ haloalkyl, $C_{2-6}$ alkenyl, $C_{2-6}$ alkynyl, $Cy^5$, and $—(C_{1-6}$ alkyl)-$Cy^5$, wherein said $C_{1-6}$ alkyl, $C_{1-6}$ haloalkyl, $C_{2-6}$ alkenyl, or $C_{2-6}$ alkynyl is optionally substituted with 1, 2, or 3 substituents independently selected from OH, CN, amino, halo, $C_{1-6}$ alkyl, $C_{1-6}$ haloalkyl, aryl, arylalkyl, heteroaryl, heteroarylalkyl, cycloalkyl and heterocycloalkyl;

$R^b$, $R^{b1}$, $R^{b2}$, $R^{b3}$, $R^{b4}$, and $R^{b5}$ are independently selected from H, $C_{1-6}$ alkyl, $C_{1-6}$ haloalkyl, $C_{2-6}$ alkenyl, $C_{2-6}$ alkynyl, $Cy^5$, and $—(C_{1-6}$ alkyl)-$Cy^5$, wherein said $C_{1-6}$ alkyl, $C_{1-6}$ haloalkyl, $C_{2-6}$ alkenyl, or $C_{2-6}$ alkynyl is optionally substituted with 1, 2, or 3 substituents independently selected from OH, CN, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl and heterocycloalkyl;

$R^c$, $R^{c1}$, $R^{c2}$, $R^{c3}$, $R^{c4}$, $R^{c5}$, $R^d$, $R^{d1}$, $R^{d2}$, $R^{d3}$, $R^{d4}$, and $R^{d5}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl and heterocycloalkyl;

or $R^c$ and $R^d$ together with the N atom to which they are attached form a 4-, 5-, 6- or 7-membered heterocycloalkyl group optionally substituted with 1, 2, or 3 substituents independently selected from OH, CN, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl or heterocycloalkyl;

or $R^{c1}$ and $R^{d1}$ together with the N atom to which they are attached form a 4-, 5-, 6- or 7-membered heterocycloalkyl group optionally substituted with 1, 2, or 3 substituents independently selected from OH, CN, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl and heterocycloalkyl;

or $R^{c2}$ and $R^{d2}$ together with the N atom to which they are attached form a 4-, 5-, 6- or 7-membered heterocycloalkyl group optionally substituted with 1, 2, or 3 substituents independently selected from OH, CN, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl and heterocycloalkyl;

or $R^{c3}$ and $R^{d3}$ together with the N atom to which they are attached form a 4-, 5-, 6- or 7-membered heterocycloalkyl group optionally substituted with 1, 2, or 3 substituents independently selected from OH, CN, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl and heterocycloalkyl;

or $R^{c4}$ and $R^{d4}$ together with the N atom to which they are attached form a 4-, 5-, 6- or 7-membered heterocycloalkyl group optionally substituted with 1, 2, or 3 substituents independently selected from OH, CN, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl and heterocycloalkyl;

or $R^{c5}$ and $R^{d5}$ together with the N atom to which they are attached form a 4-, 5-, 6- or 7-membered heterocycloalkyl group optionally substituted with 1, 2, or 3 substituents independently selected from OH, CN, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl and heterocycloalkyl;

$R^{a6}$ is H, $C_{1-6}$ alkyl, $C_{1-6}$ haloalkyl, $C_{2-6}$ alkenyl, or $C_{2-6}$ alkynyl, wherein said $C_{1-6}$ alkyl, $C_{1-6}$ haloalkyl, $C_{2-6}$ alkenyl, or $C_{2-6}$ alkynyl is optionally substituted with 1, 2, or 3 substituents independently selected from OH, CN, amino, halo, $C_{1-6}$ alkyl, $C_{1-6}$ haloalkyl, aryl, arylalkyl, heteroaryl, heteroarylalkyl, cycloalkyl and heterocycloalkyl;

$R^{b6}$ is H, $C_{1-6}$ alkyl, $C_{1-6}$ haloalkyl, $C_{2-6}$ alkenyl, or $C_{2-6}$ alkynyl, wherein said $C_{1-6}$ alkyl, $C_{1-6}$ haloalkyl, $C_{2-6}$ alkenyl, or $C_{2-6}$ alkynyl is optionally substituted with 1, 2, or 3 substituents independently selected from OH, CN, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl and heterocycloalkyl;

$R^{c6}$ and $R^{d5}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl and heterocycloalkyl;

or $R^{c6}$ and $R^{d6}$ together with the N atom to which they are attached form a 4-, 5-, 6- or 7-membered heterocycloalkyl group optionally substituted with 1, 2, or 3 substituents independently selected from OH, CN, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl or heterocycloalkyl;

a, b, and c are independently selected from 0, 1, 2, 3, 4, and 5;

n1 is 1, 2, 3 or 4;
n2 is 0, 1, 2, 3 or 4;
n3 is 0, 1, 2, 3 or 4;
p is 0, 1, or 2; and
q is 0, 1, or 2.

In some embodiments:
when $R^2$ is H or $C_{1-6}$ alkyl, then two of $R^3$, $R^4$, $R^5$, and $R^6$ are attached to the same atom of ring A and together with the atom to which they are attached form a 3-20 membered cycloalkyl group or 3-20 membered heterocycloalkyl group, each optionally substituted by 1, 2, or 3 substituents independently selected from halo, $C_{1-4}$ alkyl, $C_{1-4}$ haloalkyl, aryl, cycloalkyl, heteroaryl, heterocycloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^d$, NR$^c$C(O)OR$^a$, S(O)R$^b$, S(O)NR$^c$R$^d$, S(O)$_2$R$^b$, and S(O)$_2$NR$^c$R$^d$; and when R$^3$, R$^4$, R$^5$, and R$^6$ are independently selected from H, halo, C$_{1-4}$ alkyl, C$_{1-4}$ haloalkyl, C$_{2-6}$ alkenyl, C$_{2-6}$ alkynyl, —(CR$^{1a}$R$^{1b}$)$_a$-Cy$^4$, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^d$, NR$^c$C(O)OR$^a$, S(O)R$^b$, S(O)NR$^c$R$^d$, S(O)$_2$R$^b$, and S(O)$_2$NR$^c$R$^d$; then R$^2$ together with R$^7$ form a linking moiety of formula —(CR$^{3a}$R$^{3b}$)$_{n1}$—, —(CR$^{3a}$R$^{3b}$)$_{n2}$CO—, —(CR$^{3a}$R$^{3b}$)$_{n2}$CO(CR$^{3a}$R$^{3b}$)$_{n2}$—, —(CR$^{3a}$R$^{3b}$)$_{n2}$OCO—, —(CR$^{3a}$R$^{3b}$)$_{n2}$SO—, —(CR$^{3a}$R$^{3b}$)$_{n2}$SO$_2$—, —(CR$^{3a}$R$^{3b}$)$_{n2}$NR$^{3c}$—, —(CR$^{3a}$R$^{3b}$)$_{n3}$CONR$^{3c}$—, —(CR$^{3a}$R$^{3b}$)$_{n2}$NR$^{3c}$CO—, or a group of formula:

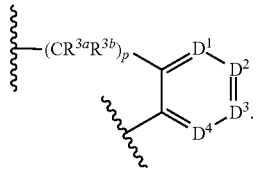

In some embodiments, ring A is a 5-, 6-, or 7-membered heterocycloalkyl ring comprising at least one ring-forming N atom which is substituted by R$^N$.

In some embodiments, ring A is a 5-membered heterocycloalkyl ring comprising at least one ring-forming N atom which is substituted by R$^N$.

In some embodiments, ring A is a pyrrolidine, piperidine, or azepine ring wherein the ring-forming N atom which is substituted by R$^N$.

In some embodiments, ring A is other than a piperidine ring where R$^7$ is attached to the 3-position.

In some embodiments, ring A is other than a piperidine ring where R$^7$ is attached to the 4-position.

In some embodiments, ring A is other than a pyrrolidine ring where R$^7$ is attached to the 3-position.

In some embodiments, R$^N$ is H, C$_{1-6}$ alkyl, C$_{2-6}$ alkenyl, C$_{2-6}$ alkynyl, —C(O)—R$^{8a}$, —C(O)O—R$^{8b}$, —SO$_q$—R$^{8a}$, —(CR$^{1a}$R$^{1b}$)$_a$-Cy$^1$, or —(CR$^{1a}$R$^{1b}$)$_a$—C(O)—(CR$^{1a}$R$^{1b}$)$_b$-Cy$^1$, wherein said C$_{1-6}$ alkyl, C$_{2-6}$ alkenyl, or C$_{2-6}$ alkynyl is optionally substituted by 1, 2, 3, 4, or 5 substituents independently selected from halo, C$_{1-4}$ alkyl, C$_{1-4}$ haloalkyl, aryl, cycloalkyl, heteroaryl, heterocycloalkyl, arylalkyl, cycloalkylalkyl, heteroarylalkyl, heterocycloalkylalkyl, CN, N$_3$, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{d1}$, NR$^{c1}$C(O)OR$^{a1}$, S(O)R$^{b1}$, S(O)NR$^{c1}$R$^{d1}$, S(O)$_2$R$^{b1}$, and S(O)$_2$NR$^{c1}$R$^{d1}$.

In some embodiments, R$^N$ is H, C$_{1-6}$ alkyl, C$_{2-6}$ alkenyl, C$_{2-6}$ alkynyl, —C(O)—R$^{8a}$, —C(O)O—R$^{8b}$, —SO$_q$—R$^{8a}$, —(CR$^{1a}$R$^{1b}$)$_a$-Cy$^1$, or —(CR$^{1a}$R$^{1b}$)$_a$—C(O)—(CR$^{1a}$R$^{1b}$)$_b$-Cy$^1$, wherein said C$_{1-6}$ alkyl, C$_{2-6}$ alkenyl, or C$_{2-6}$ alkynyl is optionally substituted by 1, 2, 3, 4, or 5 substituents independently selected from halo, C$_{1-4}$ alkyl, C$_{1-4}$ haloalkyl, aryl, cycloalkyl, heteroaryl, heterocycloalkyl, arylalkyl, cycloalkylalkyl, heteroarylalkyl, heterocycloalkylalkyl, CN, N$_3$, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{d1}$, NR$^{c1}$C(O)OR$^{a1}$, S(O)R$^{b1}$, S(O)NR$^{c1}$R$^{d1}$, S(O)$_2$R$^{b1}$, and S(O)$_2$NR$^{c1}$R$^{d1}$.

In some embodiments, R$^N$ is C$_{1-6}$ alkyl, C$_{2-6}$ alkenyl, C$_{2-6}$ alkynyl, —C(O)—R$^{8a}$, —C(O)O—R$^{8b}$, —SO$_q$—R$^{8a}$, —(CR$^{1a}$R$^{1b}$)$_a$-Cy$^1$, or —(CR$^{1a}$R$^{1b}$)$_a$—C(O)—(CR$^{1a}$R$^{1b}$)$_b$-Cy$^1$, wherein said C$_{1-6}$ alkyl, C$_{2-6}$ alkenyl, or C$_{2-6}$ alkynyl is optionally substituted by 1, 2, 3, 4, or 5 substituents independently selected from halo, C$_{1-4}$ alkyl, C$_{1-4}$ haloalkyl, aryl, cycloalkyl, heteroaryl, heterocycloalkyl, arylalkyl, cycloalkylalkyl, heteroarylalkyl, heterocycloalkylalkyl, CN, N$_3$, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{d1}$, NR$^{c1}$C(O)OR$^{a1}$, S(O)R$^{b1}$, S(O)NR$^{c1}$R$^{d1}$, S(O)$_2$R$^{b1}$, and S(O)$_2$NR$^{c1}$R$^{d1}$.

In some embodiments, R$^N$ is C$_{1-4}$ alkyl, cycloalkylalkyl, heterocycloalkylalkyl, arylalkyl, heteroarylalkyl, aryl, heteroaryl, arylsulfonyl, alkylsulfonyl, —C(O)O—(C$_{1-4}$ alkyl), —C(O)-aryl, —C(O)-heteroaryl, or —C(O)-cycloalkyl, each optionally substituted by 1, 2 or 3 substituents independently selected from halo, C$_{1-4}$ alkyl, C$_{1-4}$ haloalkyl, C$_{1-4}$ haloalkoxy, CN, and NO$_2$.

In some embodiments, R$^2$ is H.

In some embodiments, R$^2$ together with R$^7$ form a linking moiety of formula —(CR$^{3a}$R$^{3b}$)$_{n1}$—, —(CR$^{3a}$R$^{3b}$)$_{n2}$CO—, —(CR$^{3a}$R$^{3b}$)$_{n2}$CO(CR$^{3a}$R$^{3b}$)$_{n2}$—, —(CR$^{3a}$R$^{3b}$)$_{n2}$OCO—, —(CR$^{3a}$R$^{3b}$)$_{n2}$SO—, —(CR$^{3a}$R$^{3b}$)$_{n2}$SO$_2$—, —(CR$^{3a}$R$^{3b}$)$_{n2}$NR$^{3c}$—, —(CR$^{3a}$R$^{3b}$)$_{n3}$CONR$^{3c}$—, —(CR$^{3a}$R$^{3b}$)$_{n2}$NR$^{3c}$CO—, or a group of formula:

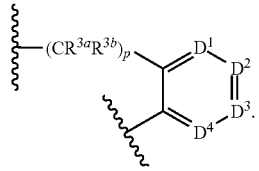

In some embodiments, R$^2$ together with R$^7$ form a linking moiety of formula —(CR$^{3a}$R$^{3b}$)$_{n1}$—.

In some embodiments, R$^2$ together with R$^7$ form —CH$_2$—CH$_2$—.

In some embodiments, R$^3$, R$^4$, R$^5$, and R$^6$ are independently selected from H, halo, C$_{1-4}$ alkyl, C$_{1-4}$ haloalkyl, C$_{2-6}$ alkenyl, C$_{2-6}$ alkynyl, —(CR$^{1a}$R$^{1b}$)$_a$Cy$^4$, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^d$, NR$^c$C(O)OR$^a$, S(O)R$^b$, S(O)NR$^c$R$^d$, S(O)$_2$R$^b$, and S(O)$_2$NR$^c$R$^d$, wherein said C$_{1-4}$ alkyl, C$_{2-6}$ alkenyl, or C$_{2-6}$ alkynyl are optionally substituted with 1, 2 or 3 substituents selected from halo, CN, NO$_2$, OR$^1$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^d$, NR$^c$C(O)OR$^a$, S(O)R$^b$, S(O)NR$^c$R$^d$, S(O)$_2$R$^b$, and S(O)$_2$NR$^c$R$^d$;

or two of R$^3$, R$^4$, R$^5$, and R$^6$ are attached to the same atom of ring A and together with the atom to which they are attached form a 3-20 membered cycloalkyl group or 3-20 membered heterocycloalkyl group, each optionally substituted by 1, 2, or 3 substituents independently selected from halo, C$_{1-4}$ alkyl, C$_{1-4}$ haloalkyl, aryl, cycloalkyl, heteroaryl, heterocycloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^d$, NR$^c$C(O)OR$^a$, S(O)R$^b$, S(O)NR$^c$R$^d$, S(O)$_2$R$^b$, and S(O)$_2$NR$^c$R$^d$.

In some embodiments, R$^3$, R$^4$, R$^5$, and R$^6$ are independently selected from H, halo, C$_{1-4}$ alkyl, C$_{1-4}$ haloalkyl, OR$^a$, or OC(O)R$^b$.

In some embodiments, R$^3$, R$^4$, R$^5$, and R$^6$ are independently selected from H, F, Me, or OH.

In some embodiments, R$^3$, R$^4$, R$^5$, and R$^6$ are each H.

In some embodiments, two of R$^3$, R$^4$, R$^5$, and R$^6$ are attached to the same atom of ring A and together with the atom to which they are attached form a 3-20 membered cycloalkyl group or 3-20 membered heterocycloalkyl group, each optionally substituted by 1, 2, or 3 substituents independently selected from halo, $C_{1-4}$ alkyl, $C_{1-4}$ haloalkyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^cC(O)OR^a$, $S(O)R^b$, $S(O)NR^cR^d$, $S(O)_2R^b$, and $S(O)_2NR^cR^d$.

In some embodiments, two of $R^3$, $R^4$, $R^5$, and $R^6$ are attached to the same atom of ring A and together with the atom to which they are attached form a 3-7 membered cycloalkyl group or 3-7 membered heterocycloalkyl group.

In some embodiments, two of $R^3$, $R^4$, $R^5$, and $R^6$ are attached to the same atom of ring A and together with the atom to which they are attached form a cyclopropyl group.

In some embodiments, $R^1$ is $C_{1-6}$ alkyl or $-(CR^{2a}R^{2b})_c$-$Cy^2$.

In some embodiments, $R^1$ is $-(CR^{2a}R^{2b})_c$-$Cy^2$.

In some embodiments, $R^1$ is aryl, heteroaryl, cycloalkyl, heterocycloalkyl, arylalkyl, heteroarylalkyl, cycloalkylalkyl, or heterocycloalkylalkyl each optionally substituted by 1, 2 or 3 substituents selected from halo, $C_{1-4}$ alkyl, $C_{1-4}$ haloalkyl, CN, $NO_2$, and $OR^{a3}$.

In some embodiments, $R^1$ is aryl, heteroaryl, cycloalkyl, heterocycloalkyl, arylalkyl, heteroarylalkyl, cycloalkylalkyl, or heterocycloalkylalkyl each optionally substituted by 1, 2 or 3 halo.

In some embodiments, $R^7$ is H.

In some embodiments, $Cy^1$, $Cy^2$, $Cy^3$, and $Cy^4$ are independently selected from aryl, heteroaryl, cycloalkyl, and heterocycloalkyl, each optionally substituted by 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $S(O)R^{b3}$, $S(O)NR^{c3}R^{d3}$, $S(O)_2R^{b3}$, and $S(O)_2NR^{c3}R^{d3}$.

In some embodiments, $Cy^2$ is aryl, heteroaryl, cycloalkyl, and heterocycloalkyl, each optionally substituted by 1 or 2 substituents independently selected from halo and $OR^{a3}$.

In some embodiments, $Cy^2$ is aryl, heteroaryl, cycloalkyl, and heterocycloalkyl, each optionally substituted by 1 or 2 substituents independently selected from methoxy, OH, and Cl.

In some embodiments, $Cy^2$ is cycloalkyl optionally substituted by 1 or 2 substituents independently selected from methoxy, OH, and Cl.

In some embodiments, $Cy^2$ is cyclohexyl optionally substituted by 1 or 2 substituents independently selected from methoxy and OH.

In some embodiments, $Cy^2$ is cyclohexyl.

In some embodiments, $R^{1a}$ and $R^{1b}$ are independently selected from halo, $C_{1-4}$ alkyl, $C_{2-4}$ alkenyl, $C_{2-4}$ alkynyl, $C_{1-4}$ alkoxy, $C_{1-4}$ haloalkyl, $C_{1-4}$ haloalkoxy, OH, amino, $C_{1-4}$ alkylamino, and $C_{2-8}$ dialkylamino and $R^{1a}$ and $R^{1b}$ together with the C atom to which they are attached form cycloalkyl or heterocycloalkyl group.

In some embodiments, $R^{1a}$ and $R^{1b}$ are independently selected from halo, $C_{1-4}$ alkyl, $C_{2-4}$ alkenyl, $C_{2-4}$ alkynyl, $C_{1-4}$ alkoxy, $C_{1-4}$ haloalkyl, $C_{1-4}$ haloalkoxy, OH, amino, $C_{1-4}$ alkylamino, and $C_{2-8}$ dialkylamino.

In some embodiments, $R^a$, $R^{a1}$, $R^{a2}$, $R^{a3}$, $R^{a4}$ and $R^{a5}$ are independently selected from H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, $C_{1-6}$ alkyl, $C_{1-6}$ haloalkyl, aryl, arylalkyl, heteroaryl, heteroarylalkyl, cycloalkyl and heterocycloalkyl.

In some embodiments, $R^b$, $R^{b1}$, $R^{b2}$, $R^{b3}$, $R^{b4}$, and $R^{b5}$ are independently selected from H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl and heterocycloalkyl.

In some embodiments, $R^{c2}$ and $R^{d2}$ are each, independently, H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl and heterocycloalkyl.

In some embodiments, a, b, and c are independently selected from 0, 1, and 2.

In some embodiments, a is 0.

In some embodiments, a is 1.

In some embodiments, b is 0.

In some embodiments, b is 1.

In some embodiments, c is 0.

In some embodiments, c is 1.

In some embodiments, n1 is 2.

In some embodiments, n2 is 0 or 1.

In some embodiments, n3 is 0 or 1.

In some embodiments, p is 0.

In some embodiments, p is 1.

In some embodiments, p is 2.

In some embodiments, q is 2.

In some embodiments, the compounds of the invention have Formula II:

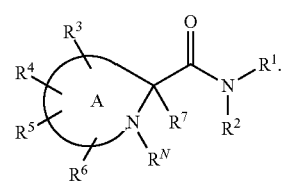

II

In some embodiments, the compounds of the invention have Formula III:

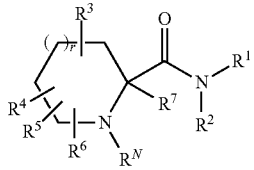

wherein r is 0, 1, or 2.

In some embodiments, r is 0.
In some embodiments, r is 1.
In some embodiments, r is 2.
In some embodiments, the compounds of the invention have Formula IV:

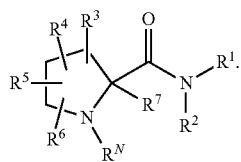

In some embodiments, the compounds of the invention have Formula Va:

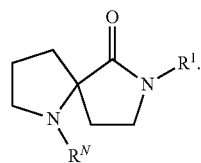

In some embodiments, the compounds of the invention have Formula Vb:

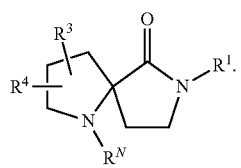

In some embodiments, the compounds of the invention have Formula VI:

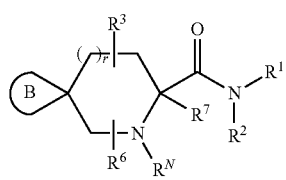

wherein:
wherein r is 0, 1, or 2; and
ring B is a 3-20 membered cycloalkyl group or 3-20 membered heterocycloalkyl group, each optionally substituted by 1, 2, or 3 substituents independently selected from halo, $C_{1-4}$ alkyl, $C_{1-4}$ haloalkyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^cC(O)OR^a$, $S(O)R^b$, $S(O)NR^cR^d$, $S(O)_2R^b$, and $S(O)_2NR^cR^d$.

In some embodiments, ring B is 3-7 membered cycloalkyl or 3-7 membered heterocycloalkyl.

In some embodiments, ring B is cyclopropyl.

In some embodiments, the compounds of the invention have Formula VII:

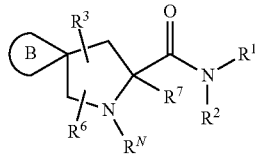

wherein ring B is a 3-20 membered cycloalkyl group or 3-20 membered heterocycloalkyl group, each optionally substituted by 1, 2, or 3 substituents independently selected from halo, $C_{1-4}$ alkyl, $C_{1-4}$ haloalkyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^cC(O)OR^a$, $S(O)R^b$, $S(O)NR^cR^d$, $S(O)_2R^b$, and $S(O)_2NR^cR^d$.

In some embodiments, ring B is 3-7 membered cycloalkyl or 3-7 membered heterocycloalkyl.

In some embodiments, ring B is cyclopropyl.

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

At various places in the present specification, linking substituents may be described. It is specifically intended that each linking substituent include both the forward and backward forms of the linking substituent. For example, —NR(CR'R")$_n$— includes both —NR(CR'R")$_n$— and —(CR'R")$_n$NR—. Where the structure clearly requires a linking group, the Markush variables listed for that group are understood to be linking groups. For example, if the structure requires a linking group and the Markush group definition for that variable lists "alkyl," then it is understood that the "alkyl" represents a linking alkylene group.

The term "n-membered" where n is an integer typically describes the number of ring-forming atoms in a moiety where the number of ring-forming atoms is n. For example, piperidinyl is an example of a 6-membered heterocycloalkyl ring and 1,2,3,4-tetrahydro-naphthalene is an example of a 10-membered cycloalkyl group.

As used herein, the term "alkyl" is meant to refer to a saturated hydrocarbon group which is straight-chained or branched. Example alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. An alkyl group can contain from 1 to about 20, from 2 to about 20, from 1 to about 10, from 1 to about 8, from 1 to about 6, from 1 to about 4, or from 1 to about 3 carbon atoms. The term "alkylenyl" refers to a divalent alkyl linking group.

As used herein, "alkenyl" refers to an alkyl group having one or more double carbon-carbon bonds. Example alkenyl groups include ethenyl, propenyl, cyclohexenyl, and the like. The term "alkenylenyl" refers to a divalent linking alkenyl group.

As used herein, "alkynyl" refers to an alkyl group having one or more triple carbon-carbon bonds. Example alkynyl groups include ethynyl, propynyl, and the like. The term "alkynylenyl" refers to a divalent linking alkynyl group.

As used herein, "haloalkyl" refers to an alkyl group having one or more halogen substituents. Example haloalkyl groups include $CF_3$, $C_2F_5$, $CHF_2$, $CCl_3$, $CHCl_2$, $C_2Cl_5$, and the like.

As used herein, "aryl" refers to monocyclic or polycyclic (e.g., having 2, 3 or 4 fused rings) aromatic hydrocarbons such as, for example, phenyl, naphthyl, anthracenyl, phenanthrenyl, indanyl, indenyl, and the like. In some embodiments, aryl groups have from 6 to about 20 carbon atoms.

As used herein, "cycloalkyl" refers to non-aromatic cyclic hydrocarbons including cyclized alkyl, alkenyl, and alkynyl groups. Cycloalkyl groups can include mono- or polycyclic (e.g., having 2, 3 or 4 fused rings) groups and spirocycles. Ring-forming carbon atoms of a cycloalkyl group can be optionally substituted by oxo or sulfido. Cycloalkyl groups also include cycloalkylidenes. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like. Also included in the definition of cycloalkyl are moieties that have one or more aromatic rings fused (i.e., having a bond in common with) to the cycloalkyl ring, for example, benzo or thienyl derivatives of pentane, pentene, hexane, and the like. A cycloalkyl group containing a fused aromatic ring can be attached through any ring-forming atom including a ring-forming atom of the fused aromatic ring. A linking cycloalkyl group is referred to herein as "cycloalkylene."

As used herein, "heteroaryl" refers to an aromatic heterocycle having at least one heteroatom ring member such as sulfur, oxygen, or nitrogen. Heteroaryl groups include monocyclic and polycyclic (e.g., having 2, 3 or 4 fused rings) systems. Examples of heteroaryl groups include without limitation, pyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like. In some embodiments, the heteroaryl group has from 1 to about 20 carbon atoms, and in further embodiments from about 3 to about 20 carbon atoms. In some embodiments, the heteroaryl group contains 3 to about 14, 4 to about 14, 3 to about 7, or 5 to 6 ring-forming atoms. In some embodiments, the heteroaryl group has 1 to about 4, 1 to about 3, or 1 to 2 heteroatoms.

As used herein, "heterocycloalkyl" refers to non-aromatic heterocycles wherein one or more of the ring-forming atoms is a heteroatom such as an O, N, or S atom. Heterocycloalkyl groups include monocyclic and polycyclic (e.g., having 2, 3 or 4 fused rings) systems as well as spirocycles. Example "heterocycloalkyl" groups include morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, isothiazolidinyl, pyrazolidinyl, oxazolidinyl, thiazolidinyl, imidazolidinyl, and the like. Ring-forming carbon atoms and heteroatoms of a heterocycloalkyl group can be optionally substituted by oxo or sulfido. Also included in the definition of heterocycloalkyl are moieties that have one or more aromatic rings fused (i.e., having a bond in common with) to the nonaromatic heterocyclic ring, for example phthalimidyl, naphthalimidyl, and benzo derivatives of heterocycles. The heterocycloalkyl group can be attached through a ring-forming carbon atom or a ring-forming heteroatom. The heterocycloalkyl group containing a fused aromatic ring can be attached through any ring-forming atom including a ring-forming atom of the fused aromatic ring. In some embodiments, the heterocycloalkyl group has from 1 to about 20 carbon atoms, and in further embodiments from about 3 to about 20 carbon atoms. In some embodiments, the heterocycloalkyl group contains 3 to about 14, 4 to about 14, 3 to about 7, or 5 to 6 ring-forming atoms. In some embodiments, the heterocycloalkyl group has 1 to about 4, 1 to about 3, or 1 to 2 heteroatoms. In some embodiments, the heterocycloalkyl group contains 0 to 3 double or triple bonds. In some embodiments, the heterocycloalkyl group contains 0 to 2 double or triple bonds. A linking heterocycloalkyl group is referred to herein as "heterocycloalkylene."

As used herein, "halo" includes fluoro, chloro, bromo, and iodo.

As used herein, "alkoxy" refers to an —O-alkyl group. Example alkoxy groups include methoxy, ethoxy, propoxy (e.g., n-propoxy and isopropoxy), t-butoxy, and the like.

As used herein, "alkoxyalkyl" refers to an alkyl group substituted by an alkoxy group.

As used here, "haloalkoxy" refers to an —O-haloalkyl group. An example haloalkoxy group is $OCF_3$.

As used herein, "arylalkyl" refers to alkyl substituted by aryl and "cycloalkylalkyl" refers to alkyl substituted by cycloalkyl. An example arylalkyl group is benzyl.

As used herein, "heteroarylalkyl" refers to alkyl substituted by heteroaryl and "heterocyclo-alkylalkyl" refers to alkyl substituted by heterocycloalkyl.

As used herein, "amino" refers to $NH_2$.

As used herein, "alkylamino" refers to an amino group substituted by an alkyl group.

As used herein, "dialkylamino" refers to an amino group substituted by two alkyl groups.

As used herein, "halosulfanyl" refers to a sulfur group having one or more halogen substituents. Example halosulfanyl groups include pentahalosulfanyl groups such as $SF_5$.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. An example method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methyl-benzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds of the invention also include all tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, amide-imidic acid pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the invention further include crystalline and non-crystalline solid forms, including hydrated, solvated, anyhydrous, and non-solvated forms.

Compounds of the invention can also include all isotopes of atoms occurring in the intermediates or final compounds. Isotopes include those atoms having the same atomic number but different mass numbers. For example, isotopes of hydrogen include tritium and deuterium.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues-such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in its entirety.

The present invention also includes prodrugs of the compounds described herein. As used herein, "prodrugs" refer to any covalently bonded carriers which release the active parent drug when administered to a mammalian subject. Prodrugs can be prepared by modifying functional groups present in the compounds in such a way that the modifications are cleaved, either in routine manipulation or in vivo, to the parent compounds. Prodrugs include compounds wherein hydroxyl, amino, sulfhydryl, or carboxyl groups are bonded to any group that, when administered to a mammalian subject, cleaves to form a free hydroxyl, amino, sulfhydryl, or carboxyl group respectively. Examples of prodrugs include, but are not limited to, acetate, formate and benzoate derivatives of alcohol and amine functional groups in the compounds of the invention. Preparation and use of prodrugs is discussed in T. Higuchi and V. Stella, "Pro-drugs as Novel Delivery Systems," Vol. 14 of the A.C.S. Symposium Series, and in *Bioreversible Carriers in Drug Design,* ed. Edward B. Roche, American Pharmaceutical Association and Pergamon Press, 1987, both of which are hereby incorporated by reference in their entirety.

Synthesis

The novel compounds of the present invention can be prepared in a variety of ways known to one skilled in the art of organic synthesis. The compounds of the present invention can be synthesized using the methods as hereinafter described below, together with synthetic methods known in the art of synthetic organic chemistry or variations thereon as appreciated by those skilled in the art.

The compounds of this invention can be prepared from readily available starting materials, for example, using the following general methods and procedures. It will be appreciated that where typical or preferred process conditions (i.e., reaction temperatures, times, mole ratios of reactants, solvents, pressures, etc.) are given; other process conditions can also be used unless otherwise stated. Optimum reaction conditions may vary with the particular reactants or solvent used, but such conditions can be determined by one skilled in the art by routine optimization procedures.

The processes described herein can be monitored according to any suitable method known in the art. For example, product formation can be monitored by spectroscopic means, such as nuclear magnetic resonance (NMR) spectroscopy (e.g., $^1$H or $^{13}$C) infrared (IR) spectroscopy, spectro-photometry (e.g., UV-visible), or mass spectrometry (MS), or by chromatography such as high performance liquid chromatography (HPLC) or thin layer chromatography (TLC).

Preparation of compounds can involve the protection and deprotection of various chemical groups. The need for protection and deprotection, and the selection of appropriate protecting groups can be readily determined by one skilled in the art. The chemistry of protecting groups can be found, for example, in Greene, et al., *Protective Groups in Organic Synthesis,* $2^{nd}$. Ed., Wiley & Sons, 1991, which is incorporated herein by reference in its entirety.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected.

The compounds of the invention can be prepared, for example, using the reaction pathways and techniques described below, wherein the variables described in the schemes are defined as above in the detailed description unless otherwise stated.

As shown in Scheme 1 (X is, e.g., I, Cl, Br, OTf, OTs, etc.), compounds of general formula 2 can be prepared by the reaction of a secondary amine 1 (or salts thereof) with an electrophilic species such as an alkyl, benzyl or acyl halide in the presence of a base such as diisopropylethylamine (DIPEA) in an appropriate solvent, e.g., dichloromethane (DCM). Alternatively, the secondary amine 1 can be converted to a urea of general formula 3 by reaction with an appropriate isocyanate in the presence of a base, or by a two step protocol, in which the amine 1 is first treated with p-nitrophenyl chloroformate in the presence of a base, such as DIPEA, to form an activated carbamate species followed by reaction with a suitable amine to afford a urea of general formula 3.

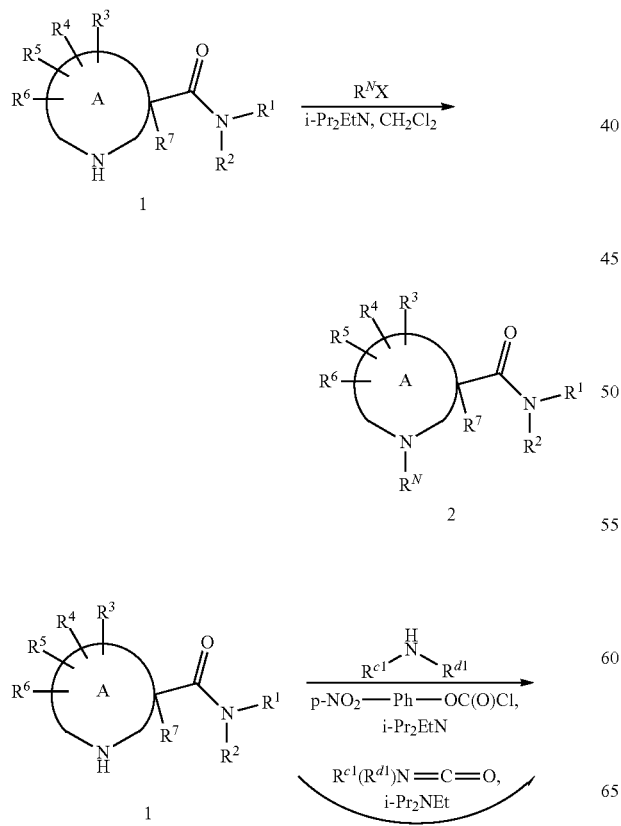

Scheme 1

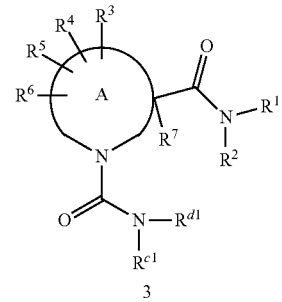

In addition to the standard $S_N2$ reaction between an alkyl halide and amine 1, the secondary amine 1 can undergo substitution by reductive amination methods, by treatment of amine 1 with an aldehyde and an appropriate reducing reagent such as sodium triacetoxyborohydride or sodium cyanoborohydride in a solvent such as DCM or dichloroethane, as shown below in Scheme 2.

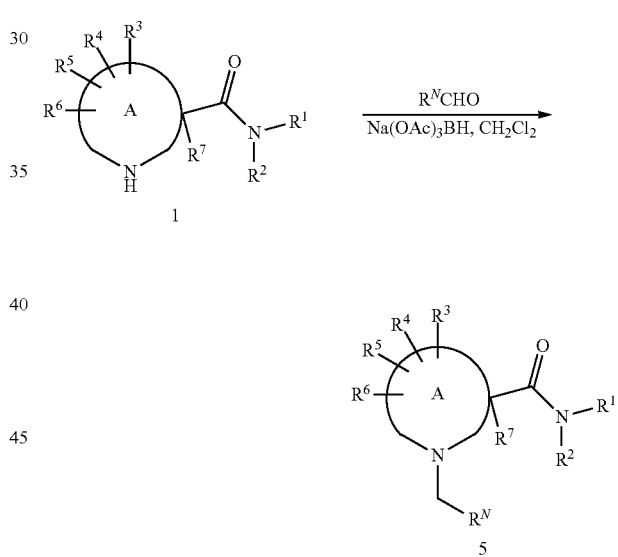

Scheme 2

Direct arylation of amine 1 to afford compounds of general formula 6 can be accomplished by heating the amine 1 and an aryl or heteroaryl halide (Ar—X; Ar is substituted or unsubstituted aromatic and X is halo) in the presence of a base such as potassium carbonate, potassium phosphate, or sodium tert-butoxide in the absence or presence of an organometallic catalyst such as palladium (0) or zinc (II) in a polar aprotic solvent such as N,N-dimethylformamide (DMF) or dimethylsulfoxide (DMSO) as shown in Scheme 3 (see Cho, G. Y. et al. *J. Org. Chem.* 2005, 70, 2346; Nie, Z. et al. *J. Med. Chem.* 2005, 48, 1596). If the nitrogen of ring A is a lactam nitrogen then an Ullman-Ukita-Buchwald-lithium reaction can be implemented using CuI as described by Wang, P.-S. et al. *Tetrahedron* 2005, 61, 2931.

Scheme 3

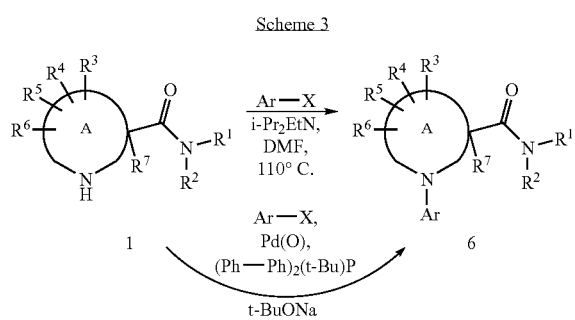

Spirocyclyl amines of general formula 9 can be prepared, for example, according to the procedure outlined in Scheme 4 (R is, e.g., alkyl, cycloalkyl, etc.). Reductive amination of the aldehyde 7 with an appropriate amine can be conducted in a solvent such as DCM and a reducing agent such as sodium triacetoxyborohydride. If the adduct does not cyclize under the above reaction conditions then the adduct can be treated with an acid such p-toluenesulfonic acid (PTSA) and refluxed in toluene or treated with a base such as LiOH or i-PrMgBr in tetrahydrofuran (THF) to afford the desired cyclized product 8. The nitrogen protecting group (PG) can then be removed by either hydrogenolysis, if PG is benzyl (Bn) or carbobenzyloxy (Cbz), or treatment with an acid, such as trifluoroacetic acid (TFA) or hydrochloric acid (HCl), if PG is tert-butoxycarbonyl (Boc).

Scheme 4

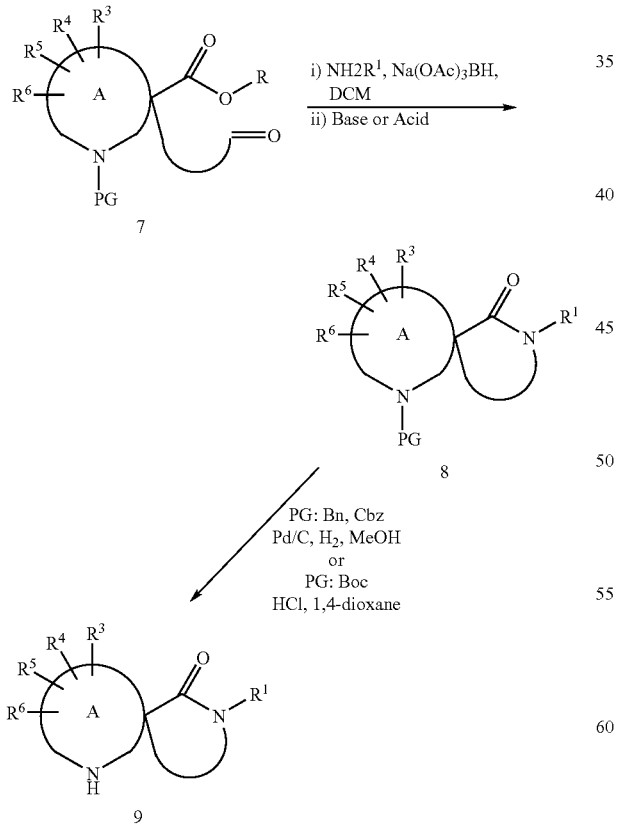

The aldehyde 7 can be prepared by any one of a variety of methods known to those skilled in the art of organic synthesis such as the one outlined in Scheme 5 (R is, e.g., alkyl, cycloalkyl, etc.). The ester 10 can be treated with a strong base such as lithium diisopropyl amide (LDA) or LiHMDS in an ethereal solvent such as THF at a low temperature (e.g. −78° C.) and under an inert atmosphere (e.g. $N_2$) to form the corresponding enolate which can be reacted with an appropriate alkene electrophile such as 1-bromo-3-methylbut-2-ene to afford the α-alkylated ester adduct 11. Subsequent ozonolysis of the olefin can be conducted by bubbling ozone through a low temperature (e.g. −78° C.) solution of alkene 11 dissolved in a solvent such as anhydrous DCM followed by reduction of the ozonide intermediate, which is presumed to form under the prescribed reaction conditions, with a reducing agent such as zinc or dimethylsulfide.

Scheme 5

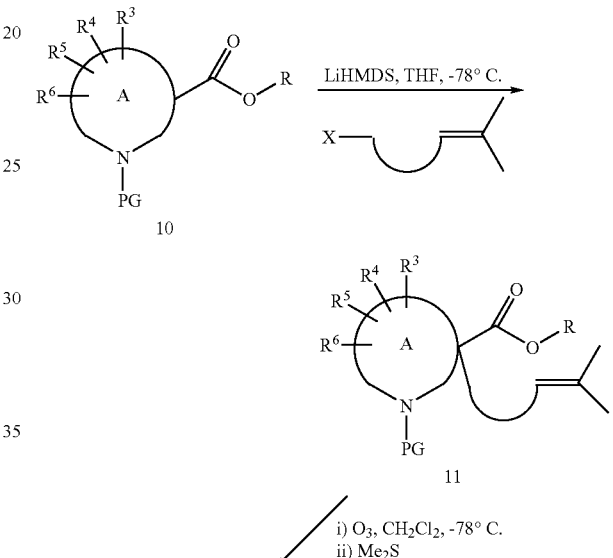

In the case when $R^3$ and $R^4$ (or optionally any two of $R^3$, $R^4$, $R^5$, and $R^6$) are attached to the same atom of ring A to form a cycloalkyl or heterocycloalkyl group, the amine 14 can be prepared from the corresponding ester 12 as depicted in Scheme 6. Alkaline hydrolysis of ester 12 using a mineral base such as LiOH or NaOH in a suitable solvent mixture such as $THF/H_2O$ can afford the corresponding carboxylic acid, which can then be activated by using a conventional amide coupling reagents such as a benzotriazole-1-yl-oxy-tris-(dimethylamino)-phosphonium (BOP) reagent in the presence of a tertiary amine base, such as DIPEA or N-methylmorpholine, in a polar aprotic solvent such as DMF and reacted with the appropriate amine ($R^1R^2NH$) to afford the desired amide 13. The A ring nitrogen can then be deprotected and derivatized accordingly as described previously above.

Scheme 6

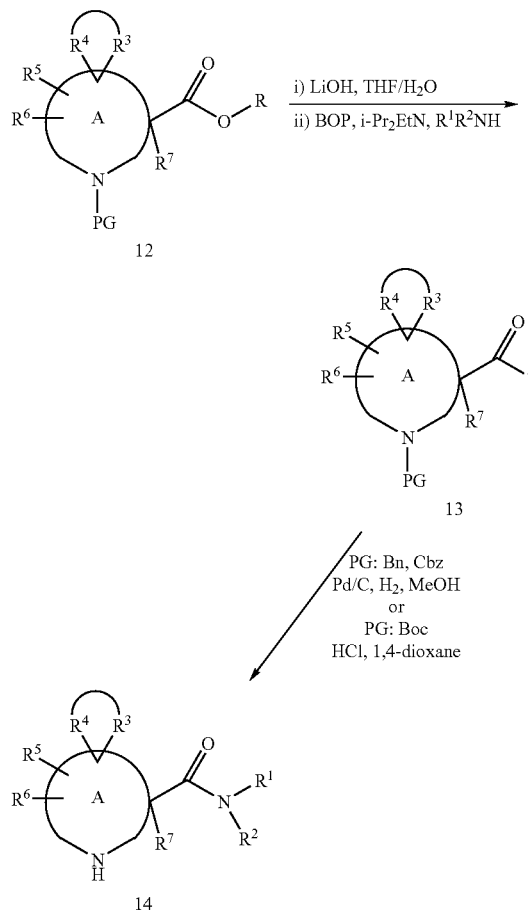

Scheme 7

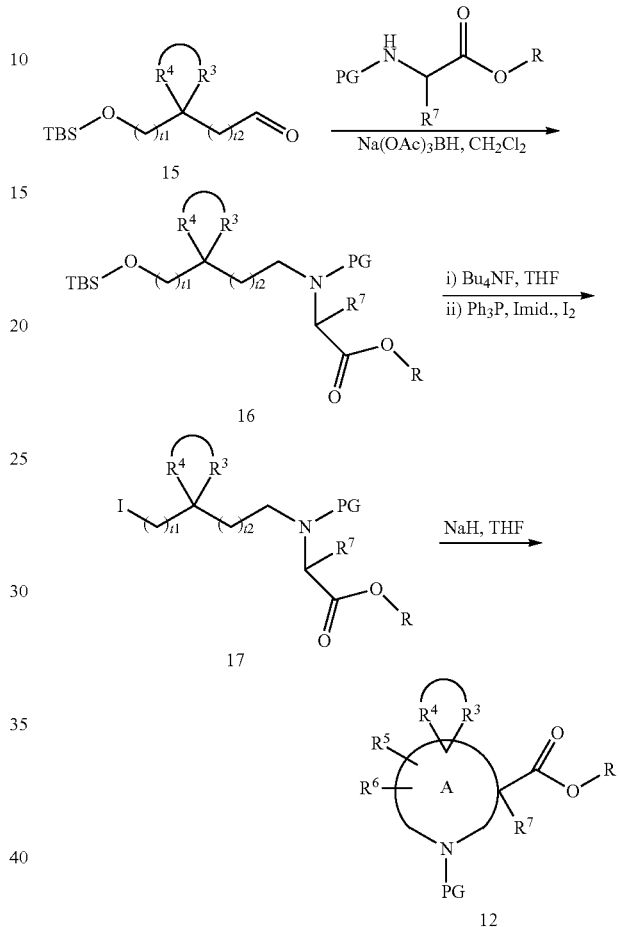

alternate halogenating agents are employed. The intramolecular ring closure to form the A ring can be accomplished by forming the enolate of 17 by treatment of ester 17 with an appropriate base such as NaH or LiHMDS.

The carbocycle or heterocycle formed by $R^3$ and $R^4$ (or optionally between any two of $R^3$, $R^4$, $R^5$, and $R^6$) in intermediates having the general formula 12 can be formed by any of a variety of conventional methods known to one skilled in the art of organic synthesis such as ring closing metathesis or by ring closing lactam or lactone formation. Alternatively, the carbocycle or heterocycle can be preformed as illustrated in Scheme 7 (PG is a protecting group, t1 and t2 are integers sufficient to result in ring A after ring closure; R is, e.g., alkyl, cycloalkyl, etc.). In this example, a readily available starting material with a preassembled cycloalkyl or heterocycloalkyl group, such as the compound with general formula 15 (optionally substituted with $R^5$ and $R^6$), can be reacted with an amine, such as an amino acid ester, in the presence of a reducing reagent, such as sodium triacetoxyborohydride to afford the amino acid derivative 16. The hydroxyl protecting group, which can be any appropriate hydroxyl protecting group such as tert-butyldimethylsilyl (TBS), can be removed under the appropriate reaction conditions. In the case of a silyl ether protecting group, a fluoride reagent such as tetrabutylammoniumfluoride (TBAF), HF pyridine, or fluorosilicic acid can be used. The hydroxyl group can then be converted to a leaving group such as a triflate, tosylate, or halide by methods known to one skilled in the art. For the latter conversion a reagent such as phosphorous tribromide, phosphorous pentachloride, or treatment with triphenylphosphine and 1H-imidazole in the presence of iodine can afford the desired halide 17, wherein the I atom in 17 can be other halogens when

Methods

Compounds of the invention can modulate activity of 11βHSD1. The term "modulate" is meant to refer to an ability to increase or decrease activity of an enzyme. Accordingly, compounds of the invention can be used in methods of modulating 11βHSD1 by contacting the enzyme with any one or more of the compounds or compositions described herein. In some embodiments, compounds of the present invention can act as inhibitors of 11βHSD1. In further embodiments, the compounds of the invention can be used to modulate activity of 11βHSD1 in an individual in need of modulation of the enzyme by administering a modulating amount of a compound of the invention.

The present invention further provides methods of inhibiting the conversion of cortisone to cortisol in a cell, or inhibiting the production of cortisol in a cell, where conversion to or production of cortisol is mediated, at least in part, by 11βHSD1 activity. Methods of measuring conversion rates of cortisone to cortisol and vice versa, as well as methods for measuring levels of cortisone and cortisol in cells, are routine in the art.

The present invention further provides methods of increasing insulin sensitivity of a cell by contacting the cell with a compound of the invention. Methods of measuring insulin sensitivity are routine in the art.

The present invention further provides methods of treating diseases associated with activity or expression, including abnormal activity and overexpression, of 11βHSD1 in an individual (e.g., patient) by administering to the individual in need of such treatment a therapeutically effective amount or dose of a compound of the present invention or a pharmaceutical composition thereof. Example diseases can include any disease, disorder or condition that is directly or indirectly linked to expression or activity of the enzyme or receptor. An 11βHSD1-associated disease can also include any disease, disorder or condition that can be prevented, ameliorated, or cured by modulating enzyme activity.

Examples of 11βHSD1-associated diseases include obesity, diabetes, glucose intolerance, insulin resistance, hyperglycemia, atherosclerosis, hypertension, hyperlipidemia, cognitive impairment, dementia, depression (e.g., psychotic depression), glaucoma, cardiovascular disorders, osteoporosis, and inflammation. Further examples of 11βHSD1-associated diseases include metabolic syndrome, coronary heart disease, type 2 diabetes, hypercortisolemia, androgen excess (hirsutism, menstrual irregularity, hyperandrogenism) and polycystic ovary syndrome (PCOS). In some embodiments, the compounds of the invention are useful in the treatment of diabetes, such as type 2 diabetes. In further embodiments, the compounds of the invention are useful in the treatment of obesity.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal. In some embodiments, the cell is an adipocyte, a pancreatic cell, a hepatocyte, neuron, or ocular cell.

As used herein, the term "contacting" refers to the bringing together of indicated moieties in an in vitro system or an in vivo system. For example, "contacting" the 11βHSD1 enzyme with a compound of the invention includes the administration of a compound of the present invention to an individual or patient, such as a human, having 11βHSD1, as well as, for example, introducing a compound of the invention into a sample containing a cellular or purified preparation containing the 11βHSD1 enzyme.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

As used herein, the term "treating" is meant to include (1) preventing the disease; for example, preventing a disease, condition or disorder in an individual who may be predisposed to the disease, condition or disorder but does not yet experience or display the pathology or symptomatology of the disease; (2) inhibiting the disease; for example, inhibiting a disease, condition or disorder in an individual who is experiencing or displaying the pathology or symptomatology of the disease, condition or disorder (i.e., arresting further development of the pathology and/or symptomatology); or (3) ameliorating the disease; for example, ameliorating a disease, condition or disorder in an individual who is experiencing or displaying the pathology or symptomatology of the disease, condition or disorder (i.e., reversing the pathology and/or symptomatology).

Pharmaceutical Formulations and Dosage Forms

When employed as pharmaceuticals, the compounds of the invention can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal or intramuscular injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, one or more of the compounds of the invention above in combination with one or more pharmaceutically acceptable carriers. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, micro-crystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compounds of the invention can also be formulated in combination with one or more additional active ingredients which can include any pharmaceutical agent such as anti-viral agents, antibodies, immune suppressants, anti-inflammatory agents and the like.

Labeled Compounds and Assay Methods

Another aspect of the present invention relates to labeled compounds of the invention (radio-labeled, fluorescent-labeled, etc.) that would be useful not only in radio-imaging but also in assays, both in vitro and in vivo, for localizing and quantitating the enzyme in tissue samples, including human, and for identifying ligands by inhibition binding of a labeled compound. Accordingly, the present invention includes enzyme assays that contain such labeled compounds.

The present invention further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^2$H (also written as D for deuterium), $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. The radionuclide that is incorporated in the instant radio-labeled compounds will depend on the specific application of that radio-labeled compound. For example, for in vitro receptor labeling and competition assays, compounds that incorporate $^3$H, $^{14}$C, $^{82}$Br, $^{125}$I, $^{131}$I, $^{35}$S or will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful.

It is understood that a "radio-labeled compound" is a compound that has incorporated at least one radionuclide. In some embodiments the radionuclide is selected from the group consisting of $^3$H, $^{14}$C, $^{125}$I, $^{35}$S and $^{82}$Br.

In some embodiments, the labeled compounds of the present invention contain a fluorescent label.

Synthetic methods for incorporating radio-isotopes and fluorescent labels into organic compounds are known in the art.

A labeled compound of the invention (radio-labeled, fluorescent-labeled, etc.) can be used in a screening assay to identify/evaluate compounds. For example, a newly synthesized or identified compound (i.e., test compound) which is labeled can be evaluated for its ability to bind a 11βHSD1 by monitoring its concentration variation when contacting with the 11βHSD1, through tracking the labeling. For another example, a test compound (labeled) can be evaluated for its ability to reduce binding of another compound which is known to bind to 11βHSD1 (i.e., standard compound). Accordingly, the ability of a test compound to compete with the standard compound for binding to the 11βHSD1 directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present invention also includes pharmaceutical kits useful, for example, in the treatment or prevention of 11βHSD1-associated diseases or disorders, obesity, diabetes and other diseases referred to herein which include one or more containers containing a pharmaceutical composition comprising a therapeutically effective amount of a compound of the invention. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results. The compounds of the Examples were found to be inhibitors of 11βHSD1 according to one or more of the assays provided herein.

EXAMPLES

Example 1

7-(2-Chlorophenyl)-1-isobutyl-1,7-diazaspiro[4.4]nonan-6-one

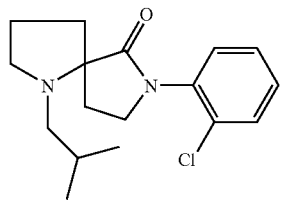

Step 1: 1-tert-Butyl 2-methyl(2S)-pyrrolidine-1,2-dicarboxylate

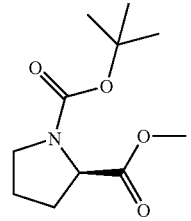

N-(tert-Butoxycarbonyl)-L-proline (7.05 g, 0.0328 mol) was dissolved in THF (200 mL, 2 mol) and to this solution was added potassium carbonate (10.2 g, 0.0738 mol) and methyl iodide (5.0 mL, 0.08 mol). The resulting heterogeneous solution was heated to reflux for 16 h with vigorous stirring. The mixture was then filtered through a pad of diatomaceous earth and the filter pad was washed thoroughly with tetrahydrofuran (THF). The volatiles were removed in vacuo and the resulting residue was purified by CombiFlash chromatography using a 40 g column and eluting with EtOAc/hexanes (0-25%) to afford the desired product as a yellow oil (7.3 g, 97%). LC-MS: 130.2 (M–Boc+2H)$^+$ and 252.1 (M+Na)$^+$.

Step 2: 1-tert-Butyl 2-methyl 2-(3-methylbut-2-en-1-yl)pyrrolidine-1,2-dicarboxylate

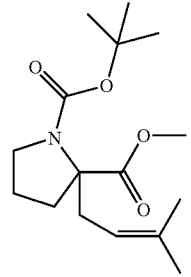

1-tert-Butyl 2-methyl (2S)-pyrrolidine-1,2-dicarboxylate (2.29 g, 0.00999 mol) was dissolved in anhydrous THF (30 mL) and the solution was cooled to −78° C. prior to the drop-wise addition of 1.0 M of lithium hexamethyldisilazide in THF (16 mL) over 15 min. After stirring for 1 h, 1-bromo-3-methylbut-2-ene (1.6 mL, 0.014 mol) was added and the resultant solution was stirred for 5 hours at −78° C. The reaction was quenched by the drop-wise addition of saturated NH₄Cl (15 mL). After gradually warming to room temperature (RT), the reaction mixture was diluted with EtOAc (100 mL) and water (10 mL). The organic layer was washed with water (15 mL) and the combined aqueous phases were extracted with EtOAc several times. The combined organic phases were washed with brine, dried (Na₂SO₄), and concentrated in vacuo to afford the desired product, which was used in the subsequent step without further purification. LC-MS: 198.2 (M−Boc+2H)⁺ and 320.2 (M+Na)⁺.

Step 3: 1-tert-Butyl 2-methyl 2-(2-oxoethyl)pyrrolidine-1,2-dicarboxylate

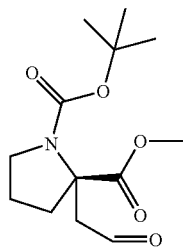

1-tert-Butyl 2-methyl 2-(3-methylbut-2-en-1-yl)pyrrolidine-1,2-dicarboxylate (2.0 g, 0.0067 mol) was dissolved in anhydrous dichloromethane (DCM) (120 mL) and the resulting solution was cooled to −78° C. under an atmosphere of nitrogen. Ozone was then bubbled through the solution for approximately 15 min. until the solution turned blue. The solution was then purged with O₂ (g) for 1 min. and then N₂ (g) for 20 min. The ozonide intermediate was reduced by the addition of dimethyl sulfide (4 mL, 0.05 mol) and the solution was stirred for 30 min. before warming to ambient temperature. The volatiles were removed in vacuo and the residue was purified by CombiFlash chromatography using a 40 g column and eluting with 10-60% EtOAc/hexanes to afford the desired product (1.61 g, 88%). LC-MS: 172.2 (M−Boc+2H)⁺ and 294.2 (M+Na)⁺.

Step 4: 1-tert-Butyl 2-methyl 2-{2-[(2-chlorophenyl)amino]ethyl}pyrrolidine-1,2-dicarboxylate

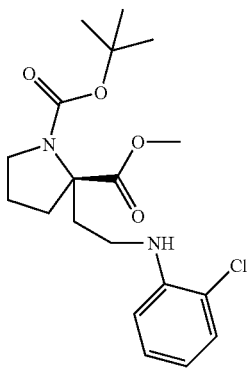

A solution of 1-tert-butyl 2-methyl 2-(2-oxoethyl)pyrrolidine-1,2-dicarboxylate (220 mg, 0.00081 mol) in DCM (anhydrous, 4 mL) was added to 2-chloroaniline (110 µL, 0.0010 mol) and the resulting solution was stirred for 20 min. Sodium triacetoxyborohydride (290 mg, 0.0014 mol) was then added to the mixture. After stirring at RT for 12 h, the reaction mixture was diluted with EtOAc and quenched by the addition of water. The crude mixture was filtered through a pad of diatomaceous earth and the filter pad were washed several times with EtOAc and the resulting layers were of the filtrate separated. The aqueous phase was extracted with EtOAc (3×10 mL) and the combined organic phases were washed with brine (2×5 mL). The organic phase was then dried (NaSO₄), filtered, and concentrated in vacuo to afford the desired product. LC-MS: 327.1 (M−Boc+2H)⁺ and 383.2 (M+1H)⁺.

Step 5: tert-Butyl 7-(2-chlorophenyl)-6-oxo-1,7-diazaspiro[4.4]nonane-1-carboxylate

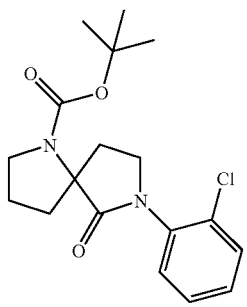

1-tert-Butyl 2-methyl 2-{2-[(2-chlorophenyl)amino]ethyl}pyrrolidine-1,2-dicarboxylate, was dissolved in anhydrous THF (4 mL) and cooled to 0° C. To this cooled solution was added isopropylmagnesium chloride in THF (2.0 M, 2 mL). The reaction vial was then sealed and heated to 64° C. and stirred for 18 h. The reaction mixture was then diluted with EtOAc and quenched by the addition of water. The crude mixture was filtered through a pad of diatomaceous earth and the filter pad was washed several times with EtOAc. The organic and aqueous layers of the filtrate were separated. The aqueous phase was extracted with EtOAc (3×10 mL) and the combined organic phases were washed with brine (2×5 mL), then dried (NaSO₄), filtered, and concentrated in vacuo to afford the desired product. LC-MS: 251.1 (M−Boc+2H)⁺ and 295.1 (M−t-Bu+2H)⁺.

Step 6.
7-(2-Chlorophenyl)-1,7-diazaspiro[4.4]nonan-6-one

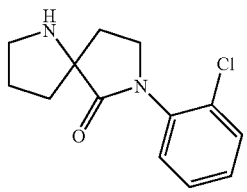

tert-Butyl 7-(2-chlorophenyl)-6-oxo-1,7-diazaspiro[4.4]nonane-1-carboxylate was dissolved in a 4.0 M solution of HCl in 1,4-dioxane, and the resulting mixture was stirred for Step 7. 7-(2-Chlorophenyl)-1-isobutyl-1,7-diazaspiro[4.4]nonan-6-one

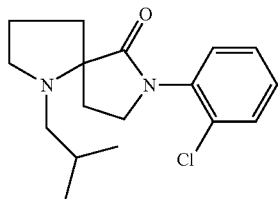

7-(2-Chlorophenyl)-1,7-diazaspiro[4.4]nonan-6-one (20 mg, 0.00008 mol) was dissolved in anhydrous DCM (2 mL). To this mixture was added isobutyraldehyde (8.0 μL, 0.000088 mol) and sodium triacetoxyborohydride (3.0E1 mg, 0.00014 mol). The resulting solution was stirred at RT for 16 h. The volatiles were removed in vacuo and the resulting residue was dissolved in acetonitrile/$H_2O$ and purified by prep.-LC/MS chromatography to afford the desired product. LC-MS: 307.1 $(M+1H)^+$.

Example 2

7-(2-Chlorophenyl)-1-(cyclopropylmethyl)-1,7-diazaspiro[4.4]nonan-6-one

This compound was prepared by using procedures that are analogous to those described for the synthesis of Example 1. LC-MS: 305.1 $(M+1H)^+$.

Example 3

7-(2-Chlorophenyl)-1-(tetrahydrofuran-3-ylmethyl)-1,7-diazaspiro[4.4]nonan-6-one This compound was prepared by using procedures that are analogous to those described for the synthesis of Example 1. LC-MS: 335.1 $(M+1H)^+$.

Example 4

7-(2-Chlorophenyl)-1-(1H-imidazol-4-ylmethyl)-1,7-diazaspiro[4.4]nonan-6-one

This compound was prepared by using procedures that are analogous to those described for the synthesis of Example 1. LC-MS: 331.1 $(M+1H)^+$.

Example 5

7-(2-Chlorophenyl)-1-(1H-indol-5-ylmethyl)-1,7-diazaspiro[4.4]nonan-6-one

This compound was prepared by using procedures that are analogous to those described for the synthesis of Example 1. LC-MS: 380.1 $(M+1H)^+$.

Example 6

7-(2-Chlorophenyl)-1-(5-nitropyridin-2-yl)-1,7-diazaspiro[4.4]nonan-6-one

This compound was prepared by using procedures that were analogous to those described for the synthesis of Example 1, with the exception that step 7 was replaced by the following procedure.

7-(2-Chlorophenyl)-1,7-diazaspiro[4.4]nonan-6-one (20 mg, 0.00008 mol) was dissolved in dimethylformamide (DMF) (1 mL). To this solution was added 2-chloro-5-(trifluoromethyl)pyridine (22 mg, 0.00012 mol) and DIPEA (42 μL, 0.00024 mol). The resulting solution was stirred at 110° C. for 24 h in a sealed tube. The crude reaction mixture was then diluted with acetonitrile (ACN) and water, and purified by prep.-LC-MS chromatography to afford the desired product. LC-MS: 373.1 $(M+1H)^+$.

Example 7

7-(2-Chlorophenyl)-1-[5-(trifluoromethyl)pyridin-2-yl]-1,7-diazaspiro[4.4]nonan-6-one This compound was prepared by using procedures that are analogous to those described for the synthesis of Example 6. LC-MS: 396.0/398.0 $(M+1H)^+$.

Example 8

7-(2-Chlorophenyl)-1-{[4-(difluoromethoxy)phenyl]sulfonyl}-1,7-diazaspiro[4.4]-nonan-6-one This compound was prepared by using procedures that are analogous to those described for the synthesis of Example 1, with the exception that step 7 was replaced by the following procedure.

7-(2-Chlorophenyl)-1,7-diazaspiro[4.4]nonan-6-one (20 mg, 0.00008 mol) was dissolved in DCM. To this solution was added N,N-diisopropylethylamine (DIPEA) (42 μL, 0.00024 mol) and 4-(difluoromethoxy)benzenesulfonyl chloride (21 mg, 0.000088 mol) at 0° C. The solution was allowed to gradually warm to RT while stirring for 18 h. LC-MS: 457.1 $(M+1H)^+$.

Example 9

7-(1-Adamantyl)-1-isobutyl-1,7-diazaspiro[4.4]nonan-6-one

This compound was prepared by using procedures that are analogous to those described for the synthesis of Example 1. LC-MS: 331.2 $(M+1H)^+$.

Example 10

7-(1-Adamantyl)-1-(pyridin-2-ylmethyl)-1,7-diazaspiro[4.4]nonan-6-one

This compound was prepared by using procedures that are analogous to those described for the synthesis of Example 1. LC-MS: 366.2 $(M+1H)^+$.

Example 11

7-(1-Adamantyl)-1-(cyclopentylmethyl)-1,7-diazaspiro[4.4]nonan-6-one

This compound was prepared by using procedures that are analogous to those described for the synthesis of Example 1. LC-MS: 357.3 (M+1H)$^+$.

Example 12

7-(1-Adamantyl)-1-[5-(trifluoromethyl)pyridin-2-yl]-1,7-diazaspiro[4.4]nonan-6-one This compound was prepared by using procedures that are analogous to those described for the synthesis of Example 6. LC-MS: 420.1 (M+1H)$^+$.

Example 13

7-(1-Adamantyl)-1-[3-chloro-5-(trifluoromethyl)pyridin-2-yl]-1,7-diazaspiro[4.4]-nonan-6-one This compound was prepared by using procedures that are analogous to those described for the synthesis of Example 6. LC-MS: 454.1/456.1 (M+1H)$^+$.

Example 14

6-[7-(1-Adamantyl)-6-oxo-1,7-diazaspiro[4.4]non-1-yl]nicotinonitrile

This compound was prepared by using procedures that are analogous to those described for the synthesis of Example 6. LC-MS: 377.1 (M+1H)$^+$.

Example 15

7-Cyclohexyl-1-(cyclopentylmethyl)-1,7-diazaspiro[4.4]nonan-6-one

This compound was prepared by using procedures that are analogous to those described for the synthesis of Example 1. LC-MS: 305.2 (M+1H)$^+$.

Example 16

4-[(7-Cyclohexyl-6-oxo-1,7-diazaspiro[4.4]non-1-yl)methyl]benzonitrile

This compound was prepared by using procedures that are analogous to those described for the synthesis of Example 1. LC-MS: 338.2 (M+1H)$^+$.

Example 17

1-(4-Chlorobenzyl)-7-cyclohexyl-1,7-diazaspiro[4.4]nonan-6-one

This compound was prepared by using procedures that are analogous to those described for the synthesis of Example 1. LC-MS: 347.1/349.2 (M+1H)$^+$.

Example 18

7-Cyclohexyl-1-(2,4-difluorobenzyl)-1,7-diazaspiro[4.4]nonan-6-one

This compound was prepared by using procedures that are analogous to those described for the synthesis of Example 1. LC-MS: 349.2 (M+1H)$^+$.

Example 19

7-Cyclohexyl-1-{[6-(trifluoromethyl)pyridin-3-yl]methyl}-1,7-diazaspiro[4.4]-nonan-6-one This compound was prepared by using procedures that are analogous to those described for the synthesis of Example 1. LC-MS: 382.2 (M+1H)$^+$.

Example 20

7-Cyclohexyl-1-(1H-indol-3-ylmethyl)-1,7-diazaspiro[4.4]nonan-6-one

This compound was prepared by using procedures that are analogous to those described for the synthesis of Example 1. LC-MS: 223.2 (M−(1H-indol-3-ylmethyl)+2H)$^+$; 352.3 (M+1H)$^+$.

Example 21

Ethyl 7-cyclohexyl-6-oxo-1,7-diazaspiro[4.4]nonane-1-carboxylate

This compound was prepared by using procedures that are analogous to those described for the synthesis of Example 8. LC-MS: 295.3 (M+1H)$^+$.

Example 22

7-Cyclohexyl-1-[2-fluoro-5-(trifluoromethyl)benzoyl]-1,7-diazaspiro[4.4]nonan-6-one This compound was prepared by using procedures that are analogous to those described for the synthesis of Example 8. LC-MS: 413.2 (M+1H)$^+$.

Example 23

1-(Cyclobutylcarbonyl)-7-cyclohexyl-1,7-diazaspiro[4.4]nonan-6-one

This compound was prepared by using procedures that are analogous to those described for the synthesis of Example 8. LC-MS: 305.2 (M+1H)$^+$; 223.2 (M−acyl+2H)$^+$.

Example 24

7-Cyclohexyl-1-(pyridin-2-ylcarbonyl)-1,7-diazaspiro[4.4]nonan-6-one

This compound was prepared by using procedures that are analogous to those described for the synthesis of Example 8. LC-MS: 328.2 (M+1H)$^+$; 350.1 (M+Na)$^+$.

Example 25

7-(2-Chlorophenyl)-1-(ethylsulfonyl)-1,7-diazaspiro [4.4]nonan-6-one

This compound was prepared by using procedures that are analogous to those described for the synthesis of Example 8. LC-MS: 343.1/345.0 (M+1H)$^+$; 365.0/367.0 (M+Na)$^+$.

Example 26

2-Cyclohexyl-6-isobutyl-2,6-diazaspiro[4.5]decan-1-one

This compound was prepared by using procedures that are analogous to those described for the synthesis of Example 1. LC-MS: 293.3 (M+1H)$^+$.

Example 27

2-Cyclohexyl-6-(cyclopentylmethyl)-2,6-diazaspiro [4.5]decan-1-one

This compound was prepared by using procedures that are analogous to those described for the synthesis of Example 1. LC-MS: 319.3 (M+1H)$^+$.

Example 28

2-Cyclohexyl-6-(pyridin-2-ylmethyl)-2,6-diazaspiro [4.5]decan-1-one

This compound was prepared by using procedures that are analogous to those described for the synthesis of Example 1. LC-MS: 328.3 (M+1H)$^+$.

Example 29

2-Cyclohexyl-6-[5-(trifluoromethyl)pyridin-2-yl]-2, 6-diazaspiro[4.5]decan-1-one

This compound was prepared by using procedures that are analogous to those described for the synthesis of Example 6. LC-MS: 382.2 (M+1H)$^+$.

Example 30

5-Benzyl-N-cyclohexyl-5-azaspiro[2.4]heptane-6-carboxamide

Step 1: [1-({[tert-Butyl(dimethyl)silyl]oxy}methyl) cyclopropyl]methanol 1,1-Bis(hydroxymethyl)cyclopropane (1.0 g, 0.0098 mol), triethylamine (TEA) (2.0 mL, 0.015 mol), and 1H-imidazole (0.13 g, 0.0020 mol) were dissolved in anhydrous DCM (15 mL) and the solution was cooled to 0° C. A solution of tert-butyldimethylsilyl chloride (1.55 g, 0.0103 mol) in DCM (5 mL) was added drop-wise and the resulting mixture was allowed to warm to RT and stirred overnight. The reaction was quenched with saturated aqueous NaHCO$_3$ and extracted with DCM (3×). The organic extract was dried (magnesium sulfate), filtered, and concentrated in vacuo. The crude product was identified by $^1$H NMR and used in the next step without further purification.

Step 2: 1-({[tert-Butyl(dimethyl)silyl]oxy}methyl) cyclopropanecarbaldehyde

To a stirred solution of DMSO (6.9 mL, 0.097 mol) in anhydrous DCM (90 mL) at −70° C. was added oxalyl chloride (4.20 mL, 0.0486 mol). After stirring for 10 min. at −70° C., a solution of [1-({[tert-butyl(dimethyl)silyl]oxy}methyl) cyclopropyl]methanol (7.011 g, 0.03240 mol) in anhydrous DCM (30 mL) was added via cannula. The resulting milky mixture was slowly warmed to −55° C. over 45 min. DIPEA (34.0 mL, 0.194 mol) was added. The resulting mixture was stirred for 5 min. at −55° C., and then the cooling bath was removed and the reaction mixture was allowed to warm to RT. The reaction was then quenched with saturated aqueous NaHCO$_3$ (150 mL) and extracted with DCM (2×). The combined organic layers were washed with brine, dried over magnesium sulfate, filtered and concentrated in vacuo. The resulting residue was purified by Combiflash chromatography eluting with 0-10% EtOAc/hexanes to afford the desired product as a colorless oil (4.558 g, 66% yield).

Step 3: Methyl (benzyl{[1-({[tert-butyl(dimethyl) silyl]oxy}methyl)cyclopropyl]methyl}amino)acetate To a stirred solution of 1-({[tert-butyl(dimethyl)silyl] oxy}methyl)cyclopropanecarbaldehyde (5.0 g, 0.023 mol) in anhydrous 1,2-dichloroethane (113 mL, 1.44 mol) was added glycine methyl ester, hydrochloride (2.92 g, 0.0232 mol), TEA (6.53 mL, 0.0466 mol), and sodium triacetoxyborohydride (10.4 g, 0.0467 mol). The resulting mixture was stirred at RT for 1 h. LC/MS data indicated that the reductive amination was complete to afford methyl ({[1-({[tert-butyl-(dimethyl)silyl]oxy}methyl)cyclopropyl]methyl}amino)acetate. LC-MS: 288.2 (M+1H)$^+$. To the crude reaction mixture was added benzaldehyde (2.8 mL, 0.028 mol), followed by a second aliquot of sodium triacetoxyborohydride (6 g). After stirring at RT for 2 h, the reaction was quenched by the addition of saturated aqueous NaHCO$_3$. The organic layer was separated and washed with brine, then dried (MgSO$_4$), and concentrated in vacuo. The crude product (9.1 g) was purified by Combiflash chromatography (120 g silica gel column, 0-15% EtOAc/hexanes 20 min), to afford the desired product as an oil (4.6 g). LC/MS: 378.2 (M+1H)$^+$.

Step 4: Methyl (benzyl{[1-(hydroxymethyl)cyclopropyl]methyl}amino)acetate

To a stirred solution of methyl (benzyl{[1-({[tert-butyl (dimethyl)silyl]oxy}methyl)-cyclopropyl]methyl}amino) acetate (4.0 g, 0.010 mol) in ACN (100 mL, 2 mol) was added at RT, fluorosilicic acid in water (2.00 M, 10.6 mL). The resulting mixture was stirred at RT overnight. The reaction was quenched by the addition of saturated aqueous NaHCO$_3$ until the reaction mixture was alkaline and then extracted with EtOAc (2×). The organic extracts were combined and washed with brine, then dried (MgSO$_4$), filtered and concentrated in vacuo to afford the desired product (1.1 g), which was identified by $^1$H NMR spectroscopy and used in the next step without further purification.

Step 5: Methyl (benzyl{[1-(iodomethyl)cyclopropyl] methyl}amino)acetate

To a stirred solution of methyl (benzyl{[1-(hydroxymethyl)cyclopropyl]methyl}-amino)acetate (1.1 g, 0.0042 mol), triphenylphosphine (2.74 g, 0.0104 mol) and 1H-imidazole (0.711 g, 0.0104 mol) in ether (30.0 mL, 0.286 mol)

and ACN (10.0 mL, 0.192 mol) at 0° C. was added iodine (2.12 g, 0.00835 mol). The resulting yellow suspension was stirred at 0° C. for 50 min. The reaction was quenched by the addition of 10% aqueous Na$_2$S$_2$O$_3$ (30 ml) and saturated aqueous NaHCO$_3$ (30 mL). The product was extracted with EtOAc (2×) and the combined organic extracts were washed with brine, then dried over MgSO$_4$, filtered and concentrated in vacuo. The residue was purified by Combiflash chromatography eluting with 0-15% EtOAc/hexanes to afford the desired product (1.0 g). LC/MS: 374.1 (M+1H)$^+$.

Step 6:
5-Benzyl-5-azaspiro[2.4]heptane-6-carboxylic acid

To a stirred solution of methyl (benzyl{[1-(iodomethyl) cyclopropyl]methyl}amino)acetate (0.10 g, 0.00027 mol) in DMF (2.0 mL, 0.026 mol) at RT was added sodium hydride (16 mg, 0.00040 mol). The reaction mixture was stirred at RT for 1 h to achieve the desired cyclization and hydrolysis of the methyl ester. The reaction was quenched by the addition of water and acidified with 1 N HCl to pH 3-4 and washed with EtOAc. The aqueous layer was concentrated in vacuo to afford the desired product as a yellow solid, which was used in the next step without purification. LC/MS: m/e 232.2 (M+1H)$^+$.

Step 7: 5-Benzyl-N-cyclohexyl-5-azaspiro[2.4]heptane-6-carboxamide

To a mixture of 5-benzyl-5-azaspiro[2.4]heptane-6-carboxylic acid (62.0 mg, 0.000268 mol) dissolved in DMF (1.0 mL, 0.013 mol) was added cyclohexanamine (30.7 µL, 0.000268 mol), benzotriazol-1-yloxytris(dimethylamino) phosphonium hexafluorophosphate (130 mg, 0.00029 mol) and TEA (0.25 mL, 0.0018 mol). After stirring at RT for 1 h, the reaction mixture was quenched with saturated aqueous NaHCO$_3$ and extracted with EtOAc. The extracts were washed with brine, then dried (MgSO$_4$), filtered and concentrated in vacuo. The crude material was purified by prep.-LC/MS to afford the desired product as a white solid. LC/MS: m/e 313.2 (M+1H)$^+$.

Example 31

N-Cyclohexyl-5-isobutyl-5-azaspiro[2.4]heptane-6-carboxamide

Step 1:
N-Cyclohexyl-5-azaspiro[2.4]heptane-6-carboxamide

5-Benzyl-N-cyclohexyl-5-azaspiro[2.4]heptane-6-carboxamide (prepared according to Example 30, 14 mg, 0.0000448 mol) was dissolved in methanol (1 mL). To this solution was added Pd/C (3 mg) and the resulting mixture was stirred under an atmosphere of hydrogen overnight. The catalyst was filtered off and the volatiles were removed in vacuo to afford the desired product (10.3 mg), which was used in the next step without further purification. LC/MS: 223.2 (M+H)$^+$.

Step 2: N-Cyclohexyl-5-isobutyl-5-azaspiro[2.4]heptane-6-carboxamide

To a solution of N-cyclohexyl-5-azaspiro[2.4]heptane-6-carboxamide (10.0 mg, 0.0000450 mol) in 1,2-dichloroethane (0.5 mL, 0.006 mol) was added isobutyraldehyde (4.9 µL, 0.000054 mol), TEA (10 µL, 0.00009 mol), and sodium triacetoxyborohydride (20 mg, 0.00009 mol). After stirring for 30 min. at RT, the reaction mixture was quenched with saturated aqueous NaHCO$_3$ and extracted with EtOAc. The combined organic extracts were washed with brine, then dried (MgSO$_4$), filtered and concentrated in vacuo. The concentrate was purified by prep.-LC/MS to afford the desired product. LC/MS: 279.3 (M+H)$^+$.

Example 32

(3R)-1-(4-Chlorobenzyl)-7-cyclohexyl-3-hydroxy-1,7-diazaspiro[4.4]nonan-6-one

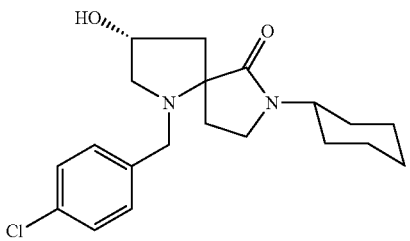

Step 1: 1-tert-Butyl 2-methyl (2S,4R)-4-{[tert-butyl (dimethyl)silyl]oxy}pyrrolidine-1,2-dicarboxylate

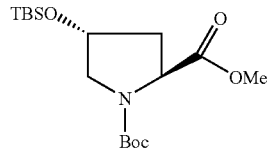

Methyl (2S,4R)—N-tert-butoxycarbonyl-4-hydroxy-2-pyrrolidinecarboxylate (5.00 g, 0.0198 mol) was dissolved in anhydrous DMF (30 mL, 0.4 mol) under an atmosphere of nitrogen. To this solution was added 1H-imidazole (3.2 g, 0.046 mol) followed by tert-butyldimethylsilyl chloride (3.92 g, 0.0260 mol). The resulting mixture became translucent. After stirring for 16 h at RT, the reaction mixture was diluted with ether (100 mL) and washed with water (3×20 mL), and brine (2×10 mL), then dried (Na$_2$SO$_4$), filtered, concentrated and purified by CombiFlash chromatography (120 g column, eluting with 0-25% EtOAc/hexanes). LC/MS: 260.2 (M−Boc+2H).

Step 2. tert-Butyl (3R)-3-{[tert-butyl(dimethyl)silyl] oxy}-7-cyclohexyl-6-oxo-1,7-diazaspiro[4.4]nonane-1-carboxylate

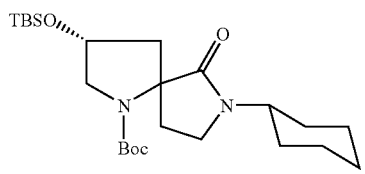

1-tert-Butyl 2-methyl (4R)-4-{[tert-butyl(dimethyl)silyl] oxy}-2-[2-(cyclohexylamino)ethyl]pyrrolidine-1,2-dicarboxylate (542 mg, 1.12 mmol, prepared by using procedures that were analogous to those described for the synthesis of Example 1, steps 2-4) was dissolved in anhydrous 1,4-dioxane (20 mL). To this mixture was added potassium tert-butoxide in THF (1.0 M, 10 mL). After 2 h, the reaction mixture was diluted with EtOAc (15 mL) and washed with $H_2O$ (2×5 mL) and the resulting layers were separated. The aqueous phase was extracted with EtOAc (2×5 mL) and the combined organic phases were washed with brine (5 mL), then dried ($Na_2SO_4$), filtered, and concentrated in vacuo. The crude residue was purified by CombiFlash chromatography using a 40 g column and eluting with EtOAc/hexanes at the following % EtOAc/time: 0-20%/5 min., 20-40%/21 min., 40-55%/4 min. at a flow rate of ~40 mL/min. The eluent was collected in 16 mm tubes with a tube volume of ~13 mL. Analysis of the fractions was performed by LC/MS, which identified two peaks that were presumed to be the diastereomers. The first diastereomer that eluted off the column (peak 1) had an LC/MS spectra that showed a strong M+1H peak (m/e 453) and a very small fragment peak at 397 (M−t-Bu) which provided 28 mg of material. The second diastereomer to elute (peak 2) had an LC/MS spectra that had a base peak of 353 (M−Boc+2H) in addition to peaks at 397 (M−t-Bu+2H), 453 (M+1H), and 475 (M+Na) and provided 185 mg of material.

Step 3

(3R)-1-(4-Chlorobenzyl)-7-cyclohexyl-3-hydroxy-1,7-diazaspiro[4.4]nonan-6-one was prepared by first treating peak 1 and peak 2 (separately) with 1.1 equivalents of 1.0 M tetra-N-butylammonium fluoride (TBAF) in THF to remove the hydroxyl TBS protecting group followed by removal of the Boc moiety and subsequent reductive amination with 4-chlorobenzaldehyde using procedures analogous to those described for the synthesis of Example 1, steps 6-7. The product derived from peak 2 was found to have better enzymatic binding activity and therefore all 3-hydroxy-1,7-diazaspiro[4.4]nonan-6-one derivatives discussed hereafter were prepared from intermediate peak 2 as described above unless otherwise noted.

Example 33

(3R)-7-Cyclohexyl-1-(1-cyclohexylethyl)-3-hydroxy-1,7-diazaspiro[4.4]nonan-6-one This compound was prepared by using procedures that are analogous to those described for the synthesis of Example 32, steps 1-3. LC-MS: 349.2 $(M+1H)^+$.

Example 34

(3R)-7-Cyclohexyl-1-(cyclohexylmethyl)-3-hydroxy-1,7-diazaspiro[4.4]nonan-6-one

This compound was prepared by using procedures that are analogous to those described for the synthesis of Example 32, steps 1-3. LC-MS: 335.2 $(M+1H)^+$.

Example 35

(3R)-1-[2-(3-Bromophenyl)-1-methylethyl]-7-cyclohexyl-3-hydroxy-1,7-diazaspiro[4.4]nonan-6-on This compound was prepared by using procedures that are analogous to those described for the synthesis of Example 32, steps 1-3. LC-MS: 435.1/437.0 $(M+1H)^+$.

Example 36

(3R)-7-Cyclohexyl-1-(1-cyclopropylethyl)-3-hydroxy-1,7-diazaspiro[4.4]nonan-6-one This compound was prepared by using procedures that are analogous to those described for the synthesis of Example 32, steps 1-3. LC-MS: 307.1 $(M+1H)^+$.

Example 37

(3R)-1-(4-Bromobenzyl)-7-cyclohexyl-3-hydroxy-1,7-diazaspiro[4.4]nonan-6-one

This compound was prepared by using procedures that are analogous to those described for the synthesis of Example 32, steps 1-3. LC-MS: 407.1/409.1 $(M+1H)^+$.

Example 38

(3R)-1-(1-Cyclobutylethyl)-7-cyclohexyl-3-hydroxy-1,7-diazaspiro[4.4]nonan-6-one This compound was prepared by using procedures that are analogous to those described for the synthesis of Example 32, steps 1-3. LC-MS: 321.2 $(M+1H)^+$.

Example 39

3-{1-[(3R)-7-Cyclohexyl-3-hydroxy-6-oxo-1,7-diazaspiro[4.4]non-1-yl]ethyl}benzonitrile This compound was prepared by using procedures that are analogous to those described for the synthesis of Example 32, steps 1-3. LC-MS: 368.1 $(M+1H)^+$.

Example 40

(3R)-7-Cyclohexyl-3-hydroxy-1-[1-(3-methyl-2-oxotetrahydrofuran-3-yl)ethyl]-1,7-diazaspiro[4.4]nonan-6-one This compound was prepared by using procedures that are analogous to those described for the synthesis of Example 32, steps 1-3. LC-MS: 365.3 $(M+1H)^+$.

Example 41

5-(4-{[(3R)-7-Cyclohexyl-3-hydroxy-6-oxo-1,7-diazaspiro[4.4]non-1-yl]methyl}-2-fluorophenyl)-N-isopropylpyridine-2-carboxamide To a solution of (4-{[(3R)-7-cyclohexyl-3-hydroxy-6-oxo-1,7-diazaspiro[4.4]non-1-yl]-methyl}-2-fluorophenyl)boronic acid (24.0 mg, 0.0000614 mol; which was prepared by using procedures that were analogous to those described for the synthesis of Example 32, steps 1-3 using peak 2 from step 2) and 5-bromo-N-isopropylpyridine-2-carboxamide (18 mg, 0.000074 mol) in DMF (0.8 mL, 0.01 mol) was added [1,1'-bis(diphenylphosphino)ferrocene]dichloropalladium(II), complex with DCM (1:1) (3.01 mg, 3.68E-6 mol) and potassium carbonate (25 mg, 0.00018 mol). The resulting mixture was heated at 130° C. under an atmosphere of nitrogen for 16 h to afford the desired product which was purified by prep-HPLC. LC/MS: 509.2 $(M+1H)^+$.

Example 42

(3R)-7-Cyclohexyl-3-hydroxy-1-(4-pyridin-4-ylbenzyl)-1,7-diazaspiro[4.4]nonan-6-one A solution of sodium carbonate (10.0 mg, 0.0000943 mol) in water (0.1 mL) was added to a mixture of (3R)-1-(4-bromobenzyl)-7-cyclohexyl-3-hydroxy-1,7-diazaspiro[4.4]nonan-6-one (19.0 mg, 0.0000466 mol; prepared as Example 37), 4-pyridinylboronic acid (8.60 mg, 0.0000700 mol) and tetrakis(triphenylphosphine)palladium(0) (1.6 mg, 0.0000014 mol) in toluene (200 μL, 0.002 mol) and ethanol (100 μL, 0.002 mol). After stirring the mixture at 120° C. for 6 h, the inorganics were separated by filtration and the filtrate was diluted with methanol and adjusted to a pH of ~2.0 with TFA. The crude product was purified by prep. HPLC to afford the desired product. LC/MS 406.2 (M+1H)$^+$.

Example 43

5-(4-{[(3R)-7-Cyclohexyl-3-hydroxy-6-oxo-1,7-diazaspiro[4.4]non-1-yl]methyl}-phenyl)-N-ethylpyridine-2-carboxamide This compound was prepared by using procedures that are analogous to those described for the synthesis of Example 42. LC-MS: 477.2 (M+1H)$^+$.

Example 44

5-(4-{[(3R)-7-Cyclohexyl-3-hydroxy-6-oxo-1,7-diazaspiro[4.4]non-1-yl]methyl}-3-fluorophenyl)-N-ethylpyridine-2-carboxamide This compound was prepared by using procedures that are analogous to those described for the synthesis of Example 42. LC-MS: 495.2 (M+1H)$^+$.

Example 45

(3R)-1-[1-(4-Bromophenyl)ethyl]-7-cyclohexyl-3-hydroxy-1,7-diazaspiro[4.4]-nonan-6-one A mixture of (3R)-7-cyclohexyl-3-hydroxy-1,7-diazaspiro[4.4]nonan-6-one (0.030 g, 0.00012 mol; which was prepared by using procedures analogous to those described for the synthesis of Example 32, derived from peak 2 of step 2), 1-(4-bromophenyl)ethyl methanesulfonate (0.053 g, 0.00019 mol) and potassium carbonate (0.035 g, 0.00025 mol) in dimethylsulfonamide (DMSO) (1.0 mL, 0.014 mol) was stirred at 100° C. for 16 h. The crude reaction mixture was purified by prep. HPLC to afford the desired product. LC-MS: 421.0/423.0 (M+1H)$^+$.

Example 46

(3R)-7-Cyclohexyl-1-[(2-fluorobiphenyl-4-yl)methyl]-3-hydroxy-1,7-diazaspiro-[4.4]nonan-6-one This compound was prepared by using procedures that are analogous to those described for the synthesis of Example 42. LC-MS: 423.1 (M+1H)$^+$.

Example 47

(3R)-7-Cyclohexyl-3-hydroxy-1-{3-[3-(trifluoromethyl)phenoxy]benzyl}-1,7-diazaspiro[4.4]nonan-6-one This compound was prepared by using procedures that are analogous to those described for the synthesis of Example 32. LC-MS: 489.1 (M+1H)$^+$.

Example 48

(3R)-7-Cyclohexyl-1-[4-(dimethylamino)benzyl]-3-hydroxy-1,7-diazaspiro[4.4]-nonan-6-one This compound was prepared by using procedures that are analogous to those described for the synthesis of Example 32. LC-MS: 372.2 (M+1H)$^+$.

Example 49

(3R)-7-Cyclohexyl-3-hydroxy-1-(4-morpholin-4-ylbenzyl)-1,7-diazaspiro[4.4]-nonan-6-one This compound was prepared by using procedures that are analogous to those described for the synthesis of Example 32. LC-MS: 414.1 (M+1H)$^+$.

Example 50

(3R)-7-Cyclohexyl-3-hydroxy-1-[4-(pyrimidin-2-yloxy)benzyl]-1,7-diazaspiro[4.4]-nonan-6-one This compound was prepared by using procedures that are analogous to those described for the synthesis of Example 32. LC-MS: 423.1 (M+1H)$^+$.

Example 51

(3R)-7-Cyclohexyl-1-(3-fluorobenzyl)-3-hydroxy-1,7-diazaspiro[4.4]nonan-6-one

This compound was prepared by using procedures that are analogous to those described for the synthesis of Example 32. LC-MS: 347.2 (M+1H)$^+$.

Example 52

(3R)-7-Cyclohexyl-3-hydroxy-1-(4-nitrobenzyl)-1,7-diazaspiro[4.4]nonan-6-one

This compound was prepared by using procedures that are analogous to those described for the synthesis of Example 32. LC-MS: 374.2 (M+1H)$^+$.

Example 53

2-{[(3R)-7-Cyclohexyl-3-hydroxy-6-oxo-1,7-diazaspiro[4.4]non-1-yl]methyl}-benzonitrile This compound was prepared by using procedures that are analogous to those described for the synthesis of Example 32. LC-MS: 354.1 (M+1H)$^+$.

Example 54

(3R)-7-Cyclohexyl-3-hydroxy-1-{4-[3-(trifluoromethyl)-1H-pyrazol-1-yl]benzyl}-1,7-diazaspiro[4.4]nonan-6-one To a solution of (3R)-1-(4-bromobenzyl)-7-cyclohexyl-3-hydroxy-1,7-diazaspiro[4.4]nonan-6-one (25.0 mg, 0.0000614 mol; prepared as in Example 37) in 1,4-dioxane (0.8 mL, 0.01 mol) was added (1S,2S)—N,N'-dimethylcyclohexane-1,2-diamine (1.7 mg, 0.000012 mol), copper(I) iodide (1.2 mg, 0.0000061 mol), and 3-(trifluoromethyl)-1H-pyrazole (17 mg, 0.00012 mol). After stirring the resulting mixture at 100° C. for 16 h, the crude reaction mixture was purified by prep.-HPLC under pH=10 conditions to afford the desired product. LC-MS: 463.2 $(M+1H)^+$.

Example 55

(3R)-7-Cyclohexyl-3-hydroxy-1-[4-(2-oxopyrrolidin-1-yl)benzyl]-1,7-diazaspiro-[4.4]nonan-6-one This compound was prepared by using procedures that are analogous to those described for the synthesis of Example 54. LC-MS: 412.2 $(M+1H)^+$.

Example 56

5-(5-{[(3R)-7-Cyclohexyl-3-hydroxy-6-oxo-1,7-diazaspiro[4.4]non-1-yl]methyl}-2-fluorophenyl)-N-ethylpyridine-2-carboxamide This compound was prepared by using procedures that are analogous to those described for the synthesis of Example 42. LC-MS: 495.2 $(M+1H)^+$.

Example 57

(3R)-7-Cyclohexyl-1-{[6-(4-fluorophenyl)pyridin-3-yl]methyl}-3-hydroxy-1,7-diazaspiro[4.4]nonan-6-one This compound was prepared by using procedures that are analogous to those described for the synthesis of Example 42. LC-MS: 424.2 $(M+1H)^+$.

Example 58

3-(5-{[(3R)-7-Cyclohexyl-3-hydroxy-6-oxo-1,7-diazaspiro[4.4]non-1-yl]methyl}-pyridin-2-yl)benzonitrile This compound was prepared by using procedures that are analogous to those described for the synthesis of Example 42. LC-MS: 431.2 $(M+1H)^+$.

Example 59

(3R)-7-Cyclohexyl-1-{[6-(3,5-dimethylisoxazol-4-yl)pyridin-3-yl]methyl}-3-hydroxy-1,7-diazaspiro[4.4]nonan-6-one This compound was prepared by using procedures that are analogous to those described for the synthesis of Example 42. LC-MS: 425.2 $(M+1H)^+$.

Example 60

5-(3-{[(3R)-7-Cyclohexyl-3-hydroxy-6-oxo-1,7-diazaspiro[4.4]non-1-yl]methyl}-phenyl)-N-ethylpyridine-2-carboxamide This compound was prepared by using procedures that are analogous to those described for the synthesis of Example 42. LC-MS: 477.2 $(M+1H)^+$.

Example 61

(3R)-7-Cyclohexyl-1-(1-ethylpropyl)-3-hydroxy-1,7-diazaspiro[4.4]nonan-6-one

This compound was prepared by using procedures that are analogous to those described for the synthesis of Example 42. LC-MS: 309.2 $(M+1H)^+$.

Example 62

(3R)-7-Cyclohexyl-1-cyclopentyl-3-hydroxy-1,7-diazaspiro[4.4]nonan-6-one

This compound was prepared by using procedures that are analogous to those described for the synthesis of Example 42. LC-MS: 307.3 $(M+1H)^+$.

Example 63

(3S)-1-(4-Chlorobenzyl)-7-cyclohexyl-3-hydroxy-1,7-diazaspiro[4.4]nonan-6-one

Step 1: (3S)-1-(4-Chlorobenzyl)-7-cyclohexyl-6-oxo-1,7-diazaspiro[4.4]non-3-ylacetate To a mixture of (3R)-1-(4-chlorobenzyl)-7-cyclohexyl-3-hydroxy-1,7-diazaspiro[4.4]nonan-6-one (25.0 mg, 0.0000689 mol (prepared as in Example 32 derived from peak 2 in step 2), triphenylphosphine (27 mg, 0.00010 mol), and acetic acid (50 μL, 0.0009 mol) in THF (2 mL, 0.03 mol) was added diisopropyl azodicarboxylate (22 μL, 0.00011 mol) at RT, and the resulting mixture was stirred for 16 h. The crude reaction mixture was purified by prep. HPLC/MS chromatography to afford the desired product. LC/MS: 405.1 $(M+1H)^+$.

Step 2

The acetate product of Step 3 was dissolved in methanol and treated with potassium carbonate at RT for 1 h. The crude reaction mixture was purified by prep. HPLC/MS chromatography to afford the desired product. LC/MS: 363.1 $(M+1H)^+$.

Example 64

(3R)-7-Cyclohexyl-1-(cyclopentylmethyl)-3-hydroxy-1,7-diazaspiro[4.4]nonan-6-one This compound was prepared by using procedures that are analogous to those described for the synthesis of Example 32. LC-MS: 321.3 $(M+1H)^+$.

Example 65

5-(4-{[(3R)-7-Cyclohexyl-3-hydroxy-6-oxo-1,7-diazaspiro[4.4]non-1-yl]methyl}-2-fluorophenyl)-N,N-dimethylpyridine-2-carboxamide This compound was prepared by using procedures that are analogous to those described for the synthesis of Example 41. LC-MS: 495.2 (M+1H)$^+$.

Example 66

5-(4-{[(3R)-7-Cyclohexyl-3-hydroxy-6-oxo-1,7-diazaspiro[4.4]non-1-yl]methyl}-phenyl)-N,N-dimethylpyridine-2-carboxamide This compound was prepared by using procedures that are analogous to those described for the synthesis of Example 42. LC-MS: 477.2 (M+1H)$^+$.

Example 67

2-(4-{[(3R)-7-Cyclohexyl-3-hydroxy-6-oxo-1,7-diazaspiro[4.4]non-1-yl]methyl}-phenyl)isonicotinonitrile This compound was prepared by using procedures that are analogous to those described for the synthesis of Example 42. LC/MS: 431.2 (M+1H)$^+$.

Example 68

(3R)-1-[4-(5-Chloropyridin-3-yl)benzyl]-7-cyclohexyl-3-hydroxy-1,7-diazaspiro-[4.4]nonan-6-one This compound was prepared by using procedures that are analogous to those described for the synthesis of Example 42. LC/MS: 440.1 (M+1H)$^+$.

Example 69

3-(4-{[(3R)-7-Cyclohexyl-3-hydroxy-6-oxo-1,7-diazaspiro[4.4]non-1-yl]methyl}-phenyl)pyrazine-2-carbonitrile This compound was prepared by using procedures that are analogous to those described for the synthesis of Example 42. LC/MS: 432.1 (M+1H)$^+$.

Example 70

(3R)-7-Cyclohexyl-1-[4-(3-fluoropyridin-4-yl)benzyl]-3-hydroxy-1,7-diazaspiro-[4.4]nonan-6-one This compound was prepared by using procedures that are analogous to those described for the synthesis of Example 42. LC/MS: 424.2 (M+1H)$^+$.

Example 71

(3R)-7-Cyclohexyl-3-hydroxy-1-(4-pyrazin-2-ylbenzyl)-1,7-diazaspiro[4.4]nonan-6-one This compound was prepared by using procedures that are analogous to those described for the synthesis of Example 42. LC/MS: 407.1 (M+1H)$^+$.

Example 72

(3R)-1-[2-(4-Bromophenyl)ethyl]-7-cyclohexyl-3-hydroxy-1,7-diazaspiro[4.4]-nonan-6-one This compound was prepared by using procedures that are analogous to those described for the synthesis of Example 32. LC/MS: 421.1/423.1 (M+1H)$^+$.

Example 73

(3R)-7-Cyclohexyl-1-{[5-(3,4-difluorophenyl)pyridin-2-yl]methyl}-3-hydroxy-1,7-diazaspiro[4.4]nonan-6-one This compound was prepared by using procedures that are analogous to those described for the synthesis of Example 42. LC/MS: 442.2 (M+1H)$^+$.

Example 74

3-(6-{[(3R)-7-Cyclohexyl-3-hydroxy-6-oxo-1,7-diazaspiro[4.4]non-1-yl]methyl}-pyridin-3-yl)benzonitrile This compound was prepared by using procedures that are analogous to those described for the synthesis of Example 42. LC/MS: 431.2 M+1H)$^+$.

Example 75

6'-{[(3R)-7-Cyclohexyl-3-hydroxy-6-oxo-1,7-diazaspiro[4.4]non-1-yl]methyl}-N-methyl-3,3'-bipyridine-6-carboxamide This compound was prepared by using procedures that are analogous to those described for the synthesis of Example 42. LC/MS: 464.2 (M+1H)$^+$.

Example 76

(3R)-1-{[1-(4-Chlorophenyl)cyclopropyl]methyl}-7-cyclohexyl-3-hydroxy-1,7-diazaspiro[4.4]nonan-6-one This compound was prepared by using procedures that are analogous to those described for the synthesis of Example 32. LC/MS: 403.2 (M+1H)$^+$.

Example 77

4-(6-{[(3R)-7-Cyclohexyl-3-hydroxy-6-oxo-1,7-diazaspiro[4.4]non-1-yl]methyl}-pyridin-3-yl)-N-cyclopropylbenzamide This compound was prepared by using procedures that are analogous to those described for the synthesis of Example 42. LC/MS: 489.2 (M+1H)$^+$.

Example 78

(3R)-7-Cyclohexyl-1-(cyclopropylmethyl)-3-hydroxy-1,7-diazaspiro[4.4]nonan-6-one This compound was prepared by using procedures that are analogous to those described for the synthesis of Example 32. LC/MS: 293.2 (M+1H)$^+$.

Example 79

1-(4-Chlorobenzyl)-7-cyclohexyl-3-hydroxy-3-methyl-1,7-diazaspiro[4.4]nonan-6-one

Step 1: 1-(4-Chlorobenzyl)-7-cyclohexyl-1,7-diazaspiro[4.4]nonane-3,6-dione

Dess-Martin periodinane (0.19 g, 0.00044 mol) was added to a solution of (3R)-1-(4-chloro-benzyl)-7-cyclohexyl-3-hydroxy-1,7-diazaspiro[4.4]nonan-6-one (0.080 g, 0.00022 mol; prepared as in Example 32, derived from peak 2 of step 2) in DCM (2.0 mL, 0.031 mol). The resulting mixture was stirred for 3 h at RT. The mixture was then diluted with ethyl acetate and stirred with $Na_2S_2O_3$ followed by saturated $NaHCO_3$. Following separation of the organic and aqueous layers, the organic layer was dried and concentrated in vacuo to afford the desired product. LC/MS: 361.1 $(M+1H)^+$.

Step 2

2-Methylallylmagnesium chloride in THF (3.0 M, 0.074 mL) was added to a solution of 1-(4-chlorobenzyl)-7-cyclohexyl-1,7-diazaspiro[4.4]nonane-3,6-dione (0.040 g, 0.00011 mol) in THF (1.0 mL, 0.012 mol) and the resulting mixture was stirred at 50° C. for 1 h. The reaction mixture was then allowed to cool to RT and was then quenched by the addition of saturated $NH_4Cl$. The crude reaction mixture was purified by prep. HPLC to afford the desired product. LC/MS: 377.2 $(M+1H)^+$.

Example 80

1-(4-Chlorobenzyl)-7-cyclohexyl-3,3-difluoro-1,7-diazaspiro[4.4]nonan-6-one

Diethylaminosulfur trifluoride (37 μL, 0.00028 mol) was added to a solution of 1-(4-chlorobenzyl)-7-cyclohexyl-1,7-diazaspiro[4.4]nonane-3,6-dione (0.020 g, 0.000055 mol; prepared as in Example 79, step 1) in DCM (1.0 mL, 0.016 mol) at −78° C. The resulting mixture was allowed to gradually warm to RT and was stirred for 16 h. The crude reaction mixture was purified by prep. HPLC to afford the desired product. LC/MS: 383.1 $(M+1H)^+$.

Example 81

(3S)-1-(4-Chlorobenzyl)-7-cyclohexyl-3-fluoro-1,7-diazaspiro[4.4]nonan-6-one

Diethylaminosulfur trifluoride (11 μL, 0.000083 mol) was added to a solution of (3R)-1-(4-chlorobenzyl)-7-cyclohexyl-3-hydroxy-1,7-diazaspiro[4.4]nonan-6-one (10.0 mg, 0.0000276 mol; prepared as in Example 32, derived from peak 2 of step 2) in DCM (1.0 mL, 0.016 mol) at −78° C. The mixture was allowed to gradually warm to RT and stirred for 2 h. The crude reaction mixture was purified by prep. HPLC to afford the desired product. LC/MS: 365.1 $(M+1H)^+$.

Example 82

5-(4-{[(3S)-7-Cyclohexyl-3-fluoro-6-oxo-1,7-diazaspiro[4.4]non-1-yl]methyl}-phenyl)-N-methylpyridine-2-carboxamide 5-(4-{[(3R)-7-Cyclohexyl-3-hydroxy-6-oxo-1,7-diazaspiro[4.4]non-1-yl]methyl}phenyl)-N-methylpyridine-2-carboxamide (prepared according to a procedure analogous to that described for the synthesis of Example 42) was treated with diethylaminosulfur trifluoride as outlined in the synthesis of Example 81 to afford the desired product. LC/MS: 465.2 $(M+1H)^+$.

Example 83

1-(4-Chlorobenzyl)-7-cycloheptyl-1,7-diazaspiro[4.4]nonan-6-one

This compound was prepared by using procedures that are analogous to those described for the synthesis of Example 1, steps 1-7. LC/MS: 361.3 $(M+1H)^+$.

Example 84

1-(4-Chlorobenzyl)-7-cyclopentyl-1,7-diazaspiro[4.4]nonan-6-one

This compound was prepared by using procedures that are analogous to those described for the synthesis of Example 1, steps 1-7. LC/MS: 333.2 $(M+1H)^+$.

Example 85

5-{4-[(7-Cyclohexyl-6-oxo-1,7-diazaspiro[4.4]non-1-yl)methyl]phenyl}-N-ethyl-pyridine-2-carboxamide To a solution of 1-(4-bromobenzyl)-7-cyclohexyl-1,7-diazaspiro[4.4]nonan-6-one (15 mg, 0.000038 mol; prepared according to procedures analogous to those described for the synthesis of Example 1, steps 1-7) in 1,4-dioxane (1 mL, 0.01 mol) and ethanol (200 μL, 0.003 mol) was added sequentially: {6-[(ethylamino)carbonyl]pyridin-3-yl}boronic acid (15 mg, 0.000077 mol), [1,1'-bis(diphenylphosphino)ferrocene]dichloropalladium(II), complex with DCM (1:1) (3 mg, 0.000004 mol), potassium carbonate (1.0 E1 mg, 0.000077 mol), and water (400 μL, 0.02 mol). The resulting mixture was made in a vial which was then sealed, evacuated, and purged with $N_2$ (g). The mixture was then heated to 90° C. and stirred for 16 h. The crude reaction mixture was then purified by prep. HPLC/MS to afford the desired product. LC/MS: 461.3 $(M+1H)^+$.

Example 86

7-Cyclohexyl-1-[4-(5-methoxypyridin-3-yl)benzyl]-1,7-diazaspiro[4.4]nonan-6-one

This compound was prepared by using procedures that are analogous to those described for the synthesis of Example 85. LC/MS: 420.2 $(M+1H)^+$.

Example 87

7-Cyclohexyl-1-(4-pyridin-4-ylbenzyl)-1,7-diazaspiro[4.4]nonan-6-one

This compound was prepared by using procedures that are analogous to those described for the synthesis of Example 85. LC/MS: 390.2 $(M+1H)^+$.

Example 88

7-Cyclohexyl-1-[4-(difluoromethoxy)benzyl]-1,7-diazaspiro[4.4]nonan-6-one

This compound was prepared by using procedures that are analogous to those described for the synthesis of Example 1. LC/MS: 379.2 (M+1H)$^+$.

Example 89

7-Cyclohexyl-1-[(6-methoxypyridin-3-yl)methyl]-1,7-diazaspiro[4.4]nonan-6-one

This compound was prepared by using procedures that are analogous to those described for the synthesis of Example 1. LC/MS: 344.2 (M+1H)$^+$.

Example 90

7-Cyclohexyl-1-(4-phenoxybenzyl)-1,7-diazaspiro[4.4]nonan-6-one

This compound was prepared by using procedures that are analogous to those described for the synthesis of Example 1. LC/MS: 405.2 (M+1H)$^+$.

Example 91

7-Cyclohexyl-1-[4-(trifluoromethyl)benzyl]-1,7-diazaspiro[4.4]nonan-6-one

This compound was prepared by using procedures that are analogous to those described for the synthesis of Example 1. LC/MS: 381.3 (M+1H)$^+$.

Example 92

5-[(7-Cyclohexyl-6-oxo-1,7-diazaspiro[4.4]non-1-yl)methyl]-2-fluorobenzonitrile

This compound was prepared by using procedures that are analogous to those described for the synthesis of Example 1. LC/MS: 356.1 (M+1H)$^+$.

Example 93

7-Cyclohexyl-1-[4-(methylsulfonyl)benzyl]-1,7-diazaspiro[4.4]nonan-6-one

This compound was prepared by using procedures that are analogous to those described for the synthesis of Example 1. LC/MS: 391.2 (M+1H)$^+$.

Example 94

7-Cyclohexyl-1-[(1-methyl-1H-pyrrol-2-yl)methyl]-1,7-diazaspiro[4.4]nonan-6-one

This compound was prepared by using procedures that are analogous to those described for the synthesis of Example 1. LC/MS 316.3 (M+1H)$^+$.

Example 95

1-[2-Chloro-4-(methylsulfonyl)benzyl]-7-cyclohexyl-1,7-diazaspiro[4.4]nonan-6-one This compound was prepared by using procedures that are analogous to those described for the synthesis of Example 1. LC/MS 425.2 (M+1H)$^+$.

Example 96

N-{4-[(7-Cyclohexyl-6-oxo-1,7-diazaspiro[4.4]non-1-yl)methyl]phenyl}acetamide

This compound was prepared by using procedures that are analogous to those described for the synthesis of Example 1. LC/MS 370.2 (M+1H)$^+$.

Example 97

1-(Biphenyl-4-ylmethyl)-7-cyclohexyl-1,7-diazaspiro[4.4]nonan-6-one

This compound was prepared by using procedures that are analogous to those described for the synthesis of Example 1. LC/MS 389.2 (M+1H)$^+$.

Example 98

1-(Biphenyl-2-ylmethyl)-7-cyclohexyl-1,7-diazaspiro[4.4]nonan-6-one

This compound was prepared by using procedures that are analogous to those described for the synthesis of Example 1. LC/MS 389.2 (M+1H)$^+$.

Example 99

7-Cyclohexyl-1-(1,2,3-thiadiazol-4-ylmethyl)-1,7-diazaspiro[4.4]nonan-6-one

This compound was prepared by using procedures that are analogous to those described for the synthesis of Example 1. LC/MS 321.2 (M+1H)$^+$.

Example 100

1-(4-Chlorobenzyl)-7-(2-methoxybenzyl)-1,7-diazaspiro[4.4]nonan-6-one

This compound was prepared by using procedures that are analogous to those described for the synthesis of Example 1. LC/MS 385.2 (M+1H)$^+$.

Example 101

1-(4-Chlorobenzyl)-7-(trans-4-hydroxycyclohexyl)-1,7-diazaspiro[4.4]nonan-6-one

This compound was prepared by using procedures that are analogous to those described for the synthesis of Example 1. LC/MS 363.3 (M+1H)$^+$.

Example 102

1-(4-Chlorobenzyl)-7-(tetrahydro-2H-pyran-4-yl)-1,7-diazaspiro[4.4]nonan-6-one

This compound was prepared by using procedures that are analogous to those described for the synthesis of Example 1. LC/MS 349.2 (M+1H)$^+$.

Example 103

1-(4-Fluorobenzyl)-7-(tetrahydro-2H-pyran-4-yl)-1,7-diazaspiro[4.4]nonan-6-one

This compound was prepared by using procedures that are analogous to those described for the synthesis of Example 1. LC/MS 333.2 (M+1H)$^+$.

Example 104

7-Cyclohexyl-1-(cyclopropylmethyl)-1,7-diazaspiro[4.4]nonan-6-one

This compound was prepared by using procedures that are analogous to those described for the synthesis of Example 1. LC/MS 277.2 (M+1H)$^+$.

Example 105

7-Cyclohexyl-1-(pyridin-3-ylmethyl)-1,7-diazaspiro[4.4]nonan-6-one

This compound was prepared by using procedures that are analogous to those described for the synthesis of Example 1. LC/MS 314.2 (M+1H)$^+$.

Example 106

7-Cyclohexyl-1-(pyridin-2-ylmethyl)-1,7-diazaspiro[4.4]nonan-6-one

This compound was prepared by using procedures that are analogous to those described for the synthesis of Example 1. LC/MS 314.2 (M+1H)$^+$.

Example 107

7-Cyclohexyl-1-(pyridin-4-ylmethyl)-1,7-diazaspiro[4.4]nonan-6-one

This compound was prepared by using procedures that are analogous to those described for the synthesis of Example 1. LC/MS 314.2 (M+1H)$^+$.

Example 108

7-Cyclohexyl-1-[(1-methyl-1H-imidazol-2-yl)methyl]-1,7-diazaspiro[4.4]nonan-6-one This compound was prepared by using procedures that are analogous to those described for the synthesis of Example 1. LC/MS 317.1 (M+1H)$^+$.

Example 109

7-Cyclohexyl-1-[(2,5-dimethyl-1,3-thiazol-4-yl)methyl]-1,7-diazaspiro[4.4]nonan-6-one This compound was prepared by using procedures that are analogous to those described for the synthesis of Example 1. LC/MS 348.1 (M+1H)$^+$.

Example 110

7-Cyclohexyl-1-[4-(1,2,3-thiadiazol-4-yl)benzyl]-1,7-diazaspiro[4.4]nonan-6-one

This compound was prepared by using procedures that are analogous to those described for the synthesis of Example 1. LC/MS 397.1 (M+1H)$^+$.

Example 111

1-(4-Chlorobenzyl)-7-(2-methoxy-1-methylethyl)-1,7-diazaspiro[4.4]nonan-6-one

This compound was prepared by using procedures that are analogous to those described for the synthesis of Example 1. LC/MS 337.2 (M+1H)$^+$.

Example 112

1-(4-Chlorobenzyl)-7-(pyridin-4-ylmethyl)-1,7-diazaspiro[4.4]nonan-6-one

This compound was prepared by using procedures that are analogous to those described for the synthesis of Example 1. LC/MS 356.1 (M+1H)$^+$.

Example A

Enzymatic Assay of 11βHSD1

All in vitro assays were performed with clarified lysates as the source of 11βHSD1 activity. HEK-293 transient transfectants expressing an epitope-tagged version of full-length human 11βHSD1 were harvested by centrifugation. Roughly 2×10$^7$ cells were resuspended in 40 mL of lysis buffer (25 mM Tris-HCl, pH 7.5, 0.1 M NaCl, 1 mM MgCl$_2$ and 250 mM sucrose) and lysed in a microfluidizer. Lysates were clarified by centrifugation and the supernatants were aliquoted and frozen.

Inhibition of 11βHSD1 by test compounds was assessed in vitro by a Scintillation Proximity Assay (SPA). Dry test compounds were dissolved at 5 mM in DMSO. These were diluted in DMSO to suitable concentrations for the SPA assay. 0.8 μL of 2-fold serial dilutions of compounds were dotted on 384 well plates in DMSO such that 3 logs of compound concentration were covered. 20 μL of clarified lysate was added to each well. Reactions were initiated by addition of 20 μL of substrate-cofactor mix in assay buffer (25 mM Tris-HCl, pH 7.5, 0.1 M NaCl, 1 mM MgCl$_2$) to final concentrations of 400 μM NADPH, 25 nM $^3$H-cortisone and 0.007% Triton X-100. Plates were incubated at 37° C. for one hour. Reactions were quenched by addition of 40 μL of anti-mouse coated SPA beads that had been pre-incubated with 10 μM carbenoxolone and a cortisol-specific monoclonal antibody. Quenched plates were incubated for a minimum of 30 minutes at RT prior to reading on a Topcount scintillation counter. Controls with no lysate, inhibited lysate, and with no mAb were run routinely.

Roughly 30% of input cortisone is reduced by 11βHSD1 in the uninhibited reaction under these conditions.

Test compounds having an $IC_{50}$ value less than about 20 μM according to this assay were considered active.

Example B

Cell-Based Assays for HSD Activity

Peripheral blood mononuclear cells (PBMCs) were isolated from normal human volunteers by Ficoll density centrifugation. Cells were plated at $4 \times 10^5$ cells/well in 200 μL of AIM V (Gibco-BRL) media in 96 well plates. The cells were stimulated overnight with 50 ng/mL recombinant human IL-4 (R&D Systems). The following morning, 200 nM cortisone (Sigma) was added in the presence or absence of various concentrations of compound. The cells were incubated for 48 hours and then supernatants were harvested. Conversion of cortisone to cortisol was determined by a commercially available ELISA (Assay Design).

Test compounds having an $IC_{50}$ value less than about 20 μM according to this assay were considered active.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A compound of Formula III:

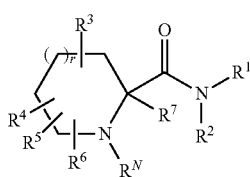

or pharmaceutically acceptable salt thereof, wherein:

$R^N$ is H, $C_{1-6}$ alkyl, $C_{2-6}$ alkenyl, $C_{2-6}$ alkynyl, —C(O)—$R^{8a}$, —C(O)O—$R^{8b}$, —$SO_q$—$R^{8a}$, —$(CR^{1a}R^{1b})_a$-$Cy^1$, or —$(CR^{1a}R^{1b})_a$—C(O)—$(CR^{1a}R^{1b})_b$-$Cy^1$, wherein said $C_{1-6}$ alkyl, $C_{2-6}$ alkenyl, or $C_{2-6}$ alkynyl is optionally substituted by 1, 2, 3, 4, or 5 substituents independently selected from halo, $C_{1-4}$ alkyl, $C_{1-4}$ haloalkyl, aryl, cycloalkyl, heteroaryl, heterocycloalkyl, arylalkyl, cycloalkylalkyl, heteroarylalkyl, heterocycloalkylalkyl, halosulfanyl, CN, $N_3$, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{d1}$, $NR^{c1}C(O)OR^{a1}$, $S(O)R^{b1}$, $S(O)NR^{c1}R^{d1}$, $S(O)_2R^{b1}$, and $S(O)_2NR^{c1}R^{d1}$;

$R^1$ is $C_{1-6}$ alkyl, $C_{2-12}$ alkoxyalkyl, or —$(CR^{2a}R^{2b})_c$-$Cy^2$;

$R^2$ together with $R^7$ form —$CH_2$—$CH_2$—;

$R^3$, $R^4$, $R^5$, and $R^6$ are independently selected from H, halo, $C_{1-4}$ alkyl, $C_{1-4}$ haloalkyl, $C_{2-6}$ alkenyl, $C_{2-6}$ alkynyl, —$(CR^{1a}R^{1b})_a$-$Cy^4$, halosulfanyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^cC(O)OR^a$, $S(O)R^b$, $S(O)NR^cR^d$, $S(O)_2R^b$, and $S(O)_2NR^cR^d$, wherein said $C_{1-4}$ alkyl, $C_{2-6}$ alkenyl, or $C_{2-6}$ alkynyl are optionally substituted with 1, 2 or 3 substituents selected from halo, halosulfanyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^cC(O)OR^a$, $S(O)R^b$, $S(O)NR^cR^d$, $S(O)_2R^b$, and $S(O)_2NR^cR^d$;

or two of $R^3$, $R^4$, $R^5$, and $R^6$ are attached to the same atom of ring A and together with the atom to which they are attached form a 3-20 membered cycloalkyl group or 3-20 membered heterocycloalkyl group, each optionally substituted by 1, 2, or 3 substituents independently selected from halo, $C_{1-4}$ alkyl, $C_{1-4}$ haloalkyl, aryl, cycloalkyl, heteroaryl, heterocycloalkyl, halosulfanyl, CN, $NO_2$, $OR^1$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^cC(O)OR^a$, $S(O)R^b$, $S(O)NR^cR^d$, $S(O)_2R^b$, and $S(O)_2NR^cR^d$;

$R^{8a}$ is H, $C_{1-6}$ alkyl, $NR^{c1}R^{d1}$, or $Cy^3$, wherein said $C_{1-6}$ alkyl is optionally substituted by 1, 2, 3, 4 or 5 substituents independently selected from halo, $C_{1-4}$ alkyl, $C_{1-4}$ haloalkyl, aryl, cycloalkyl, heteroaryl, heterocycloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{d1}$, $NR^{c1}C(O)OR^{a1}$, $S(O)R^{b1}$, $S(O)NR^{c1}R^{d1}$, $S(O)_2R^{b1}$, and $S(O)_2NR^{c1}R^{d1}$;

$R^{8b}$ is H, $C_{1-6}$ alkyl, or $Cy^3$, wherein said $C_{1-6}$ alkyl is optionally substituted by 1, 2, 3, 4 or 5 substituents independently selected from halo, $C_{1-4}$ alkyl, $C_{1-4}$ haloalkyl, aryl, cycloalkyl, heteroaryl, heterocycloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{d1}$, $NR^{c1}C(O)OR^{a1}$, $S(O)R^{b1}$, $S(O)NR^{c1}R^{d1}$, $S(O)_2R^{b1}$ and $S(O)_2NR^{c1}R^{d1}$;

$Cy^1$, $Cy^2$, $Cy^3$, and $Cy^4$ are independently selected from aryl, heteroaryl, cycloalkyl, and heterocycloalkyl, each optionally substituted by 1, 2, 3, 4 or 5 substituents independently selected from $Cy^5$, halo, $C_{1-4}$ alkyl, $C_{2-4}$ alkenyl, $C_{2-4}$ alkynyl, $C_{1-4}$ haloalkyl, halosulfanyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $S(O)R^{b3}$, $S(O)NR^{c3}R^{d3}$, $S(O)_2R^{b3}$, and $S(O)_2NR^{c3}R^{d3}$;

$Cy^5$ is aryl, heteroaryl, cycloalkyl, and heterocycloalkyl, each optionally substituted by 1, 2, 3, 4 or 5 substituents independently selected from halo, $C_{1-4}$ alkyl, $C_{2-4}$ alkenyl, $C_{2-4}$ alkynyl, $C_{1-4}$ haloalkyl, halosulfanyl, CN, $NO_2$, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)OR^{a6}$, $S(O)R^{b6}$, $S(O)NR^{c6}R^{d6}$, $S(O)_2R^{b6}$, and $S(O)_2NR^{c6}R^{d6}$;

$R^{1a}$ and $R^{1b}$ are independently selected from H, halo, $C_{1-4}$ alkyl, $C_{2-4}$ alkenyl, $C_{2-4}$ alkynyl, $C_{1-4}$ alkoxy, $C_{1-4}$ haloalkyl, $C_{1-4}$ haloalkoxy, OH, amino, $C_{1-4}$ alkylamino, and $C_{2-8}$ dialkylamino;

$R^{2a}$ and $R^{2b}$ are independently selected from halo, $C_{1-4}$ alkyl, $C_{2-4}$ alkenyl, $C_{2-4}$ alkynyl, $C_{1-4}$ alkoxy, $C_{1-4}$ haloalkyl, $C_{1-4}$ haloalkoxy, OH, amino, $C_{1-4}$ alkylamino, and $C_{2-8}$ dialkylamino;

$R^a$, $R^{a1}$ and $R^{a3}$ are independently selected from H, $C_{1-6}$ alkyl, $C_{1-6}$ haloalkyl, $C_{2-6}$ alkenyl, $C_{2-6}$ alkynyl, $Cy^5$, and —($C_{1-6}$ alkyl)-$Cy^5$, wherein said $C_{1-6}$ alkyl, $C_{1-6}$ haloalkyl, $C_{2-6}$ alkenyl, or $C_{2-6}$ alkynyl is optionally substituted with 1, 2, or 3 substituents independently selected from OH, CN, amino, halo, $C_{1-6}$ alkyl, $C_{1-6}$ haloalkyl, aryl, arylalkyl, heteroaryl, heteroarylalkyl, cycloalkyl and heterocycloalkyl;

$R^b$, $R^{b1}$, $R^{b2}$, $R^{b3}$ are independently selected from H, $C_{1-6}$ alkyl, $C_{1-6}$ haloalkyl, $C_{2-6}$ alkenyl, $C_{2-6}$ alkynyl, $Cy^5$, and —($C_{1-6}$ alkyl)-$Cy^5$, wherein said $C_{1-6}$ alkyl, $C_{1-6}$ haloalkyl, $C_{2-6}$ alkenyl, or $C_{2-6}$ alkynyl is optionally substituted with 1, 2, or 3 substituents independently selected from OH, CN, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl and heterocycloalkyl;

$R^c$, $R^{c1}$, $R^{c2}$, $R^{c3}$, $R^d$, $R^{d1}$ and $R^{d3}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl and heterocycloalkyl;

or $R^c$ and $R^d$ together with the N atom to which they are attached form a 4-, 5-, 6- or 7-membered heterocycloalkyl group optionally substituted with 1, 2, or 3 substituents independently selected from OH, CN, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl or heterocycloalkyl;

or $R^{c1}$ and $R^{d1}$ together with the N atom to which they are attached form a 4-, 5-, 6- or 7-membered heterocycloalkyl group optionally substituted with 1, 2, or 3 substituents independently selected from OH, CN, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl and heterocycloalkyl;

or $R^{c3}$ and $R^{d3}$ together with the N atom to which they are attached form a 4-, 5-, 6- or 7-membered heterocycloalkyl group optionally substituted with 1, 2, or 3 substituents independently selected from OH, CN, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl and heterocycloalkyl;

$R^{a6}$ is H, $C_{1-6}$ alkyl, $C_{1-6}$ haloalkyl, $C_{2-6}$ alkenyl, or $C_{2-6}$ alkynyl, wherein said $C_{1-6}$ alkyl, $C_{1-6}$ haloalkyl, $C_{2-6}$ alkenyl, or $C_{2-6}$ alkynyl is optionally substituted with 1, 2, or 3 substituents independently selected from OH, CN, amino, halo, $C_{1-6}$ alkyl, $C_{1-6}$ haloalkyl, aryl, arylalkyl, heteroaryl, heteroarylalkyl, cycloalkyl and heterocycloalkyl;

$R^{b6}$ is H, $C_{1-6}$ alkyl, $C_{1-6}$ haloalkyl, $C_{2-6}$ alkenyl, or $C_{2-6}$ alkynyl, wherein said $C_{1-6}$ alkyl, $C_{1-6}$ haloalkyl, $C_{2-6}$ alkenyl, or $C_{2-6}$ alkynyl is optionally substituted with 1, 2, or 3 substituents independently selected from OH, CN, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl and heterocycloalkyl;

$R^{c6}$ and $R^{d6}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl and heterocycloalkyl;

or $R^{c6}$ and $R^{d6}$ together with the N atom to which they are attached form a 4-, 5-, 6- or 7-membered heterocycloalkyl group optionally substituted with 1, 2, or 3 substituents independently selected from OH, CN, amino, halo, $C_{1-6}$ alkyl, $C_{1-6}$ haloalkyl, $C_{1-6}$ haloalkyl, aryl, arylalkyl, heteroaryl, heteroarylalkyl, cycloalkyl or heterocycloalkyl;

a, b, and c are independently selected from 0, 1, 2, 3, 4, and 5;

q is 0, 1, or 2; and r is 0, 1, or 2.

2. The compound of claim 1, or pharmaceutically acceptable salt thereof, wherein $R^N$ is $C_{1-6}$ alkyl, —C(O)—$R^{8a}$, —C(O)O—$R^{8b}$, —$SO_q$—$R^{8a}$, —$(CR^{1a}R^{1b})_a$-$Cy^1$, or —$(CR^{1a}R^{1b})_a$—C(O)—$(CR^{1a}R^{1b})_b$-$Cy^1$.

3. The compound of claim 1, or pharmaceutically acceptable salt thereof, wherein $R^N$ is $C_{1-4}$ alkyl, cycloalkylalkyl, heterocycloalkylalkyl, arylalkyl, heteroarylalkyl, aryl, heteroaryl, arylsulfonyl, alkylsulfonyl, —C(O)O—($C_{1-4}$ alkyl), —C(O)-aryl, —C(O)-heteroaryl, or —C(O)-cycloalkyl, each optionally substituted by 1, 2 or 3 substituents independently selected from halo, $C_{1-4}$ alkyl, $C_{1-4}$ haloalkyl, $C_{1-4}$ haloalkoxy, CN, and $NO_2$.

4. The compound of claim 1, or pharmaceutically acceptable salt thereof, wherein $R^3$, $R^4$, $R^5$, and $R^6$ are independently selected from H, halo, $C_{1-4}$ alkyl, $C_{1-4}$ haloalkyl, $OR^a$, or $OC(O)R^b$.

5. The compound of claim 1, or pharmaceutically acceptable salt thereof, wherein $R^3$, $R^4$, $R^5$, and $R^6$ are independently selected from H, F, Me, or OH.

6. The compound of claim 1, or pharmaceutically acceptable salt thereof, wherein $R^3$, $R^4$, $R^5$, and $R^6$ are each H.

7. The compound of claim 1, or pharmaceutically acceptable salt thereof, wherein two of $R^3$, $R^4$, $R^5$, and $R^6$ are attached to the same atom and together with the atom to which they are attached form a 3-20 membered cycloalkyl group or 3-20 membered heterocycloalkyl group, each optionally substituted by 1, 2, or 3 substituents independently selected from halo, $C_{1-4}$ alkyl, $C_{1-4}$ haloalkyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^d$, $NR^cC(O)OR^a$, $S(O)R^b$, $S(O)NR^cR^d$, $S(O)_2R^b$, and $S(O)_2NR^cR^d$.

8. The compound of claim 1, or pharmaceutically acceptable salt thereof, wherein two of $R^3$, $R^4$, $R^5$, and $R^6$ are attached to the same atom and together with the atom to which they are attached form a 3-7 membered cycloalkyl group or 3-7 membered heterocycloalkyl group.

9. The compound of claim 1, or pharmaceutically acceptable salt thereof, wherein two of $R^3$, $R^4$, $R^5$, and $R^6$ are attached to the same atom and together with the atom to which they are attached form a cyclopropyl group.

10. The compound of claim 1, or pharmaceutically acceptable salt thereof, wherein $R^1$ is —$(CR^{2a}R^{2b})_c$-$Cy^2$.

11. The compound of claim 1, or pharmaceutically acceptable salt thereof, wherein $R^1$ is aryl, heteroaryl, cycloalkyl, heterocycloalkyl, arylalkyl, heteroarylalkyl, cycloalkylalkyl, or heterocycloalkylalkyl each optionally substituted by 1, 2 or 3 substituents selected from halo, $C_{1-4}$ alkyl, $C_{1-4}$ haloalkyl, CN, $NO_2$, and $OR^{a3}$.

12. The compound of claim 1, or pharmaceutically acceptable salt thereof, wherein $R^1$ is aryl, heteroaryl, cycloalkyl, heterocycloalkyl, arylalkyl, heteroarylalkyl, cycloalkylalkyl, or heterocycloalkylalkyl each optionally substituted by 1, 2 or 3 halo.

13. The compound of claim 1, or pharmaceutically acceptable salt thereof, wherein $R^1$ is —$(CR^{2a}R^{2b})_c$-$Cy^2$ and $Cy^2$ is aryl, heteroaryl, cycloalkyl, and heterocycloalkyl, each optionally substituted by 1 or 2 substituents independently selected from halo and $OR^{a3}$.

14. The compound of claim 1, or pharmaceutically acceptable salt thereof, wherein R$^1$ is —(CR$^{2a}$R$^{2b}$)$_c$-Cy$^2$ and Cy$^2$ is aryl, heteroaryl, cycloalkyl, and heterocycloalkyl, each optionally substituted by 1 or 2 substituents independently selected from methoxy, OH, and Cl.

15. The compound of claim 1, or pharmaceutically acceptable salt thereof, wherein R$^1$ is —(CR$^{2a}$R$^{2b}$)$_c$-Cy$^2$ and Cy$^2$ is cycloalkyl optionally substituted by 1 or 2 substituents independently selected from methoxy, OH, and Cl.

16. The compound of claim 1, or pharmaceutically acceptable salt thereof, wherein R$^1$ is —(CR$^{2a}$R$^{2b}$)$_c$-Cy$^2$ and Cy$^2$ is cyclohexyl optionally substituted by 1 or 2 substituents independently selected from methoxy and OH.

17. The compound of claim 1, or pharmaceutically acceptable salt thereof, wherein R$^1$ is —(CR$^{2a}$R$^{2b}$)$_c$-Cy$^2$ and Cy$^2$ is cyclohexyl.

18. The compound of claim 1, or pharmaceutically acceptable salt thereof, wherein the compound is a compound according to Formula IV:

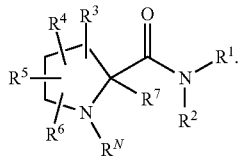

IV

19. The compound of claim 1, or pharmaceutically acceptable salt thereof, wherein the compound is a compound according to Formula Va or Vb:

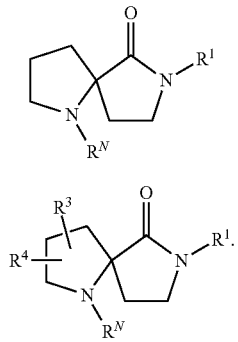

Va

Vb

20. The compound of claim 1, or pharmaceutically acceptable salt thereof, wherein the compound is a compound according to Formula VI:

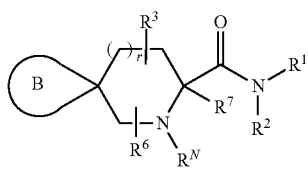

VI wherein ring B is a 3-20 membered cycloalkyl group or 3-20 membered heterocycloalkyl group, each optionally substituted by 1, 2, or 3 substituents independently selected from halo, C$_{1-4}$ alkyl, C$_{1-4}$ haloalkyl, aryl, cycloalkyl, heteroaryl, heterocycloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^d$, NR$^c$C(O)OR$^a$, S(O)R$^b$, S(O)NR$^c$R$^d$, S(O)$_2$R$^b$, and S(O)$_2$NR$^c$R$^d$.

21. The compound of claim 1, or pharmaceutically acceptable salt thereof, wherein the compound is a compound according to Formula VII:

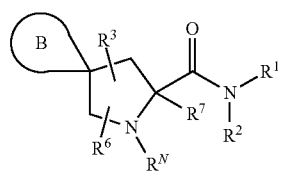

VII wherein ring B is a 3-20 membered cycloalkyl group or 3-20 membered heterocycloalkyl group, each optionally substituted by 1, 2, or 3 substituents independently selected from halo, C$_{1-4}$ alkyl, C$_{1-4}$ haloalkyl, aryl, cycloalkyl, heteroaryl, heterocycloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^d$, NR$^c$C(O)OR$^a$, S(O)R$^b$, S(O)NR$^c$R$^d$, S(O)$_2$R$^b$, and S(O)$_2$NR$^c$R$^d$.

22. A compound selected from:
7-(2-chlorophenyl)-1-isobutyl-1,7-diazaspiro[4.4]nonan-6-one;
7-(2-chlorophenyl)-1-(cyclopropylmethyl)-1,7-diazaspiro[4.4]nonan-6-one;
7-(2-chlorophenyl)-1-(tetrahydrofuran-3-ylmethyl)-1,7-diazaspiro[4.4]nonan-6-one;
7-(2-chlorophenyl)-1-(1H-imidazol-4-ylmethyl)-1,7-diazaspiro[4.4]nonan-6-one;
7-(2-chlorophenyl)-1-(1H-indol-5-ylmethyl)-1,7-diazaspiro[4.4]nonan-6-one;
7-(2-chlorophenyl)-1-(5-nitropyridin-2-yl)-1,7-diazaspiro[4.4]nonan-6-one;
7-(2-chlorophenyl)-1-[5-(trifluoromethyl)pyridin-2-yl]-1,7-diazaspiro[4.4]nonan-6-one;
7-(2-chlorophenyl)-1-{[4-(difluoromethoxy)phenyl]sulfonyl}-1,7-diazaspiro[4.4]nonan-6-one;
7-(1-adamantyl)-1-isobutyl-1,7-diazaspiro[4.4]nonan-6-one;
7-(1-adamantyl)-1-(pyridin-2-ylmethyl)-1,7-diazaspiro[4.4]nonan-6-one;
7-(1-adamantyl)-1-(cyclopentylmethyl)-1,7-diazaspiro[4.4]nonan-6-one;
7-(1-adamantyl)-1-[5-(trifluoromethyl)pyridin-2-yl]-1,7-diazaspiro[4.4]nonan-6-one;
7-(1-adamantyl)-1-[3-chloro-5-(trifluoromethyl)pyridin-2-yl]-1,7-diazaspiro[4.4]nonan-6-one;
6-[7-(1-adamantyl)-6-oxo-1,7-diazaspiro[4.4]non-1-yl]nicotinonitrile;
7-cyclohexyl-1-(cyclopentylmethyl)-1,7-diazaspiro[4.4]nonan-6-one;
4-[(7-cyclohexyl-6-oxo-1,7-diazaspiro[4.4]non-1-yl)methyl]benzonitrile;
1-(4-chlorobenzyl)-7-cyclohexyl-1,7-diazaspiro[4.4]nonan-6-one;
7-cyclohexyl-1-(2,4-difluorobenzyl)-1,7-diazaspiro[4.4]nonan-6-one;
7-cyclohexyl-1-{[6-(trifluoromethyl)pyridin-3-yl]methyl}-1,7-diazaspiro[4.4]nonan-6-one;
7-cyclohexyl-1-(1H-indol-3-ylmethyl)-1,7-diazaspiro[4.4]nonan-6-one;

ethyl 7-cyclohexyl-6-oxo-1,7-diazaspiro[4.4]nonane-1-carboxylate;
7-cyclohexyl-1-[2-fluoro-5-(trifluoromethyl)benzoyl]-1,7-diazaspiro[4.4]nonan-6-one;
1-(cyclobutylcarbonyl)-7-cyclohexyl-1,7-diazaspiro[4.4]nonan-6-one;
7-cyclohexyl-1-(pyridin-2-ylcarbonyl)-1,7-diazaspiro[4.4]nonan-6-one;
7-(2-chlorophenyl)-1-(ethylsulfonyl)-1,7-diazaspiro[4.4]nonan-6-one;
2-cyclohexyl-6-isobutyl-2,6-diazaspiro[4.5]decan-1-one;
2-cyclohexyl-6-(cyclopentylmethyl)-2,6-diazaspiro[4.5]decan-1-one;
2-cyclohexyl-6-(pyridin-2-ylmethyl)-2,6-diazaspiro[4.5]decan-1-one;
2-cyclohexyl-6-[5-(trifluoromethyl)pyridin-2-yl]-2,6-diazaspiro[4.5]decan-1-one;
(3R)-1-(4-chlorobenzyl)-7-cyclohexyl-3-hydroxy-1,7-diazaspiro[4.4]nonan-6-one;
(3R)-7-cyclohexyl-1-(1-cyclohexylethyl)-3-hydroxy-1,7-diazaspiro[4.4]nonan-6-one;
(3R)-7-cyclohexyl-1-(cyclohexylmethyl)-3-hydroxy-1,7-diazaspiro[4.4]nonan-6-one;
(3R)-1-[2-(3-bromophenyl)-1-methylethyl]-7-cyclohexyl-3-hydroxy-1,7-diazaspiro[4.4]nonan-6-one;
(3R)-7-cyclohexyl-1-(1-cyclopropylethyl)-3-hydroxy-1,7-diazaspiro[4.4]nonan-6-one;
(3R)-1-(4-bromobenzyl)-7-cyclohexyl-3-hydroxy-1,7-diazaspiro[4.4]nonan-6-one;
(3R)-1-(1-cyclobutylethyl)-7-cyclohexyl-3-hydroxy-1,7-diazaspiro[4.4]nonan-6-one;
3-{1-[(3R)-7-cyclohexyl-3-hydroxy-6-oxo-1,7-diazaspiro[4.4]non-1-yl]ethyl}-benzonitrile;
(3R)-7-cyclohexyl-3-hydroxy-1-[1-(3-methyl-2-oxotetrahydrofuran-3-yl)ethyl]-1,7-diazaspiro[4.4]nonan-6-one;
5-(4-{[(3R)-7-cyclohexyl-3-hydroxy-6-oxo-1,7-diazaspiro[4.4]non-1-yl]methyl}-2-fluorophenyl)-N-isopropylpyridine-2-carboxamide;
(3R)-7-cyclohexyl-3-hydroxy-1-(4-pyridin-4-ylbenzyl)-1,7-diazaspiro[4.4]nonan-6-one;
5-(4-{[(3R)-7-cyclohexyl-3-hydroxy-6-oxo-1,7-diazaspiro[4.4]non-1-yl]methyl}-phenyl)-N-ethylpyridine-2-carboxamide;
5-(4-{[(3R)-7-cyclohexyl-3-hydroxy-6-oxo-1,7-diazaspiro[4.4]non-1-yl]methyl}-3-fluorophenyl)-N-ethylpyridine-2-carboxamide;
(3R)-1-[1-(4-bromophenyl)ethyl]-7-cyclohexyl-3-hydroxy-1,7-diazaspiro[4.4]-nonan-6-one;
(3R)-7-cyclohexyl-1-[(2-fluorobiphenyl-4-Amethyl]-3-hydroxy-1,7-diazaspiro-[4.4]nonan-6-one;
(3R)-7-cyclohexyl-3-hydroxy-1-{4-[3-(trifluoromethyl)phenoxy]benzyl}-1,7-diazaspiro[4.4]nonan-6-one;
(3R)-7-cyclohexyl-1-[4-(dimethylamino)benzyl]-3-hydroxy-1,7-diazaspiro[4.4]-nonan-6-one;
(3R)-7-cyclohexyl-3-hydroxy-1-(4-morpholin-4-ylbenzyl)-1,7-diazaspiro[4.4]-nonan-6-one;
(3R)-7-cyclohexyl-3-hydroxy-1-[4-(pyrimidin-2-yloxy)benzyl]-1,7-diazaspiro-[4.4]nonan-6-one;
(3R)-7-cyclohexyl-1-(3-fluorobenzyl)-3-hydroxy-1,7-diazaspiro[4.4]nonan-6-one;
(3R)-7-cyclohexyl-3-hydroxy-1-(4-nitrobenzyl)-1,7-diazaspiro[4.4]nonan-6-one;
2-{[(3R)-7-cyclohexyl-3-hydroxy-6-oxo-1,7-diazaspiro[4.4]non-1-yl]methyl}-benzonitrile;
(3R)-7-cyclohexyl-3-hydroxy-1-{4-[3-(trifluoromethyl)-1H-pyrazol-1-yl]benzyl}-1,7-diazaspiro[4.4]nonan-6-one;
(3R)-7-cyclohexyl-3-hydroxy-1-[4-(2-oxopyrrolidin-1-yl)benzyl]-1,7-diazaspiro-[4.4]nonan-6-one;
5-(5-{[(3R)-7-cyclohexyl-3-hydroxy-6-oxo-1,7-diazaspiro[4.4]non-1-yl]methyl}-2-fluorophenyl)-N-ethylpyridine-2-carboxamide;
(3R)-7-cyclohexyl-1-{[6-(4-fluorophenyl)pyridin-3-yl]methyl}-3-hydroxy-1,7-diazaspiro[4.4]nonan-6-one;
3-(5-{[(3R)-7-cyclohexyl-3-hydroxy-6-oxo-1,7-diazaspiro[4.4]non-1-yl]methyl}-pyridin-2-yl)benzonitrile;
(3R)-7-cyclohexyl-1-{[6-(3,5-dimethylisoxazol-4-yl)pyridin-3-yl]methyl}-3-hydroxy-1,7-diazaspiro[4.4]nonan-6-one;
5-(3-{[(3R)-7-cyclohexyl-3-hydroxy-6-oxo-1,7-diazaspiro[4.4]non-1-yl]methyl}-phenyl)-N-ethylpyridine-2-carboxamide;
(3R)-7-cyclohexyl-1-(1-ethylpropyl)-3-hydroxy-1,7-diazaspiro[4.4]nonan-6-one;
(3R)-7-cyclohexyl-1-cyclopentyl-3-hydroxy-1,7-diazaspiro[4.4]nonan-6-one;
(3S)-1-(4-chlorobenzyl)-7-cyclohexyl-3-hydroxy-1,7-diazaspiro[4.4]nonan-6-one;
(3R)-7-cyclohexyl-1-(cyclopentylmethyl)-3-hydroxy-1,7-diazaspiro[4.4]nonan-6-one;
5-(4-{[(3R)-7-cyclohexyl-3-hydroxy-6-oxo-1,7-diazaspiro[4.4]non-1-yl]methyl}-2-fluorophenyl)-N,N-dimethylpyridine-2-carboxamide;
5-(4-{[(3R)-7-cyclohexyl-3-hydroxy-6-oxo-1,7-diazaspiro[4.4]non-1-yl]methyl}-phenyl)-N,N-dimethylpyridine-2-carboxamide;
2-(4-{[(3R)-7-cyclohexyl-3-hydroxy-6-oxo-1,7-diazaspiro[4.4]non-1-yl]methyl}-phenyl)isonicotinonitrile;
(3R)-1-[4-(5-chloropyridin-3-yl)benzyl]-7-cyclohexyl-3-hydroxy-1,7-diazaspiro-[4.4]nonan-6-one;
3-(4-{[(3R)-7-cyclohexyl-3-hydroxy-6-oxo-1,7-diazaspiro[4.4]non-1-yl]methyl}-phenyl)pyrazine-2-carbonitrile;
(3R)-7-cyclohexyl-1-[4-(3-fluoropyridin-4-yl)benzyl]-3-hydroxy-1,7-diazaspiro-[4.4]nonan-6-one;
(3R)-7-cyclohexyl-3-hydroxy-1-(4-pyrazin-2-ylbenzyl)-1,7-diazaspiro[4.4]nonan-6-one;
(3R)-1-[2-(4-bromophenyl)ethyl]-7-cyclohexyl-3-hydroxy-1,7-diazaspiro[4.4]-nonan-6-one;
(3R)-7-cyclohexyl-1-{[5-(3,4-difluorophenyl)pyridin-2-yl]methyl}-3-hydroxy-1,7-diazaspiro[4.4]nonan-6-one;
3-(6-{[(3R)-7-cyclohexyl-3-hydroxy-6-oxo-1,7-diazaspiro[4.4]non-1-yl]methyl}-pyridin-3-yl)benzonitrile;
6'-{[(3R)-7-cyclohexyl-3-hydroxy-6-oxo-1,7-diazaspiro[4.4]non-1-yl]methyl}-N-methyl-3,3'-bipyridine-6-carboxamide;
(3R)-1-{[1-(4-chlorophenyl)cyclopropyl]methyl}-7-cyclohexyl-3-hydroxy-1,7-diazaspiro[4.4]nonan-6-one;
4-(6-{[(3R)-7-cyclohexyl-3-hydroxy-6-oxo-1,7-diazaspiro[4.4]non-1-yl]methyl}-pyridin-3-yl)-N-cyclopropylbenzamide;
(3R)-7-cyclohexyl-1-(cyclopropylmethyl)-3-hydroxy-1,7-diazaspiro[4.4]nonan-6-one;
1-(4-chlorobenzyl)-7-cyclohexyl-3-hydroxy-3-methyl-1,7-diazaspiro[4.4]nonan-6-one;
(5S)-1-(4-chlorobenzyl)-7-cyclohexyl-3,3-difluoro-1,7-diazaspiro[4.4]nonan-6-one;
(3S)-1-(4-chlorobenzyl)-7-cyclohexyl-3-fluoro-1,7-diazaspiro[4.4]nonan-6-one;

5-(4-{[(3S)-7-cyclohexyl-3-fluoro-6-oxo-1,7-diazaspiro[4.4]non-1-yl]methyl}-phenyl)-N-methylpyridine-2-carboxamide;

1-(4-chlorobenzyl)-7-cycloheptyl-1,7-diazaspiro[4.4]nonan-6-one;

1-(4-chlorobenzyl)-7-cyclopentyl-1,7-diazaspiro[4.4]nonan-6-one;

5-{4-[(7-cyclohexyl-6-oxo-1,7-diazaspiro[4.4]non-1-yl)methyl]phenyl}-N-ethyl-pyridine-2-carboxamide;

7-cyclohexyl-1-[4-(5-methoxypyridin-3-yl)benzyl]-1,7-diazaspiro[4.4]nonan-6-one;

7-cyclohexyl-1-(4-pyridin-4-ylbenzyl)-1,7-diazaspiro[4.4]nonan-6-one;

7-cyclohexyl-1-[4-(difluoromethoxy)benzyl]-1,7-diazaspiro[4.4]nonan-6-one;

7-cyclohexyl-1-[(6-methoxypyridin-3-yl)methyl]-1,7-diazaspiro[4.4]nonan-6-one;

7-cyclohexyl-1-(4-phenoxybenzyl)-1,7-diazaspiro[4.4]nonan-6-one;

7-cyclohexyl-1-[4-(trifluoromethyl)benzyl]-1,7-diazaspiro[4.4]nonan-6-one;

5-[(7-cyclohexyl-6-oxo-1,7-diazaspiro[4.4]non-1-yl)methyl]-2-fluorobenzonitrile;

7-cyclohexyl-1-[4-(methylsulfonyl)benzyl]-1,7-diazaspiro[4.4]nonan-6-one;

7-cyclohexyl-1-[(1-methyl-1H-pyrrol-2-yl)methyl]-1,7-diazaspiro[4.4]nonan-6-one;

1-[2-chloro-4-(methylsulfonyl)benzyl]-7-cyclohexyl-1,7-diazaspiro[4.4]nonan-6-one;

N-{4-[(7-cyclohexyl-6-oxo-1,7-diazaspiro[4.4]non-1-yl)methyl]phenyl}acetamide;

1-(biphenyl-4-ylmethyl)-7-cyclohexyl-1,7-diazaspiro[4.4]nonan-6-one;

1-(biphenyl-2-ylmethyl)-7-cyclohexyl-1,7-diazaspiro[4.4]nonan-6-one;

7-cyclohexyl-1-(1,2,3-thiadiazol-4-ylmethyl)-1,7-diazaspiro[4.4]nonan-6-one;

1-(4-chlorobenzyl)-7-(2-methoxybenzyl)-1,7-diazaspiro[4.4]nonan-6-one;

1-(4-chlorobenzyl)-7-(trans-4-hydroxycyclohexyl)-1,7-diazaspiro[4.4]nonan-6-one;

1-(4-chlorobenzyl)-7-(tetrahydro-2H-pyran-4-yl)-1,7-diazaspiro[4.4]nonan-6-one;

1-(4-fluorobenzyl)-7-(tetrahydro-2H-pyran-4-yl)-1,7-diazaspiro[4.4]nonan-6-one;

7-cyclohexyl-1-(cyclopropylmethyl)-1,7-diazaspiro[4.4]nonan-6-one;

7-cyclohexyl-1-(pyridin-3-ylmethyl)-1,7-diazaspiro[4.4]nonan-6-one;

7-cyclohexyl-1-(pyridin-2-ylmethyl)-1,7-diazaspiro[4.4]nonan-6-one;

7-cyclohexyl-1-(pyridin-4-ylmethyl)-1,7-diazaspiro[4.4]nonan-6-one;

7-cyclohexyl-1-[(1-methyl-1H-imidazol-2-yl)methyl]-1,7-diazaspiro[4.4]nonan-6-one;

7-cyclohexyl-1-[(2,5-dimethyl-1,3-thiazol-4-yl)methyl]-1,7-diazaspiro[4.4]nonan-6-one;

7-cyclohexyl-1-[4-(1,2,3-thiadiazol-4-yl)benzyl]-1,7-diazaspiro[4.4]nonan-6-one;

1-(4-chlorobenzyl)-7-(2-methoxy-1-methylethyl)-1,7-diazaspiro[4.4]nonan-6-one; and 1-(4-chlorobenzyl)-7-(pyridin-4-ylmethyl)-1,7-diazaspiro[4.4]nonan-6-one; and pharmaceutically acceptable salts thereof.

23. A composition comprising a compound of claim 1, or pharmaceutically acceptable salt thereof, and at least one pharmaceutically acceptable carrier.

24. A method of inhibiting 11βHSD1 comprising contacting said 11βHSD1 with a compound according to claim 1, or a pharmaceutically acceptable salt thereof.

25. A method of ameliorating obesity, diabetes, glucose intolerance, insulin resistance, hyperglycemia, hyperlipidemia, or metabolic syndrome, in a patient in need thereof, comprising administering to said patient a therapeutically effective amount of a compound according to claim 1, or a pharmaceutically acceptable salt thereof.

26. A method of ameliorating type 2 diabetes in a patient in need thereof, comprising administering to said patient a therapeutically effective amount of a compound according to claim 1, or a pharmaceutically acceptable salt thereof.

27. A compound according to claim 10, or a pharmaceutically acceptable salt thereof, wherein c is 0.

28. A compound according to claim 13, or a pharmaceutically acceptable salt thereof, wherein c is 0.

29. A compound according to claim 14, or a pharmaceutically acceptable salt thereof, wherein c is 0.

30. A compound according to claim 15, or a pharmaceutically acceptable salt thereof, wherein c is 0.

31. A compound according to claim 16, or a pharmaceutically acceptable salt thereof, wherein c is 0.

32. A compound according to claim 17, or a pharmaceutically acceptable salt thereof, wherein c is 0.

33. A compound according to claim 1, wherein the compound is 1-(4-chlorobenzyl)-7-cyclohexyl-3-hydroxy-1,7-diazaspiro[4.4]nonan-6-one, or a pharmaceutically acceptable salt thereof.

34. A compound according to claim 1, wherein the compound is (3R)-1-(4-chlorobenzyl)-7-cyclohexyl-3-hydroxy-1,7-diazaspiro[4.4]nonan-6-one, or a pharmaceutically acceptable salt thereof.

35. A compound according to claim 1, wherein the compound is (3S)-1-(4-chlorobenzyl)-7-cyclohexyl-3-hydroxy-1,7-diazaspiro[4.4]nonan-6-one, or a pharmaceutically acceptable salt thereof.

36. A method of ameliorating obesity in a patient in need thereof, comprising administering to said patient a therapeutically effective amount of a compound according to claim 1, or a pharmaceutically acceptable salt thereof.

37. A method of ameliorating diabetes in a patient in need thereof, comprising administering to said patient a therapeutically effective amount of a compound according to claim 1, or a pharmaceutically acceptable salt thereof.

38. A method of ameliorating glucose intolerance in a patient in need thereof, comprising administering to said patient a therapeutically effective amount of a compound according to claim 1, or a pharmaceutically acceptable salt thereof.

39. A method of ameliorating insulin resistance in a patient in need thereof, comprising administering to said patient a therapeutically effective amount of a compound according to claim 1, or a pharmaceutically acceptable salt thereof.

40. A method of ameliorating hypergylcemia in a patient in need thereof, comprising administering to said patient a therapeutically effective amount of a compound according to claim 1, or a pharmaceutically acceptable salt thereof.

41. A method of ameliorating hyperlipidemia in a patient in need thereof, comprising administering to said patient a therapeutically effective amount of a compound according to claim 1, or a pharmaceutically acceptable salt thereof.

42. A method of ameliorating metabolic syndrome in a patient in need thereof, comprising administering to said patient a therapeutically effective amount of a compound according to claim 1, or a pharmaceutically acceptable salt thereof.

* * * * *

UNITED STATES PATENT AND TRADEMARK OFFICE
CERTIFICATE OF CORRECTION

| | |
|---|---|
| PATENT NO. | : 7,998,959 B2 |
| APPLICATION NO. | : 11/652191 |
| DATED | : August 16, 2011 |
| INVENTOR(S) | : Wenqing Yao et al. |

Page 1 of 1

It is certified that error appears in the above-identified patent and that said Letters Patent is hereby corrected as shown below:

In the Claims

Column 58, Line 4, Claim 1, delete "of ring A and" and insert -- and --.

Column 58, Line 11, Claim 1, delete "$OR^1$," and insert -- $OR^a$, --.

Column 58, Line 30, Claim 1, delete "$S(O)_2R^{b1}$" and insert -- $S(O)_2R^{b1}$, --.

Column 58, Line 48, Claim 1, delete "H, halo," and insert -- halo, --.

Column 58, Line 64, Claim 1, delete "$R^{b1}$, $R^{b2}$," and insert -- $R^{b1}$ and --.

Column 59, Line 3, Claim 1, after "$C_{1-6}$ haloalkyl," delete "$C_{1-6}$ haloalkyl,".

Column 59, Line 5, Claim 1, delete "$R^{c1}$, $R^{c2}$," and insert -- $R^{c1}$, --.

Column 59, Line 15, Claim 1, after "$C_{1-6}$ haloalkyl," delete "$C_{1-6}$ haloalkyl,".

Column 59, Line 21, Claim 1, after "$C_{1-6}$ haloalkyl," delete "$C_{1-6}$ haloalkyl,".

Column 59, Line 28, Claim 1, after "$C_{1-6}$ haloalkyl," delete "$C_{1-6}$ haloalkyl,".

Column 59, Line 35, Claim 1, after "$C_{1-6}$ haloalkyl," delete "$C_{1-6}$ haloalkyl,".

Column 59, Lines 49-50, Claim 1, after "$C_{1-6}$ haloalkyl," delete "$C_{1-6}$ haloalkyl,".

Column 59, Line 61, Claim 1, after "$C_{1-6}$ haloalkyl," delete "$C_{1-6}$ haloalkyl,".

Column 60, Line 1, Claim 1, after "$C_{1-6}$ haloalkyl," delete "$C_{1-6}$ haloalkyl,".

Column 62, Line 2, Claim 20, delete "$C(O)N^cR^d$," and insert -- $C(O)NR^cR^d$, --.

Column 62, Line 3, Claim 20, delete "$NR^aC(O)R^d$," and insert -- $NR^cC(O)R^d$, --.

Column 63, Line 27, Claim 22, delete "cyclopropylethyl" and insert -- cyclopropylethyl) --.

Column 63, Line 52, Claim 22, delete "-4-Amethyl]" and insert -- -4-yl)methyl] --.

Column 63, Line 54, Claim 22, delete "{4-" and insert -- {3- --.

Column 66, Line 52, Claim 40, "hypergylcemia" and insert -- hyperglycemia --.

Signed and Sealed this
Twelfth Day of November, 2013

Teresa Stanek Rea
*Deputy Director of the United States Patent and Trademark Office*